US008906875B2

(12) United States Patent
Feinberg et al.

(10) Patent No.: US 8,906,875 B2
(45) Date of Patent: Dec. 9, 2014

(54) METHODS OF TREATING VASCULAR INFLAMMATORY DISORDERS

(75) Inventors: Mark W. Feinberg, Newton, MA (US); Xinghui Sun, Somerville, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/583,963

(22) PCT Filed: Mar. 9, 2011

(86) PCT No.: PCT/US2011/027772
§ 371 (c)(1),
(2), (4) Date: Dec. 20, 2012

(87) PCT Pub. No.: WO2011/112732
PCT Pub. Date: Sep. 15, 2011

(65) Prior Publication Data
US 2013/0102546 A1  Apr. 25, 2013

Related U.S. Application Data

(60) Provisional application No. 61/313,274, filed on Mar. 12, 2010.

(51) Int. Cl.
*A61K 48/00* (2006.01)
*C07H 21/02* (2006.01)
*C07H 21/04* (2006.01)

(52) U.S. Cl.
USPC ............ 514/44; 536/23.1; 536/24.5; 424/450

(58) Field of Classification Search
None
See application file for complete search history.

(56) References Cited

U.S. PATENT DOCUMENTS

| | | | |
|---|---|---|---|
| 5,994,402 A | 11/1999 | Rotstein et al. | |
| 2005/0261218 A1 | 11/2005 | Esau et al. | |
| 2006/0167086 A1 | 7/2006 | Umezawa et al. | |
| 2009/0286736 A1 | 11/2009 | May et al. | |

FOREIGN PATENT DOCUMENTS

| | | | | |
|---|---|---|---|---|
| WO | WO2005013901 A2 * | 2/2005 | | 514/44 |
| WO | WO 2006/128245 | 12/2006 | | |
| WO | WO 2008/116267 | 10/2008 | | |
| WO | WO 2009/043353 A2 * | 4/2009 | | 514/44 |
| WO | WO 2009/148137 | 12/2009 | | |
| WO | WO 2011/112732 | 9/2011 | | |
| WO | WO 2008/061537 A2 * | 5/2013 | | 514/44 |

OTHER PUBLICATIONS

Gareus et al., "Endothelial Cell-Specific NF-κB Inhibition Protects Mice from Atherosclerosis," Cell Metabolism, vol. 8, pp. 372-383 (2008).

International Search Report and Written Opinion dated Jan. 10, 2012 issued in international application No. PCT/US2011/027772, 12 pgs.
International Preliminary Report on Patentability issued in PCT/US2011/027772 issued on Sep. 18, 2012.
abmgood.com, "Human Inflammation miRNA Array," posted on or about Sep. 12, 2011, retrieved Jan. 23, 2014, http://www.abmgood.com/Human-Inflammation-miRNA-Array.html, 5 pages.
Aird, "Endothelium as a Therapeutic Target in Sepsis," *Current Drug Targets*, 2007, 8:501-507.
Aird, "The role of the endothelium in severe sepsis and multiple organ dysfunction syndrome," *Blood*, 2003, 101:3765-3777.
Baker et al., "NF-κB, inflammation and metabolic disease," *Cell Metab.*, Jan. 2011, 13(1):11-22.
Bevilacqua et al., "Identification of an inducible endothelial-leukocyte adhesion molecule," *PNAS*, Dec. 1987, 84:9238-9242.
Boettger et al., "Acquisition of the contractile phenotype by murine arterial smooth muscle cells depends on the Mir143/145 gene cluster," *J. Clin. Invest.*, 2009, 119:2634-2647.
Bonetti et al., "Activation of NF-κB and c-jun Transcription Factors in Multiple Sclerosis Lesions: Implications for Oligodendrocyte Pathology," *Am J Path*, Nov. 1999, 155(5):1433-1438.
Cheng et al., "MicroRNA-145, a novel smooth muscle cell phenotypic marker and modulator, controls vascular neointimal lesion formation," *Circ. Res.*, 2009, 105:158-166.
Chu et al., "Translation Repression in Human Cells by MicroRNA-Induced Gene Silencing Requires RCK/p54," *PLoS Biol.*, 2006, 4(7):1122-1136.
Dave and Khalili, "Morphine Treatment of Human Monocyte-Derived Macrophages Induces Differential miRNA and Protein Expression: Impact on Inflammation and Oxidative Stress in the Central Nervous System," *J Cell Biochem*, 2010, 110:834-845.
De Winther et al., "Nuclear Factor κB Signaling in Atherogenesis," *Arterioscler Throm Vasc Biol*, May 2005, 904-914.
European Search Opinion in European Application No. 11 754 023.7, mailed Aug. 21, 2013.
Fagerlund et al., "NF-κB is Transported into the Nucleus by Importin α3 and Importin α4," *J. Biol. Chem.*, 2005, 280(16):15942-15951.
Fagerlund et al., "NF-κB p52, RelB and c-Rel are transported into the nubleus via a subset of importin α molecules," *Cellular Signaling*, 2008, 20:1442-1451.
Guo and War, "Forum Review: Role of Oxidants in Lung Injury During Sepsis," *Antioxidants & Redox Signaling*, 2007, 9(11): 1991-2002.
Gutteridge et al., "NF-κB Controls Cell Growth and Differentiation through Transcriptional Regulation of Cyclin D1," *Mol Cell Biol*, 1999, 19(8):5785-5799.

(Continued)

*Primary Examiner* — Amy Bowman
(74) *Attorney, Agent, or Firm* — Fish & Richardson P.C.

(57) ABSTRACT

Provided are methods of treating or delaying the onset of a vascular inflammatory disease (e.g., acute lung injury) in a subject including administering to the subject a therapeutically effective amount of a nucleic acid containing all or a part of the sequence of mature miR-181b (SEQ ID NO: 1). Also provided are methods of decreasing nuclear factor-R? (NF-R?) signaling in an endothelial cell including administering to the subject a nucleic acid containing all or a part of the sequence of mature miR-181b (SEQ ID NO: 1).

10 Claims, 24 Drawing Sheets

(56) References Cited

OTHER PUBLICATIONS

Hajra et al., "The NF-κB signal Transduction Pathway in Aortic Endothelial Cells in Primed for Activation in Regions Predisposed to Atherosclerotic Lesion Formation," *PNAS*, Aug. 2000, 97(16):9052-9057.

Hong et al., "MicroRNA-181b targets MLK2 in HL-60 cells," *Sci China Life Sci*, 2010, 53:101-106.

Iliopoulos et al., "STAT3 Activation of miR-21 and miR-181b-1 via PTEN and CYLD are Part of the Epigenetic Switch Linking Inflammation to Cancer," *Molecular Cell*, Aug. 2010, 39:493-506.

Iorio et al., "MicroRNAs in cancer: Small molecules with a huge impact," *J. Clin. Onc.*, 2009, 27:5848-5856.

Kaltschmidt et al , "Inhibition of NF-κB potentiates amyloid β-mediated neuronal apoptosis," *PNAS*, Aug. 1999, 96:9409-9414.

Kansas, "Selectins and Their Ligands: Current Concepts and Controversies," *Blood*, Nov. 1996, 88(9):3259-3287.

Kazenwadel et al., "Prox1 expression is negatively regulated by miR-181 in endothelial cells," *Blood*, Jun. 2010, 116:2395-2401.

Kempe et al., "NF-κB controls the global pro-inflammatory response in endothelial cells: evidence for the regulation of a pro-atherogenic program," *Nucleic Acids Research*, 2005, 33(16):5308-5319.

Kumar et al., "Nuclear factor-κB: its role in health and disease," *J Mol Med*, 2004, 82:434-448.

Kwon et al., "Inducible Expression of IκBα Repressor Mutants Interferes with NF-κB Activity and HIV-1 Replication in Jurkat T Cells," *J. Biol Chem*, 1998, 273:7431-7440.

Li et al., "Knockdown of microRNA-181 by lentivirus mediated siRNA expression vector decreases the arrhythmogenic effect of skeletal myoblast transplantation in rat with myocardial infarction," *Microvasc. Res*, 2009, 78:393-404.

Liu et al., "Pre-miRNA Loop Nucleotides Control the Distinct Activities of mir-181a-1 and mir-181c in Early T Cell Development," *PLoS One*, Oct. 2008, 3(10):e3592, 13pages.

Marcucci et al., "MicroRNA expression in cytogenetically normal acute meloid leukemia," *N. Eng. J Med*, 2008, 358:1919-1928.

Matthay and Idell, "Update on Acute Lung Injury and Cri6tical Care Medicine 2009," *American Journal of Respiratory and Critical Care Medicine*, 2010, 181:1027-1032.

Miyazawa et al., "Constitutive Transcription of the Human Interlevkin-6 Gene by Rheumatoid Synoviocytes: Spontaneous Activation of NF-κB and CBF1," *Am J Pathol*, Mar. 1998, 152(3):793-803.

Molestina et al., "Requirement for NF-κB in Transcriptional Activation of Monocyte Chemoactic Protein 1 by *Chlamydia pneumoniae* in Human Endothelial Cells," *Infection an Immunity*, Jul. 2000, 68(7):4282-4288.

Moschos, "Expression profiling in vivo demonstrates rapid changes in lung microRNA levels following lipopolysaccharide-induced inflammation but not in the anti-inflammatory action of glucocorticoids," *BMC Genomics*, 2007, 8:240-251.

Novosel and Borkhardt, "miRNA patterns in hemotopoietic malignancies," *Microarrays in Inflammation*, 2008, 161, Abstract Only.

Oeckinghaus and Ghosh, "The NF-κB Family of Transcription Factors and its Regulation," *Cold Spring Harb Perspect Biol*, 2009, 1:a000034.

Pahl, "Activators and target genes of Rel/NF-κB Transcription Factors," *Oncogene*, 1999, 18:6853-6866.

Park and Christman, "Nuclear Factor Kappa B is a Promising Therapeutic Target in Inflammatory Lung Disease," *Current Drug Targets*, 2006, 7:661-668.

Quinto et al., "Potent and Stable Attenuation of Live-HIV-1 by Gain of a Proteolysis-resistant Inhibitor of NF-κB(Ik BαS32/36A) and the Implications for Vaccine Development," *J Biol Chem*, 1999, 274:17567-17572.

Rubenfeld et al., "Incidence and Outcomes of Acute Lung Injury," *The New England Journal of Medicine*, Oct. 2005, 353(16):1685-1693.

Shapiro et al., "The association of endothelial cell signaling severity of illness, and organ dysfunction in sepsis," *Critical Care*, 2010, 14:R182, 12 pages.

Shoelson et al., "Inflammation and the IKKβ/IκB/NF-κb axis in obesity- and diet-induced insulin resistance," *International Journal of Obesity*, 2003, 27:S49-S52.

Slaby et al., "MicroRNA-181 family predicts response to concomitant chemoradiotherapy with temozolomide in glioblastoma patients,"*Neoplasma*, 2010, 57:264-269.

Small et al., "MicroRNAs add a new dimension to cardiovascular disease," *Circulation*, 2010, 121:1022-1032.

Sun et al., "MicroRNA-181b regulates NF-κb-mediated vascular inflammation," *The Journal of Clinical Investigation*, 2012,122(6):1973-1990.

Sun et al., "Systemic Delivery of MicroRNA-181b Inhibits NF-κB Activation, Vascular Inflammation, and Atherosclerosis in Apoe-/- Mice," *Circ. Res.*, 2014 (published online Oct. 1, 2013)114(1):32-40.

Supplementary European Search Report in European Application No. 11 754 023.7, mailed Aug. 21, 2013, 4 pages.

Tilg and Moschen, "Inflammatory Mechanisms in the Regulation of Insulin Resistance," *Mol Med*, Mar./Apr. 2008, 14:222-231.

Turpin et al., "Characterization of IkappaBalpha nuclear import pathway," *J. Biol. Chem.*, 1999, 274:6804-6812.

Van Der Heiden et al., "Role of nuclear factor κB in cardiovascular health and disease," *Clinical Science*, 2010, 593-605.

Van Rooij et al., "Toward microRNA-based therapeutics for heart disease: the sense in antisense," *Circ. Res.*, 2008, 103:919-928.

Weber, "New Human and Mouse microRNA genes found by homology search," *FEBS Journal*, 2004, 272:59-73.

Woodman et al., "Thrombin and Leukocyte recruitment in Endotoxemia," *Am J Physiol Heart Circ Physiol*, 2000, 279:H1338-H1345.

Yebenes et al., "miR-181b negatively regulates activation-induced cytidine deaminase in B cells," *J Ex Med*, Sep. 2008, 205(1):2199-2206.

Zhang et al., "Role of TNF-α in vascular dysfunction," Clinical Science, 2009, 116:219-230.

\* cited by examiner

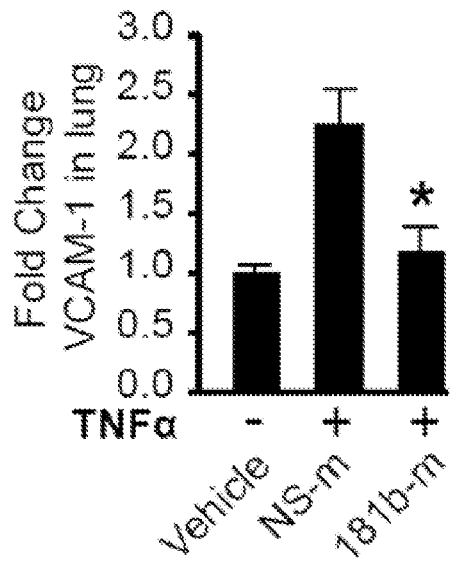
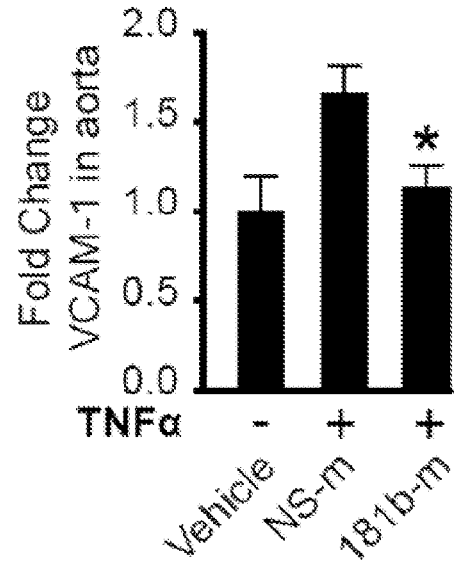
FIG. 3D
FIG. 3E
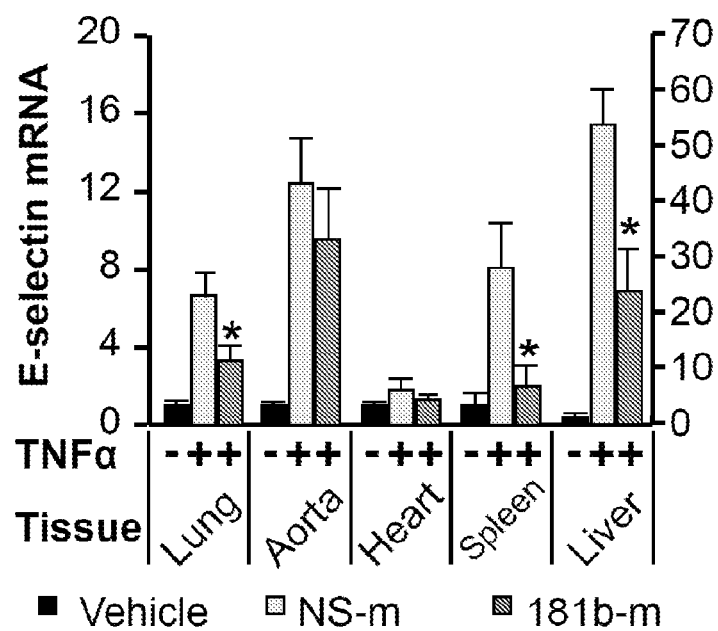
FIG. 4A

```
3UTR site1   - CUUG CUAUGAAGCAGUGUGUGAA
    442-464    | :    | :      | | | : | |   : | |
  miR-181b   UGGGUGGCUG-UCGUUACUUACAA
   site1 mut  - CUUGCUAUGAUA AAGCUUCUGAA
                          • • •      •    • •

3UTR site2   - - - -AUGGACAAUGUUGAAUGAAUGUC
    464-486      | :   | | | |    | :    | | | | | | | |
  miR-181b   UGGGUGGCUGU--CG- -UUACUUACAA
   site2 mut  - - - -AGGCUGAAUCUUGCCAACAUCAC
                      • • •  •       •    • • •   • •

3UTR site3   CUGUGUACGAGAGCG-UGGUUGUG
    568-590    | | |    | | | :   | |     | | |
  miR-181b   UGGGUG-GCUGUCGUUACUUACAA 3UTR site4   UGGUUUACUCUGCAGCCU- - -GUGUU
    722-744    : : : | | :     : | | | |           : | | | |
  miR-181b   U- -GGUGGC-UGUCGUUACUUACAA 3UTR site5   UG -CAUUUGCACCAGAUGAAUGUU
    903-925    | | :     : | |     : | | | | | | | |
  miR-181b   UGGGUGGCUGUCG-UUACUUACAA 3UTR site6   UUUCCCUCAAA AUAGACU- - -GUGUU
    997-1019   | | |  |    | : | |           : | | | |
  miR-181b   U- -GGUGGC-UGUCGUUACUUACAA 3UTR site7   A- - UACCGU- -GCUGUGUUUAAAUGUU
    1198-1220   : | | | |      | |  : | |      | | | | |
  miR-181b   UGGGUGGCUGUCGUUAC- - - -UUACAA 3UTR site8   CUUCCC- CUUUGAGCACA- AGUGUU
    1617-1639  | | |  | :       | | | |      | : | | | |
  miR-181b   U- -GGGUGGCUGUCGUUACUUACAA
```

FIG. 8A

Enriched GO biological processes down-regulated in miR-181b over-expression cells, identified by GSEA at 25% false discovery rate (FDR)

| GO biological processes | Description of gene set | FDR |
|---|---|---|
| GO:0034097 | Response to cytokine stimulus | 0.013 |
| GO:0030335 | Positive regulation of cell migration | 0.171 |
| GO:0050727 | Regulation of inflammatory response | 0.178 |
| GO:0006954 | Inflammatory response | 0.194 |
| GO:0006935 | Chemotaxis | 0.195 |
| GO:0007249 | I-kappaB kinase/NF-kappaB cascade | 0.224 |

FIG. 9D

SEQUENCE LISTING

```
<160> NUMBER OF SEQ ID NOS: 130

<210> SEQ ID NO 1
<211> LENGTH: 23
<212> TYPE: RNA
<213> ORGANISM: Homo sapiens
<220> FEATURE:
<223> OTHER INFORMATION: Mature human miR-181b

<400> SEQUENCE: 1
aacauucauu gcugucggug ggu                                          23

<210> SEQ ID NO 2
<211> LENGTH: 110
<212> TYPE: RNA
<213> ORGANISM: Homo sapiens
<220> FEATURE:
<223> OTHER INFORMATION: Precursor human miR-181b-1

<400> SEQUENCE: 2
ccugugcaga gauuauuuuu uaaaagguca caaucaacau ucauugcugu cgguggguug    60
aacugugugg acaagcucac ugaacaauga augcaacugu ggccccgcuu              110

<210> SEQ ID NO 3
<211> LENGTH: 89
<212> TYPE: RNA
<213> ORGANISM: Homo sapiens
<220> FEATURE:
<223> OTHER INFORMATION: Precursor human miR-181b-2

<400> SEQUENCE: 3
cugauggcug cacucaacau ucauugcugu cggugguuu gagucugaau caacucacug    60
aucaaugaau gcaaacugcg gaccaaaca                                     89

<210> SEQ ID NO 4
<211> LENGTH: 27
<212> TYPE: DNA
<213> ORGANISM: Artificial Sequence
<220> FEATURE:
<223> OTHER INFORMATION: miR-181b forward primer

<400> SEQUENCE: 4
cccaagcttt gattgtaccc tatggct                                       27
```

```
<210> SEQ ID NO 5
<211> LENGTH: 27
<212> TYPE: DNA
<213> ORGANISM: Artificial Sequence
<220> FEATURE:
<223> OTHER INFORMATION: miR-181b reverse primer

<400> SEQUENCE: 5
cggggtacct gtacgtttga tggacaa                                          27

<210> SEQ ID NO 6
<211> LENGTH: 19
<212> TYPE: DNA
<213> ORGANISM: Artificial Sequence
<220> FEATURE:
<223> OTHER INFORMATION: Mouse VCAM-1 forward primer

<400> SEQUENCE: 6
gttccagcga gggtctacc                                                   19

<210> SEQ ID NO 7
<211> LENGTH: 23
<212> TYPE: DNA
<213> ORGANISM: Artificial Sequence
<220> FEATURE:
<223> OTHER INFORMATION: Mouse VCAM-1 reverse primer

<400> SEQUENCE: 7
aactcttggc aaacattagg tgt                                              23

<210> SEQ ID NO 8
<211> LENGTH: 19
<212> TYPE: DNA
<213> ORGANISM: Artificial Sequence
<220> FEATURE:
<223> OTHER INFORMATION: Mouse E-selectin forward primer

<400> SEQUENCE: 8
atgcctcgcg ctttctctc                                                   19

<210> SEQ ID NO 9
<211> LENGTH: 21
<212> TYPE: DNA
<213> ORGANISM: Artificial Sequence
<220> FEATURE:
<223> OTHER INFORMATION: Mouse E-selectin reverse primer

<400> SEQUENCE: 9
gtagtcccgc tgacagtatg c                                                21

<210> SEQ ID NO 10
<211> LENGTH: 22
<212> TYPE: DNA
<213> ORGANISM: Artificial Sequence
<220> FEATURE:
<223> OTHER INFORMATION: Mouse ICAM-1 forward primer

<400> SEQUENCE: 10
gtgatgctca ggtatccatc ca                                               22

<210> SEQ ID NO 11
<211> LENGTH: 21
<212> TYPE: DNA
<213> ORGANISM: Artificial Sequence
<220> FEATURE:
<223> OTHER INFORMATION: Mouse ICAM-1 reverse primer
```

```
<400> SEQUENCE: 11
cacagttctc aaagcacagc g                                              21

<210> SEQ ID NO 12
<211> LENGTH: 22
<212> TYPE: DNA
<213> ORGANISM: Artificial Sequence
<220> FEATURE:
<223> OTHER INFORMATION: Mouse actin forward primer

<400> SEQUENCE: 12
gaaatcgtgc gtgacatcaa ag                                             22

<210> SEQ ID NO 13
<211> LENGTH: 22
<212> TYPE: DNA
<213> ORGANISM: Artificial Sequence
<220> FEATURE:
<223> OTHER INFORMATION: Mouse actin reverse primer

<400> SEQUENCE: 13
tgtagtttca tggatgccac ag                                             22

<210> SEQ ID NO 14
<211> LENGTH: 19
<212> TYPE: DNA
<213> ORGANISM: Artificial Sequence
<220> FEATURE:
<223> OTHER INFORMATION: Human PAI-1 forward primer

<400> SEQUENCE: 14
catcccccat cctacgtgg                                                 19

<210> SEQ ID NO 15
<211> LENGTH: 21
<212> TYPE: DNA
<213> ORGANISM: Artificial Sequence
<220> FEATURE:
<223> OTHER INFORMATION: Human PAI-1 reverse primer

<400> SEQUENCE: 15
ccccataggg tgagaaaacc a                                              21

<210> SEQ ID NO 16
<211> LENGTH: 21
<212> TYPE: DNA
<213> ORGANISM: Artificial Sequence
<220> FEATURE:
<223> OTHER INFORMATION: Human VCAM-1 forward primer

<400> SEQUENCE: 16
gctgctcaga ttggagactc a                                              21

<210> SEQ ID NO 17
<211> LENGTH: 20
<212> TYPE: DNA
<213> ORGANISM: Artificial Sequence
<220> FEATURE:
<223> OTHER INFORMATION: Human VCAM-1 reverse primer

<400> SEQUENCE: 17
cgctcagagg gctgtctatc                                                20

<210> SEQ ID NO 18
<211> LENGTH: 19
```

```
<212> TYPE: DNA
<213> ORGANISM: Artificial Sequence
<220> FEATURE:
<223> OTHER INFORMATION: Human E-selectin forward primer

<400> SEQUENCE: 18
aatccagcca atgggttcg                                                    19

<210> SEQ ID NO 19
<211> LENGTH: 24
<212> TYPE: DNA
<213> ORGANISM: Artificial Sequence
<220> FEATURE:
<223> OTHER INFORMATION: Human E-selectin reverse primer

<400> SEQUENCE: 19
gctcccatta gttcaaatcc ttct                                              24

<210> SEQ ID NO 20
<211> LENGTH: 21
<212> TYPE: DNA
<213> ORGANISM: Artificial Sequence
<220> FEATURE:
<223> OTHER INFORMATION: Human ICAM-1 forward primer

<400> SEQUENCE: 20
tctgtgtccc cctcaaaagt c                                                 21

<210> SEQ ID NO 21
<211> LENGTH: 20
<212> TYPE: DNA
<213> ORGANISM: Artificial Sequence
<220> FEATURE:
<223> OTHER INFORMATION: Human ICAM-1 reverse primer

<400> SEQUENCE: 21
ggggtctcta tgcccaacaa                                                   20

<210> SEQ ID NO 22
<211> LENGTH: 19
<212> TYPE: DNA
<213> ORGANISM: Artificial Sequence
<220> FEATURE:
<223> OTHER INFORMATION: human GAPDH forward primer

<400> SEQUENCE: 22
atggggaagg tgaaggtcg                                                    19

<210> SEQ ID NO 23
<211> LENGTH: 22
<212> TYPE: DNA
<213> ORGANISM: Artificial Sequence
<220> FEATURE:
<223> OTHER INFORMATION: Human GAPDH reverse primer

<400> SEQUENCE: 23
ggggtcattg atggcaacaa ta                                                22

<210> SEQ ID NO 24
<211> LENGTH: 21
<212> TYPE: DNA
<213> ORGANISM: Artificial Sequence
<220> FEATURE:
<223> OTHER INFORMATION: Mouse importin-alpha 3 forward primer

<400> SEQUENCE: 24
```

```
ccagtgatcg aaatccacca a                                           21

<210> SEQ ID NO 25
<211> LENGTH: 22
<212> TYPE: DNA
<213> ORGANISM: Artificial Sequence
<220> FEATURE:
<223> OTHER INFORMATION: Mouse importin-alpha 3 reverse primer

<400> SEQUENCE: 25
cgtttgttca gacgttccag at                                          22

<210> SEQ ID NO 26
<211> LENGTH: 21
<212> TYPE: DNA
<213> ORGANISM: Artificial Sequence
<220> FEATURE:
<223> OTHER INFORMATION: Human importin-alpha 3 forward primer

<400> SEQUENCE: 26
tccagtgatc gaaatccacc a                                           21

<210> SEQ ID NO 27
<211> LENGTH: 23
<212> TYPE: DNA
<213> ORGANISM: Artificial Sequence
<220> FEATURE:
<223> OTHER INFORMATION: Human importin-alpha 3 reverse primer

<400> SEQUENCE: 27
cattggactg aactactgct tga                                         23

<210> SEQ ID NO 28
<211> LENGTH: 21
<212> TYPE: DNA
<213> ORGANISM: Artificial Sequence
<220> FEATURE:
<223> OTHER INFORMATION: human Smad1 forward primer

<400> SEQUENCE: 28
gatgccaggt aggttggaat g                                           21

<210> SEQ ID NO 29
<211> LENGTH: 22
<212> TYPE: DNA
<213> ORGANISM: Artificial Sequence
<220> FEATURE:
<223> OTHER INFORMATION: Human Smad1 reverse primer

<400> SEQUENCE: 29
cgtgacactg tgataacact gt                                          22

<210> SEQ ID NO 30
<211> LENGTH: 29
<212> TYPE: DNA
<213> ORGANISM: Artificial Sequence
<220> FEATURE:
<223> OTHER INFORMATION: Human importin-alpha 3 site 1 forward primer

<400> SEQUENCE: 30
ctagtcttgc tatgaagcag tgtgtgaaa                                   29

<210> SEQ ID NO 31
<211> LENGTH: 29
<212> TYPE: DNA
<213> ORGANISM: Artificial Sequence
```

```
<220> FEATURE:
<223> OTHER INFORMATION: Human importin-alpha 3 site 1 reverse primer

<400> SEQUENCE: 31
agcttttcac acactgcttc atagcaaga                                              29

<210> SEQ ID NO 32
<211> LENGTH: 29
<212> TYPE: DNA
<213> ORGANISM: Artificial Sequence
<220> FEATURE:
<223> OTHER INFORMATION: Human importin-alpha 3 site 2 forward primer

<400> SEQUENCE: 32
ctagtatgga caatgttgaa tgaatgtca                                              29

<210> SEQ ID NO 33
<211> LENGTH: 29
<212> TYPE: DNA
<213> ORGANISM: Artificial Sequence
<220> FEATURE:
<223> OTHER INFORMATION: Human importin-alpha 3 site 2 reverse primer

<400> SEQUENCE: 33
agcttgacat tcattcaaca ttgtccata                                              29

<210> SEQ ID NO 34
<211> LENGTH: 29
<212> TYPE: DNA
<213> ORGANISM: Artificial Sequence
<220> FEATURE:
<223> OTHER INFORMATION: Human importin-alpha 3 site 3 forward primer

<400> SEQUENCE: 34
ctagtctgtg tacgagagcg tggttgtga                                              29

<210> SEQ ID NO 35
<211> LENGTH: 29
<212> TYPE: DNA
<213> ORGANISM: Artificial Sequence
<220> FEATURE:
<223> OTHER INFORMATION: Human importin-alpha 3 site 3 reverse primer

<400> SEQUENCE: 35
agcttcacaa ccacgctctc gtacacaga                                              29

<210> SEQ ID NO 36
<211> LENGTH: 29
<212> TYPE: DNA
<213> ORGANISM: Artificial Sequence
<220> FEATURE:
<223> OTHER INFORMATION: Human importin-alpha 3 site 4 forward primer

<400> SEQUENCE: 36
ctagttggtt tactctgcag cctgtgtta                                              29

<210> SEQ ID NO 37
<211> LENGTH: 29
<212> TYPE: DNA
<213> ORGANISM: Artificial Sequence
<220> FEATURE:
<223> OTHER INFORMATION: Human importin-alpha 3 site 4 reverse primer

<400> SEQUENCE: 37
agcttaacac aggctgcaga gtaaaccaa                                              29
```

```
<210> SEQ ID NO 38
<211> LENGTH: 29
<212> TYPE: DNA
<213> ORGANISM: Artificial Sequence
<220> FEATURE:
<223> OTHER INFORMATION: Human importin-alpha 3 site 5 forward primer

<400> SEQUENCE: 38
ctagttgcat ttgcaccaga tgaatgtta                                29

<210> SEQ ID NO 39
<211> LENGTH: 29
<212> TYPE: DNA
<213> ORGANISM: Artificial Sequence
<220> FEATURE:
<223> OTHER INFORMATION: Human importin-alpha 3 site 5 reverse primer

<400> SEQUENCE: 39
agcttaacat tcatctggtg caaatgcaa                                29

<210> SEQ ID NO 40
<211> LENGTH: 29
<212> TYPE: DNA
<213> ORGANISM: Artificial Sequence
<220> FEATURE:
<223> OTHER INFORMATION: Human importin-alpha 3 site 6 forward primer

<400> SEQUENCE: 40
ctagttttcc ctcaaaatag actgtgtta                                29

<210> SEQ ID NO 41
<211> LENGTH: 29
<212> TYPE: DNA
<213> ORGANISM: Artificial Sequence
<220> FEATURE:
<223> OTHER INFORMATION: Human importin-alpha 3 site 6 reverse primer

<400> SEQUENCE: 41
agcttaacac agtctatttt gagggaaaa                                29

<210> SEQ ID NO 42
<211> LENGTH: 29
<212> TYPE: DNA
<213> ORGANISM: Artificial Sequence
<220> FEATURE:
<223> OTHER INFORMATION: Human importin-alpha 3 site 7 forward primer

<400> SEQUENCE: 42
ctagtatacc gtgctgtgtt taaatgtta                                29

<210> SEQ ID NO 43
<211> LENGTH: 29
<212> TYPE: DNA
<213> ORGANISM: Artificial Sequence
<220> FEATURE:
<223> OTHER INFORMATION: Human importin-alpha 3 site 7 reverse primer

<400> SEQUENCE: 43
agcttaacat ttaaacacag cacggtata                                29

<210> SEQ ID NO 44
<211> LENGTH: 29
<212> TYPE: DNA
<213> ORGANISM: Artificial Sequence
<220> FEATURE:
<223> OTHER INFORMATION: Human importin-alpha 3 site 8 forward primer
```

<400> SEQUENCE: 44
ctagtcttcc cctttgagca caagtgtta                                           29

<210> SEQ ID NO 45
<211> LENGTH: 29
<212> TYPE: DNA
<213> ORGANISM: Artificial Sequence
<220> FEATURE:
<223> OTHER INFORMATION: Human importin-alpha 3 site 8 reverse primer

<400> SEQUENCE: 45
agcttaacac ttgtgctcaa aggggaaga                                           29

<210> SEQ ID NO 46
<211> LENGTH: 29
<212> TYPE: DNA
<213> ORGANISM: Artificial Sequence
<220> FEATURE:
<223> OTHER INFORMATION: Human importin-alpha 3 site 1 mutant forward
      primer

<400> SEQUENCE: 46
ctagtcttgc tatgataaag cttctgaaa                                           29

<210> SEQ ID NO 47
<211> LENGTH: 29
<212> TYPE: DNA
<213> ORGANISM: Artificial Sequence
<220> FEATURE:
<223> OTHER INFORMATION: Human importin-alpha 3 site 1 mutant reverse
      primer

<400> SEQUENCE: 47
agcttttcag aagctttatc atagcaaga                                           29

<210> SEQ ID NO 48
<211> LENGTH: 29
<212> TYPE: DNA
<213> ORGANISM: Artificial Sequence
<220> FEATURE:
<223> OTHER INFORMATION: Human importin-alpha 3 site 2 mutant forward
      primer

<400> SEQUENCE: 48
ctagtaggct gaatcttgcc aacatcaca                                           29

<210> SEQ ID NO 49
<211> LENGTH: 29
<212> TYPE: DNA
<213> ORGANISM: Artificial Sequence
<220> FEATURE:
<223> OTHER INFORMATION: Human importin-alpha 3 site 2 mutant reverse
      primer

<400> SEQUENCE: 49
agcttgtgat gttggcaaga ttcagccta                                           29

<210> SEQ ID NO 50
<211> LENGTH: 33
<212> TYPE: DNA
<213> ORGANISM: Artificial Sequence
<220> FEATURE:
<223> OTHER INFORMATION: Human importin-alpha 1 3'-UTR forward primer

<400> SEQUENCE: 50
acgagctcat catgtagctg agacataaat ttg                               33

<210> SEQ ID NO 51
<211> LENGTH: 31
<212> TYPE: DNA
<213> ORGANISM: Artificial Sequence
<220> FEATURE:
<223> OTHER INFORMATION: Human importin-alpha 1 3'-UTR reverse primer

<400> SEQUENCE: 51
ataacgcgta gaaagggtg gacttgaatg t                                  31

<210> SEQ ID NO 52
<211> LENGTH: 29
<212> TYPE: DNA
<213> ORGANISM: Artificial Sequence
<220> FEATURE:
<223> OTHER INFORMATION: Human importin-alpha 3 3'-UTR forward primer

<400> SEQUENCE: 52
acgagctcaa agatgttgtg gaagttagg                                    29

<210> SEQ ID NO 53
<211> LENGTH: 30
<212> TYPE: DNA
<213> ORGANISM: Artificial Sequence
<220> FEATURE:
<223> OTHER INFORMATION: Human importin-alpha 3 3'-UTR reverse primer

<400> SEQUENCE: 53
ataacgcgtc acagcacggt attctaccac                                   30

<210> SEQ ID NO 54
<211> LENGTH: 28
<212> TYPE: DNA
<213> ORGANISM: Artificial Sequence
<220> FEATURE:
<223> OTHER INFORMATION: Human importin-alpha 4 3'-UTR forward primer

<400> SEQUENCE: 54
acgagctcat tcagttgagt gcagcatc                                     28

<210> SEQ ID NO 55
<211> LENGTH: 29
<212> TYPE: DNA
<213> ORGANISM: Artificial Sequence
<220> FEATURE:
<223> OTHER INFORMATION: Human importin-alpha 4 3'-UTR reverse primer

<400> SEQUENCE: 55
ataacgcgtc ctctacacag atccctgtc                                    29

<210> SEQ ID NO 56
<211> LENGTH: 28
<212> TYPE: DNA
<213> ORGANISM: Artificial Sequence
<220> FEATURE:
<223> OTHER INFORMATION: Human importin-alpha 5 3'-UTR forward primer

<400> SEQUENCE: 56
acgagctcag caatactctg ctttcacg                                     28

<210> SEQ ID NO 57
<211> LENGTH: 29
<212> TYPE: DNA
<213> ORGANISM: Artificial Sequence

```
<220> FEATURE:
<223> OTHER INFORMATION: Human importin-alpha 5 3'-UTR reverse primer

<400> SEQUENCE: 57
ataacgcgtg attagaatcg agctgcacc                                             29

<210> SEQ ID NO 58
<211> LENGTH: 27
<212> TYPE: DNA
<213> ORGANISM: Artificial Sequence
<220> FEATURE:
<223> OTHER INFORMATION: Human VCAM-1 3'-UTR forward primer

<400> SEQUENCE: 58
tcgacgcgtg caaatccttg atactgc                                               27

<210> SEQ ID NO 59
<211> LENGTH: 27
<212> TYPE: DNA
<213> ORGANISM: Artificial Sequence
<220> FEATURE:
<223> OTHER INFORMATION: Human VCAM01 3'-UTR reverse primer

<400> SEQUENCE: 59
cccaagctta ttgggaaagt tgcacag                                               27

<210> SEQ ID NO 60
<211> LENGTH: 21
<212> TYPE: DNA
<213> ORGANISM: Artificial Sequence
<220> FEATURE:
<223> OTHER INFORMATION: Human BCL2A1 forward primer

<400> SEQUENCE: 60
tacaggctgg ctcaggacta t                                                     21

<210> SEQ ID NO 61
<211> LENGTH: 22
<212> TYPE: DNA
<213> ORGANISM: Artificial Sequence
<220> FEATURE:
<223> OTHER INFORMATION: Human BCL2A1 reverse primer

<400> SEQUENCE: 61
ttttgtagca ctctggacgt tt                                                    22

<210> SEQ ID NO 62
<211> LENGTH: 23
<212> TYPE: DNA
<213> ORGANISM: Artificial Sequence
<220> FEATURE:
<223> OTHER INFORMATION: Human C1QTNF1 forward primer

<400> SEQUENCE: 62
caagggaaat atggcaaaac agg                                                   23

<210> SEQ ID NO 63
<211> LENGTH: 21
<212> TYPE: DNA
<213> ORGANISM: Artificial Sequence
<220> FEATURE:
<223> OTHER INFORMATION: Human C1QTNF1 reverse primer

<400> SEQUENCE: 63
atcaccgtct ggtagtagtg g                                                     21
```

<210> SEQ ID NO 64
<211> LENGTH: 21
<212> TYPE: DNA
<213> ORGANISM: Artificial Sequence
<220> FEATURE:
<223> OTHER INFORMATION: Human CCL1 forward primer

<400> SEQUENCE: 64
tcatttgcgg agcaagagat t                                          21

<210> SEQ ID NO 65
<211> LENGTH: 21
<212> TYPE: DNA
<213> ORGANISM: Artificial Sequence
<220> FEATURE:
<223> OTHER INFORMATION: Human CCL1 reverse primer

<400> SEQUENCE: 65
ctgaacccat ccaactgtgt c                                          21

<210> SEQ ID NO 66
<211> LENGTH: 20
<212> TYPE: DNA
<213> ORGANISM: Artificial Sequence
<220> FEATURE:
<223> OTHER INFORMATION: Human CCL7 forward primer

<400> SEQUENCE: 66
ccaatgcatc cacatgctgc                                            20

<210> SEQ ID NO 67
<211> LENGTH: 19
<212> TYPE: DNA
<213> ORGANISM: Artificial Sequence
<220> FEATURE:
<223> OTHER INFORMATION: Human CCL7 reverse primer

<400> SEQUENCE: 67
gcttcccagg gacaccgac                                             19

<210> SEQ ID NO 68
<211> LENGTH: 24
<212> TYPE: DNA
<213> ORGANISM: Artificial Sequence
<220> FEATURE:
<223> OTHER INFORMATION: Human CCR2 forward primer

<400> SEQUENCE: 68
gaccaggaaa gaatgtgaaa gtga                                       24

<210> SEQ ID NO 69
<211> LENGTH: 22
<212> TYPE: DNA
<213> ORGANISM: Artificial Sequence
<220> FEATURE:
<223> OTHER INFORMATION: Human CCR2 reverse primer

<400> SEQUENCE: 69
gctctgccaa ttgactttcc tt                                         22

<210> SEQ ID NO 70
<211> LENGTH: 20
<212> TYPE: DNA
<213> ORGANISM: Artificial Sequence
<220> FEATURE:
<223> OTHER INFORMATION: Human CFB forward primer -continued

```
<400> SEQUENCE: 70
gcggcccctt gatagttcac                                                   20

<210> SEQ ID NO 71
<211> LENGTH: 20
<212> TYPE: DNA
<213> ORGANISM: Artificial Sequence
<220> FEATURE:
<223> OTHER INFORMATION: Human CFB reverse primer

<400> SEQUENCE: 71
cagggcagca cttgaaagag                                                   20

<210> SEQ ID NO 72
<211> LENGTH: 20
<212> TYPE: DNA
<213> ORGANISM: Artificial Sequence
<220> FEATURE:
<223> OTHER INFORMATION: Human CSF2 forward primer

<400> SEQUENCE: 72
gggagcatgt gaatgccatc                                                   20

<210> SEQ ID NO 73
<211> LENGTH: 23
<212> TYPE: DNA
<213> ORGANISM: Artificial Sequence
<220> FEATURE:
<223> OTHER INFORMATION: Human CSF2 reverse primer

<400> SEQUENCE: 73
gcagtgtctc tactcaggtt cag                                               23

<210> SEQ ID NO 74
<211> LENGTH: 19
<212> TYPE: DNA
<213> ORGANISM: Artificial Sequence
<220> FEATURE:
<223> OTHER INFORMATION: Human CX3CL1 forward primer

<400> SEQUENCE: 74
accacggtgt gacgaaatg                                                    19

<210> SEQ ID NO 75
<211> LENGTH: 21
<212> TYPE: DNA
<213> ORGANISM: Artificial Sequence
<220> FEATURE:
<223> OTHER INFORMATION: Human CX3CL1 reverse primer

<400> SEQUENCE: 75
ctccaagatg attgcgcgtt t                                                 21

<210> SEQ ID NO 76
<211> LENGTH: 20
<212> TYPE: DNA
<213> ORGANISM: Artificial Sequence
<220> FEATURE:
<223> OTHER INFORMATION: Human CXCL1 forward primer

<400> SEQUENCE: 76
agggaattca ccccaagaac                                                   20

<210> SEQ ID NO 77
```

```
<211> LENGTH: 20
<212> TYPE: DNA
<213> ORGANISM: Artificial Sequence
<220> FEATURE:
<223> OTHER INFORMATION: Human CXCL1 reverse primer

<400> SEQUENCE: 77
actatggggg atgcaggatt                                              20

<210> SEQ ID NO 78
<211> LENGTH: 21
<212> TYPE: DNA
<213> ORGANISM: Artificial Sequence
<220> FEATURE:
<223> OTHER INFORMATION: Human CXCL16 forward primer

<400> SEQUENCE: 78
cagcgtcact ggaagttgtt a                                            21

<210> SEQ ID NO 79
<211> LENGTH: 21
<212> TYPE: DNA
<213> ORGANISM: Artificial Sequence
<220> FEATURE:
<223> OTHER INFORMATION: Human CXCL16 reverse primer

<400> SEQUENCE: 79
caccgatggt aagctctcag g                                            21

<210> SEQ ID NO 80
<211> LENGTH: 21
<212> TYPE: DNA
<213> ORGANISM: Artificial Sequence
<220> FEATURE:
<223> OTHER INFORMATION: Human CXCL3 forward primer

<400> SEQUENCE: 80
ccaaaccgaa gtcatagcca c                                            21

<210> SEQ ID NO 81
<211> LENGTH: 21
<212> TYPE: DNA
<213> ORGANISM: Artificial Sequence
<220> FEATURE:
<223> OTHER INFORMATION: Human CXCL3 reverse primer

<400> SEQUENCE: 81
tgctcccctt gttcagtatc t                                            21

<210> SEQ ID NO 82
<211> LENGTH: 20
<212> TYPE: DNA
<213> ORGANISM: Artificial Sequence
<220> FEATURE:
<223> OTHER INFORMATION: Human CXCL6 forward primer

<400> SEQUENCE: 82
agagctgcgt tgcacttgtt                                              20

<210> SEQ ID NO 83
<211> LENGTH: 23
<212> TYPE: DNA
<213> ORGANISM: Artificial Sequence
<220> FEATURE:
<223> OTHER INFORMATION: Human CXCL6 reverse primer

<400> SEQUENCE: 83
```
gcagtttacc aatcgttttg ggg                                          23

<210> SEQ ID NO 84
<211> LENGTH: 21
<212> TYPE: DNA
<213> ORGANISM: Artificial Sequence
<220> FEATURE:
<223> OTHER INFORMATION: Human EGR1 forward primer

<400> SEQUENCE: 84
acctgaccgc agagtctttt c                                            21

<210> SEQ ID NO 85
<211> LENGTH: 20
<212> TYPE: DNA
<213> ORGANISM: Artificial Sequence
<220> FEATURE:
<223> OTHER INFORMATION: Human EGR1 reverse primer

<400> SEQUENCE: 85
gccagtatag gtgatggggg                                              20

<210> SEQ ID NO 86
<211> LENGTH: 22
<212> TYPE: DNA
<213> ORGANISM: Artificial Sequence
<220> FEATURE:
<223> OTHER INFORMATION: Human EGR2 forward primer

<400> SEQUENCE: 86
atcccagtaa ctctcagtgg tt                                           22

<210> SEQ ID NO 87
<211> LENGTH: 20
<212> TYPE: DNA
<213> ORGANISM: Artificial Sequence
<220> FEATURE:
<223> OTHER INFORMATION: Human EGR2 reverse primer

<400> SEQUENCE: 87
ctccaccggg tagatgttgt                                              20

<210> SEQ ID NO 88
<211> LENGTH: 19
<212> TYPE: DNA
<213> ORGANISM: Artificial Sequence
<220> FEATURE:
<223> OTHER INFORMATION: Human EGR3 forward primer

<400> SEQUENCE: 88
gcgacctcta ctcagagcc                                               19

<210> SEQ ID NO 89
<211> LENGTH: 21
<212> TYPE: DNA
<213> ORGANISM: Artificial Sequence
<220> FEATURE:
<223> OTHER INFORMATION: Human EGR3 reverse primer

<400> SEQUENCE: 89
atggggaaga gattgctgtc c                                            21

<210> SEQ ID NO 90
<211> LENGTH: 19
<212> TYPE: DNA

<213> ORGANISM: Artificial Sequence
<220> FEATURE:
<223> OTHER INFORMATION: Human EGR4 forward primer

<400> SEQUENCE: 90
agcgagtttt ccgaacccg                                        19

<210> SEQ ID NO 91
<211> LENGTH: 20
<212> TYPE: DNA
<213> ORGANISM: Artificial Sequence
<220> FEATURE:
<223> OTHER INFORMATION: Human EGR4 reverse primer

<400> SEQUENCE: 91
gagtcggcta agtccccact                                       20

<210> SEQ ID NO 92
<211> LENGTH: 21
<212> TYPE: DNA
<213> ORGANISM: Artificial Sequence
<220> FEATURE:
<223> OTHER INFORMATION: Human IL1R1 forward primer

<400> SEQUENCE: 92
acattgtgct ttggtacagg g                                     21

<210> SEQ ID NO 93
<211> LENGTH: 22
<212> TYPE: DNA
<213> ORGANISM: Artificial Sequence
<220> FEATURE:
<223> OTHER INFORMATION: Human IL1R1 reverse primer

<400> SEQUENCE: 93
ccccaacagt ctttggatac ag                                    22

<210> SEQ ID NO 94
<211> LENGTH: 21
<212> TYPE: DNA
<213> ORGANISM: Artificial Sequence
<220> FEATURE:
<223> OTHER INFORMATION: Human LIF forward primer

<400> SEQUENCE: 94
gtaccgcata gtcgtgtacc t                                     21

<210> SEQ ID NO 95
<211> LENGTH: 20
<212> TYPE: DNA
<213> ORGANISM: Artificial Sequence
<220> FEATURE:
<223> OTHER INFORMATION: Human LIF reverse primer

<400> SEQUENCE: 95
cacagcacgt tgctaaggag                                       20

<210> SEQ ID NO 96
<211> LENGTH: 21
<212> TYPE: DNA
<213> ORGANISM: Artificial Sequence
<220> FEATURE:
<223> OTHER INFORMATION: Human MMP11 forward primer

<400> SEQUENCE: 96
gaggccctaa aggtatggag c                                     21

<210> SEQ ID NO 97
<211> LENGTH: 20
<212> TYPE: DNA
<213> ORGANISM: Artificial Sequence
<220> FEATURE:
<223> OTHER INFORMATION: Human MMP11 reverse primer

<400> SEQUENCE: 97
cccttctcgg tgagtcttgg                                               20

<210> SEQ ID NO 98
<211> LENGTH: 19
<212> TYPE: DNA
<213> ORGANISM: Artificial Sequence
<220> FEATURE:
<223> OTHER INFORMATION: Human PLAU forward primer

<400> SEQUENCE: 98
gtgagcgact ccaaaggca                                                19

<210> SEQ ID NO 99
<211> LENGTH: 21
<212> TYPE: DNA
<213> ORGANISM: Artificial Sequence
<220> FEATURE:
<223> OTHER INFORMATION: Human PLAU reverse primer

<400> SEQUENCE: 99
gcagttgcac cagtgaatgt t                                             21

<210> SEQ ID NO 100
<211> LENGTH: 21
<212> TYPE: DNA
<213> ORGANISM: Artificial Sequence
<220> FEATURE:
<223> OTHER INFORMATION: Human PTGS2 forward primer

<400> SEQUENCE: 100
gtgcaacact tgagtggcta t                                             21

<210> SEQ ID NO 101
<211> LENGTH: 22
<212> TYPE: DNA
<213> ORGANISM: Artificial Sequence
<220> FEATURE:
<223> OTHER INFORMATION: Human PTGS2 reverse primer

<400> SEQUENCE: 101
agcaatttgc ctggtgaatg at                                            22

<210> SEQ ID NO 102
<211> LENGTH: 22
<212> TYPE: DNA
<213> ORGANISM: Artificial Sequence
<220> FEATURE:
<223> OTHER INFORMATION: Human S1PR1 forward primer

<400> SEQUENCE: 102
cttgctgacc atttggaaaa cc                                            22

<210> SEQ ID NO 103
<211> LENGTH: 20
<212> TYPE: DNA
<213> ORGANISM: Artificial Sequence
<220> FEATURE:

<223> OTHER INFORMATION: Human S1PR1 reverse primer

<400> SEQUENCE: 103
ctgtgtaggc tactcctgcc                                    20

<210> SEQ ID NO 104
<211> LENGTH: 19
<212> TYPE: DNA
<213> ORGANISM: Artificial Sequence
<220> FEATURE:
<223> OTHER INFORMATION: Human SDC4 forward primer

<400> SEQUENCE: 104
gctcttcgta ggcggagtc                                     19

<210> SEQ ID NO 105
<211> LENGTH: 20
<212> TYPE: DNA
<213> ORGANISM: Artificial Sequence
<220> FEATURE:
<223> OTHER INFORMATION: Human SDC4 reverse primer

<400> SEQUENCE: 105
cctcatcgtc tggtagggct                                    20

<210> SEQ ID NO 106
<211> LENGTH: 19
<212> TYPE: DNA
<213> ORGANISM: Artificial Sequence
<220> FEATURE:
<223> OTHER INFORMATION: Human SELE forward primer

<400> SEQUENCE: 106
aatccagcca atgggttcg                                     19

<210> SEQ ID NO 107
<211> LENGTH: 24
<212> TYPE: DNA
<213> ORGANISM: Artificial Sequence
<220> FEATURE:
<223> OTHER INFORMATION: Human SELE reverse primer

<400> SEQUENCE: 107
gctcccatta gttcaaatcc ttct                               24

<210> SEQ ID NO 108
<211> LENGTH: 19
<212> TYPE: DNA
<213> ORGANISM: Artificial Sequence
<220> FEATURE:
<223> OTHER INFORMATION: Human SERPINE1 forward primer

<400> SEQUENCE: 108
catcccccat cctacgtgg                                     19

<210> SEQ ID NO 109
<211> LENGTH: 21
<212> TYPE: DNA
<213> ORGANISM: Artificial Sequence
<220> FEATURE:
<223> OTHER INFORMATION: Human SERPINE1 reverse primer

<400> SEQUENCE: 109
ccccataggg tgagaaaacc a                                  21

```
<210> SEQ ID NO 110
<211> LENGTH: 21
<212> TYPE: DNA
<213> ORGANISM: Artificial Sequence
<220> FEATURE:
<223> OTHER INFORMATION: Human TIMP3 forward primer

<400> SEQUENCE: 110
catgtgcagt acatccacac g                                              21

<210> SEQ ID NO 111
<211> LENGTH: 21
<212> TYPE: DNA
<213> ORGANISM: Artificial Sequence
<220> FEATURE:
<223> OTHER INFORMATION: Human TIMP3 reverse primer

<400> SEQUENCE: 111
acatcttgcc atcatagacg c                                              21

<210> SEQ ID NO 112
<211> LENGTH: 21
<212> TYPE: DNA
<213> ORGANISM: Artificial Sequence
<220> FEATURE:
<223> OTHER INFORMATION: Human TNFRSF11B forward primer

<400> SEQUENCE: 112
aagggcgcta ccttgagata g                                              21

<210> SEQ ID NO 113
<211> LENGTH: 22
<212> TYPE: DNA
<213> ORGANISM: Artificial Sequence
<220> FEATURE:
<223> OTHER INFORMATION: Human TNFRSF11B reverse primer

<400> SEQUENCE: 113
gcaaactgta tttcgctctg gg                                             22

<210> SEQ ID NO 114
<211> LENGTH: 19
<212> TYPE: DNA
<213> ORGANISM: Artificial Sequence
<220> FEATURE:
<223> OTHER INFORMATION: Human TRAF1 forward primer

<400> SEQUENCE: 114
ccggcccctg atgagaatg                                                 19

<210> SEQ ID NO 115
<211> LENGTH: 22
<212> TYPE: DNA
<213> ORGANISM: Artificial Sequence
<220> FEATURE:
<223> OTHER INFORMATION: Human TRAF1 reverse primer

<400> SEQUENCE: 115
ttcctgggct tatagactgg ag                                             22

<210> SEQ ID NO 116
<211> LENGTH: 21
<212> TYPE: DNA
<213> ORGANISM: Artificial Sequence
<220> FEATURE:
<223> OTHER INFORMATION: Human VCAM1 forward primer
```

```
<400> SEQUENCE: 116
gctgctcaga ttggagactc a                                              21

<210> SEQ ID NO 117
<211> LENGTH: 20
<212> TYPE: DNA
<213> ORGANISM: Artificial Sequence
<220> FEATURE:
<223> OTHER INFORMATION: Human VCAM1 reverse primer

<400> SEQUENCE: 117
cgctcagagg gctgtctatc                                                20

<210> SEQ ID NO 118
<211> LENGTH: 19
<212> TYPE: DNA
<213> ORGANISM: Artificial Sequence
<220> FEATURE:
<223> OTHER INFORMATION: Human GAPDH forward primer

<400> SEQUENCE: 118
atggggaagg tgaaggtcg                                                 19

<210> SEQ ID NO 119
<211> LENGTH: 22
<212> TYPE: DNA
<213> ORGANISM: Artificial Sequence
<220> FEATURE:
<223> OTHER INFORMATION: Human GAPDH reverse primer

<400> SEQUENCE: 119
ggggtcattg atggcaacaa ta                                             22

<210> SEQ ID NO 120
<211> LENGTH: 23
<212> TYPE: RNA
<213> ORGANISM: Artificial Sequence
<220> FEATURE:
<223> OTHER INFORMATION: Human importin-alpha 3 3'-UTR site 1

<400> SEQUENCE: 120
cuugcuauga agcagugugu gaa                                            23

<210> SEQ ID NO 121
<211> LENGTH: 23
<212> TYPE: RNA
<213> ORGANISM: Artificial Sequence
<220> FEATURE:
<223> OTHER INFORMATION: Human importin-alpha 3 3'-UTR site 2

<400> SEQUENCE: 121
auggacaaug uugaaugaau guc                                            23

<210> SEQ ID NO 122
<211> LENGTH: 23
<212> TYPE: RNA
<213> ORGANISM: Artificial Sequence
<220> FEATURE:
<223> OTHER INFORMATION: Human importin-alpha 3 3'-UTR site 3

<400> SEQUENCE: 122
cuguguacga gagcgugguu gug                                            23

<210> SEQ ID NO 123
<211> LENGTH: 23
```

```
<212> TYPE: RNA
<213> ORGANISM: Artificial Sequence
<220> FEATURE:
<223> OTHER INFORMATION: Human importin-alpha 3 3'-UTR site 4

<400> SEQUENCE: 123
ugguuuacuc ugcagccugu guu                                              23

<210> SEQ ID NO 124
<211> LENGTH: 23
<212> TYPE: RNA
<213> ORGANISM: Artificial Sequence
<220> FEATURE:
<223> OTHER INFORMATION: Human importin-alpha 3 3'-UTR site 5

<400> SEQUENCE: 124
ugcauuugca ccagaugaau guu                                              23

<210> SEQ ID NO 125
<211> LENGTH: 23
<212> TYPE: RNA
<213> ORGANISM: Artificial Sequence
<220> FEATURE:
<223> OTHER INFORMATION: Human importin-alpha 3 3'-UTR site 6

<400> SEQUENCE: 125
uuucccucaa aauagacugu guu                                              23

<210> SEQ ID NO 126
<211> LENGTH: 23
<212> TYPE: RNA
<213> ORGANISM: Artificial Sequence
<220> FEATURE:
<223> OTHER INFORMATION: Human importin-alpha 3 3'-UTR site 6

<400> SEQUENCE: 126
uuucccucaa aauagacugu guu                                              23

<210> SEQ ID NO 127
<211> LENGTH: 23
<212> TYPE: RNA
<213> ORGANISM: Artificial Sequence
<220> FEATURE:
<223> OTHER INFORMATION: Human importin-alpha 3 3'-UTR site 7

<400> SEQUENCE: 127
auaccgugcu guguuuaaau guu                                              23

<210> SEQ ID NO 128
<211> LENGTH: 23
<212> TYPE: RNA
<213> ORGANISM: Artificial Sequence
<220> FEATURE:
<223> OTHER INFORMATION: Human importin-alpha 3 3'-UTR site 8

<400> SEQUENCE: 128
cuuccccuuu gagcacaagu guu                                              23

<210> SEQ ID NO 129
<211> LENGTH: 23
<212> TYPE: RNA
<213> ORGANISM: Artificial Sequence
<220> FEATURE:
<223> OTHER INFORMATION: Human importin-alpha 3 3'-UTR mutated site 1

<400> SEQUENCE: 129
```

```
cuugcuauga uaaagcuucu gaa                                    23

<210> SEQ ID NO 130
<211> LENGTH: 23
<212> TYPE: RNA
<213> ORGANISM: Artificial Sequence
<220> FEATURE:
<223> OTHER INFORMATION: Human importin-alpha 3 3'-UTR mutated site 2

<400> SEQUENCE: 130
aggcugaauc uugccaacau cac                                    23
```

METHODS OF TREATING VASCULAR INFLAMMATORY DISORDERS

CROSS-REFERENCE TO RELATED APPLICATIONS

This application is a U.S. National Phase Application under 35 U.S.C. §371 of International Application No. PCT/US2011/027772, filed on Mar. 9, 2011, which claims the benefit of U.S. Provisional Patent Application No. 61/313,274, filed on Mar. 12, 2010, the contents of each of which are hereby incorporated by reference in their entireties.

TECHNICAL FIELD

Described herein are methods for treating or delaying the onset of a vascular inflammatory disease in a subject and decreasing nuclear factor-KB (NF-κB) signaling in a cell (e.g., an endothelial cell).

BACKGROUND

The vascular endothelium represents a critical interface between blood and all tissues. Endothelial dysfunction contributes to the development of both acute inflammatory disease states, such as endotoxemia and sepsis, and chronic inflammatory disease states, such as atherosclerosis, diabetes, rheumatoid arthritis, and inflammatory bowel disease (Aird, *Blood* 101:3765-3777, 2003; Aird, *Lancet* 365:63-78, 2007; Baker et al., *Cell Metab.* 13:11-22, 2011; Gareus et al., *Cell Metab.* 8:372-383, 2008; Guerci et al., *Diabetes Metab.* 27:436-477, 2001; Hansson and Libby, *Nat. Rev. Immunol.* 6:508-519, 2006; Khan et al., *Nat. Rev. Rheumatol.* 6: 253-261, 2010; Roifman et al., *Clin. Gastroenterol. Hepatol.* 7:175-182, 2009). In response to inflammatory stimuli, the vascular endothelium expresses a number of adhesion molecules that play key roles in the recruitment of leukocytes to sites of inflammation (Ley et al., *Nat. Rev. Immunol.* 7:678-689, 2007; Pober and Sessa, *J. Immunol.* 138:3319-3324, 2007). In particular, vascular cell adhesion molecule 1 (VCAM-1), E-selectin, and intercellular adhesion molecule 1 (ICAM-1) mediate early leukocyte attachment and rolling events. An inflammatory response within tissues is subsequently generated after events such as firm adhesion and transmigration occur (Ley et al., *Nat. Rev. Immunol.* 7:678-689, 2007). Clinical studies have found that the soluble forms of these adhesion molecules are increased in patients experiencing vascular inflammatory disease (Shapiro et al., *Crit. Care* 14:R182, 2010; Xu et al., *Int. J. Cardiol.* 64:253-258, 1998).

SUMMARY

The present invention is based, at least in part, on the surprising discovery that overexpression of miR-181b in endothelial cells inhibited TNF-α-induced NF-κB-mediated up-regulation of vascular cell adhesion molecule-1 (VCAM-1), E-selectin, and intracellular adhesion molecule-1 (ICAM-1) expression, inhibited leukocyte adhesion to activated endothelial cell monolayers, and suppressed TNF-α-induced NF-κB-mediated VCAM-1 and E-selectin expression in vascular endothelium in vivo. In view of the discovery that miR-181b inhibits NF-κB signaling, methods of treating diseases caused or mediated by NF-κB signaling (e.g., vascular inflammatory diseases) and methods of inhibiting NF-κB signaling in a cell (e.g., an endothelial cell) are provided.

Accordingly, provided herein are methods of treating or delaying the onset of a vascular inflammatory disease (e.g., lung inflammation (e.g., acute lung injury, such as sepsis-induced acute lung injury), asthma, atherosclerosis, arthritis, stroke, inflammatory bowel syndrome, cardiovascular disease, myocardial infarction, coronary artery disease, heart failure, ulcerative colitis, Crohn's disease, and peripheral artery disease) including administering to the subject a therapeutically effective amount of a nucleic acid containing all or a part (e.g., 5, 6, 7, 8, 9, 10, 11, 12, 13, 14, 15, 16, 17, 18, 19, 20, 21, 22, or 23 nucleotides) of the sequence of miR-181b (SEQ ID NO: 1). In some embodiments of these methods, the vascular inflammatory disease is an acute vascular inflammatory disease or a chronic vascular inflammatory disease.

In some embodiments of the methods described herein, the nucleic acid is administered orally, intramuscularly, subcutaneously, arterially, intravenously, or by inhalation. In some embodiments of these methods, the subject is administered one dose or multiple doses (e.g., at least two, three, four, five, six, seven, eight, nine, or ten doses) of the nucleic acid. In some embodiments, the nucleic acid is administered continuously over a treatment period (e.g., at least 5 minutes, 10 minutes, 20 minutes, 30 minutes, 1 hour, 2 hours, 3 hours, 4 hours, 5 hours, 6 hours, 10 hours, 18 hours, 24 hours, 48 hours, or 1 week).

In some embodiments of the methods described herein, the administering results in a decrease (e.g., a significant (as used herein, the term "significant" means statistically significant) decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) in leukocyte adhesion to the subject's endothelium or a decrease (e.g., a significant decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) in leukocyte extravasion of the subject's endothelium as compared to a control subject (e.g., a healthy or asymptomatic subject, a subject not having been diagnosed with or not presenting with one or more symptoms of a vascular inflammatory disorder, or a subject diagnosed with or presenting with one or more symptoms of a vascular inflammatory disorder) not administered the nucleic acid. In some embodiments of the methods described herein, the administering results in a decrease (e.g., a significant decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) in the expression (protein or nucleic acid) of VCAM-1, E-selectin, or ICAM-1 in the subject's endothelium as compared to a control subject (e.g., a healthy or asymptomatic subject, a subject not having been diagnosed with or not presenting with one or more symptoms of a vascular inflammatory disorder, or a subject diagnosed with or presenting with one or more symptoms of a vascular inflammatory disorder) not administered the nucleic acid.

Also provided are methods of decreasing (e.g., a significant decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) nuclear factor-KB (NF-κB) signaling in an endothelial cell (e.g., an endothelial cell in a subject or an endothelial cell in vitro or ex vivo) including administering to the endothelial cell a nucleic acid containing all or a part (e.g., 5, 6, 7, 8, 9, 10, 11, 12, 13, 14, 15, 16, 17, 18, 19, 20, 21, 22, or 23 nucleotides) of the sequence of miR-181b (SEQ ID NO: 1). In some embodiments, the administering results in a decrease (e.g., a significant decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) in the expression (protein or mRNA) of importin-α3 in the endothelial cell as compared to an endothelial cell not administered the nucleic acid or administered a control nucleic acid (e.g., a scrambled non-specific sequence). In some embodiments, the administering results in a decrease (e.g., a significant decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) in the nuclear import of the p65 and/or p50 subunit of NF-κB into the nucleus of the endothelial cell as compared to an endothelial cell not administered the nucleic acid or administered a control nucleic acid (e.g., a scrambled non-specific sequence). In some embodiments, the administering results in a decrease (e.g., a significant decrease, such as a decrease of at least 5%, 10%, 15%, 20%, 25%, 30%, 35%, 40%, 45%, 50%, 55%, 60%, 65%, 70%, 75%, 80%, 85%, 90%, or 95%) in the expression (protein or mRNA) of one or more (e.g., one, two, or three) of VCAM-1, E-selectin, or ICAM-1 in the endothelial cell as compared to an endothelial cell not administered the nucleic acid or administered a control nucleic acid (e.g., a scrambled non-specific sequence).

In some embodiments, the endothelial cell is in a subject and the nucleic acid is administered to the subject orally, intramuscularly, subcutaneously, arterially, intravenously, or by inhalation.

In any of the methods described herein, the nucleic acid can contain the sequence of SEQ ID NO: 2 or SEQ ID NO: 3. In any of the methods described herein, the nucleic acid can be modified or conjugated to one or more (e.g., two or three) of a polymer (e.g., a polyethylene glycol or a polyalkylene glycol), a peptide (e.g., a RGD peptide or a collagen (e.g., type I telocollagen)), and a polysaccharide (e.g., a β-1,3-glycan).

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T) (or uracil (U) in the case of RNA), and guanine (G) forms a base pair with cytosine (C)) under suitable conditions of stringency. (See, e.g., Wahl, G. M. and S. L. Berger, *Methods Enzymol.* 152:399, 1987; Kimmel, A. R., *Methods Enzymol.* 152:507, 1987). For the purposes of the present methods, the nucleic acid need not be complementary to the entire target sequence (e.g., a sequence within the importin-α3 mRNA, such as a sequence within the 3'-UTR of the importin-3α mRNA), only enough of it to provide specific inhibition; for example in some embodiments the sequence is 100% complementary to at least 5-23, 5-15, or 5-10 contiguous nucleotides in the 3'-UTR of a importin-3α mRNA (e.g., site 1 or site 2 in the 3'-UTR of importin-α3 shown in FIG. 8A). Further details are provided below.

As used herein, an "antisense oligonucleotide" refers to a nucleic acid sequence that is complementary to a DNA or RNA sequence, such a sequence present in importin-α3 (e.g., a sequence present in the 3'-UTR of importin-α3 mRNA, such as site 1 or site 2 in the 3'-UTR of importin-α3 mRNA shown in FIG. 8A).

By the term "treating" is meant a reduction in the severity, duration, or frequency of one or more (e.g., two, three, four, five, or six) symptoms of a disease (e.g., a vascular inflammatory disease), an elimination of one or more (e.g., two, three, four, five, or six) symptoms of a disease (e.g., a vascular inflammatory disease), and/or a delay in the onset of one or more (e.g., two, three, four, five, or six) symptoms of a disease (e.g., a vascular inflammatory disease) in a subject (e.g., a subject diagnosed as having a vascular inflammatory disease or a subject identified as being at risk of developing a vascular inflammatory disease). A delay in the onset of one or more symptoms of a disease (e.g., a vascular inflammatory disease) in a subject administered a nucleic acid containing all or a part of the sequence of SEQ ID NO: 1 may be compared to the development of the same symptoms in a subject with the same disease (e.g., same vascular inflammatory disease) that is not administered the nucleic acid.

By the term "vascular inflammatory disease" is a disease state that involves at one or more (e.g., one, two, or three) stages (e.g., an early stage (e.g., before the development of one or more symptoms of a vascular inflammatory disease or before diagnosis by a health care professional), an intermediate stage (e.g., following the development of one or more symptoms of a vascular inflammatory disease or following diagnosis by a health care professional), or a late stage (e.g., following the manifestation of one or more severe symptoms of a vascular inflammatory disease that require admission into a health care facility (e.g., a hospital or intensive care unit)) in the pathobiology of the disease one or more (e.g., one, two, three, or four) of: endothelial cell activation, leukocyte adhesion to the endothelium, leukocyte extravasion of the endothelium, and increased (e.g., a significant increase, such as by at least 5%, 10%, 15%, 20%, 25%, 30%, 35%, 40%, 45%, 50%, 55%, 60%, 70%, 80%, 90%, or 95%) expression (protein or mRNA) of one or more of VCAM-1, E-selectin, or ICAM-1 in the endothelium compared to a control subject (e.g., a healthy or asymptomatic subject, a subject not diagnosed with a vascular inflammatory disease, a subject not presenting with one or more symptoms of a vascular inflammatory disease, the same subject prior to the development of one or more symptoms of a vascular inflammatory disease, the same subject prior to diagnosis with a vascular inflammatory disease, or the same subject at an earlier stage in the vascular inflammatory disease).

By the term "acute vascular inflammatory disease" is meant a vascular inflammatory disease that is typified by an initial response of the body to harmful stimuli (e.g., bacterial infection or tissue injury) which results in the increased movement of both plasma and leukocytes (e.g., granulocytes) from the blood into the injured tissue(s).

By the term "chronic vascular inflammatory disease" is meant a vascular inflammatory disease that is characterized by a prolonged period (e.g., at least 1 week, 2 weeks, one month, two months, three months, four months, five months, six months, 1 year, 2 years, 3 years, 4 years, or 5 years) of inflammation in one or more tissues (e.g., two, three, four, of five) in a subject.

By the term "acute lung injury" is meant an inflammatory disease in the lung that results in a decrease in respiratory function. Acute lung injury is often characterized by one or more (e.g., two, three, or four) of: decreased partial pressure of oxygen in the blood, pulmonary edema, decreased lung compliance, and capillary leakage. Acute lung injury may be caused by local or systemic inflammation. For example, acute lung injury may be induced by sepsis ("sepsis-induced acute lung injury.")

By the term "delaying the onset" is meant reducing (e.g., a significant decrease, such as by at least 5%, 10%, 15%, 20%, 25%, 30%, 35%, 40%, 45%, 50%, 55%, 60%, 70%, 80%, 90%, or 95%) the rate of development or the development of one or more (e.g., at least two, three, four, or five) symptoms of disease (e.g., a vascular inflammatory disease) in a subject by administering a therapeutic treatment (e.g., a nucleic acid containing all or a part of the sequence of SEQ ID NO: 1) compared to a control subject (e.g., a subject not receiving the therapeutic treatment or the same subject prior to administration of the therapeutic treatment).

By the phrase "a part of the sequence of miR-181b" or "a part of the sequence of SEQ ID NO: 1" is meant 5, 6, 7, 8, 9, 10, 11, 12, 13, 14, 15, 16, 17, 18, 19, 20, 21, 22, or 23 contiguous nucleotides within the sequence of SEQ ID NO: 1. For example a part of the sequence of miR-181b may be between 5 to 23, 5 to 20, 5 to 15, or 5 to 10 contiguous nucleotides within the sequence of SEQ ID NO: 1. The contiguous sequence does need to start at the 5'-end of the sequence of SEQ ID NO: 1 and may start at nucleotide position 1, 2, 3, 4, 5, 6, 7, 8, 9, 10, 11, 12, 13, 14, 15, 16, 17, or 18 of SEQ ID NO: 1.

By "therapeutically effective amount" is meant an amount that is sufficient to ameliorate or treat one or more (e.g., two, three, four, or five) symptoms of a vascular inflammatory disease in a subject or delay the onset of one or more (e.g., two, three, four, or five symptoms) of a vascular inflammatory disease in a subject.

By "symptom of a vascular inflammatory disease" is a meant a physical manifestation of a vascular inflammatory disease that can be assessed or measured by a health care professional (e.g., a physician, a nurse, a physician's assistant, or a laboratory technician). Non-limiting examples of symptoms of a vascular inflammatory disease include: pain, redness, swelling, vasodilation, increased vascular permeability, diarrhea, nausea, vomiting, abdominal cramps, abdominal pain, blood in stool, fever, ulcers, reduced appetite, weight loss, fatigue, eye inflammation, chest pain or discomfort, shortness of breath, dizziness, increased heart rate, upper body pain, stomach pain, anxiety, sweating, leg cramping, leg numbness or weakness, sores on legs and toes, change in color of legs, hair loss of slower hair growth on feet and legs, shiny skin on legs, weak pulse in legs or feet, erectile dysfunction, persistent cough or wheezing, white or pink blood-tinged phlegm, weight gain from fluid retention, difficulty concentrating, heart palpitations, trouble sleeping caused by shortness of breath, audible whistling or wheezing sound when exhaling, bouts of coughing or wheezing, numbness or weakness in your arms or legs, difficulty speaking or slurred speech, drooping muscles in the face, stiffness in joints, decreased range of motion, trouble with seeing in one or both eyes, headache, labored and unusually rapid breathing, low blood pressure, and confusion.

"RNA" is a molecule comprising at least one or more ribonucleotide residues. A "ribonucleotide" is a nucleotide with a hydroxyl group at the 2' position of a beta-D-ribofuranose moiety. The term RNA, as used herein, includes double-stranded RNA, single-stranded RNA, isolated RNA, such as partially purified RNA, essentially pure RNA, synthetic RNA, recombinantly produced RNA, as well as altered RNA that differs from naturally occurring RNA by the addition, deletion, substitution, and/or alteration of one or more nucleotides. Nucleotides of the RNA molecules can also comprise non-standard nucleotides, such as non-naturally occurring nucleotides, chemically-synthesized nucleotides, or deoxynucleotides.

A "microRNA" (miRNA) is a single-stranded RNA molecule of about 21-23 nts in length. In general, miRNAs regulate gene expression. miRNAs are encoded by genes from whose DNA they are transcribed, but miRNAs are not translated into protein. Each primary miRNA transcript is processed into a short stem-loop structure before undergoing further processing into a functional miRNA. Mature miRNA molecules are partially complementary to one or more messenger RNA (mRNA) molecules, and their main function is to down-regulate gene expression. Exemplary mature miRNAs contain all or a part of the sequence of miR-181b (SEQ ID NO: 1). Exemplary precursor miRNAs contain the sequence of SEQ ID NO: 2 or SEQ ID NO: 3. Some examples of miRNAs target the 3'-UTR of an importin-α3 mRNA (e.g., site 1 and site 2 of the 3'-UTR of an importin-α3 mRNA as shown in FIG. 8A).

By "miR-181b" is meant a nucleic acid molecule containing a sequence of SEQ ID NO: 1. For example, the term includes precursor miRNA molecules containing a sequence of SEQ ID NO: 2 or SEQ ID NO: 3. By "mature miR-181b" is meant a nucleic acid molecule having the sequence of SEQ ID NO: 1.

As used herein "an interfering RNA" refers to any double stranded or single stranded RNA sequence capable, either directly or indirectly, of inhibiting or down-regulating gene expression by mediating RNA interference. Interfering RNA includes, but is not limited to, small interfering RNA ("siRNA") and small hairpin RNA ("shRNA"). "RNA interference" refers to the selective degradation of a sequence-compatible messenger RNA transcript (e.g., an importin-α3 mRNA). An example of an interfering RNA is a nucleic acid containing all or a part of the sequence of miR-181b (SEQ ID NO: 1). In additional examples, an interfering RNA is a nucleic acid containing the sequence of SEQ ID NO: 2 or SEQ ID NO: 3, or targets the 3'-UTR of an importin-α3 mRNA (e.g., site 1 or site 2 of the 3'-UTR of an importin-α3 mRNA as shown in FIG. 8A).

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family. In some examples, an shRNA is a nucleic acid containing all or a part of the sequence of miR-181b (SEQ ID NO: 1), SEQ ID NO: 2, or SEQ ID NO: 3. In additional examples, an shRNA targets the 3'-UTR of an importin-α3 mRNA (e.g., site 1 or site 2 of the 3'-UTR of an importin-α3 mRNA as shown in FIG. 8A).

A "small interfering RNA" or "siRNA" as used herein refers to any small RNA molecule capable of inhibiting or down-regulating gene expression by mediating RNA interference in a sequence specific manner. The small RNA can be, for example, about 18 to 21 nucleotides long. An siRNA can contain all or a part of the sequence of SEQ ID NO: 1. In additional examples, an siRNA can target the 3'-UTR of an importin-α3 mRNA (e.g., site 1 or site 2 of the 3'-UTR of an importin-α3 mRNA as shown in FIG. 8A).

A "subject" is a vertebrate, including any member of the class mammalia, including humans, domestic and farm animals, and zoo, sports or pet animals, such as mouse, rabbit, pig, sheep, goat, cattle, and higher primates. In preferred embodiments, the subject is a human.

As used herein, a "vector" or "expression vector" is a nucleic acid-based delivery vehicle containing regulatory sequences and a gene of interest, which can be used to transfer its contents into a cell. For example, the vector may be used to express a nucleic acid containing all or a part of miR-181b (SEQ ID NO: 1) in a cell.

By the term "nuclear factor-KB signaling" or "NF-κB signaling" is meant the multiple signaling pathways within a cell that result in the translocation of NF-κB (e.g., translocation of the p65 and/or p50 subunit of NF-κB) into the nucleus and the increased transcription of one or more (e.g., at least two, three, four, or five) NF-κB-regulated genes. In the cytoplasm, NF-κB is complexed with its inhibitor IκB. Upstream signaling pathways activate an IκB kinase (IKK) complex that results in IKK-mediated phosphorylation-induced proteasomal degradation of the IκB inhibitor. The degradation of IκB allows NF-κB to translocate to the nucleus and induce transcription by binding to specific gene promoters. As described herein, NF-κB signaling plays a role or has been implicated for a role in several disease states (e.g., vascular inflammatory diseases).

By the term "vascular cell adhesion molecule-1" or "VCAM-1" is meant a protein that is substantially identical (e.g., at least 80%, 85%, 90%, 95%, 96%, 97%, 98%, 99%, or 100%) to NCBI Accession No. P19320; NP_001186763.1; NP_542413.1; NP_001069.1; EAW72949.1; AAA61269.1; AAA51917.1; AAA61270.1; AAM96190.1; AAH85003.1; AAH68490.2; or AAH17276.3, or a nucleic acid (e.g., an mRNA) that is substantially identical (e.g., at least 80%, 85%, 90%, 95%, 96%, 97%, 98%, 99%, or 100%) to NCBI Accession No. NM_001199834.1; NM_001078.3; NM_080682.2; M60335.1; M30257.1; BC085003.1; BC068490.1; BC017276.2; AK223266.1; or X53051.1. Methods for measuring the VCAM-1 protein and mRNA are described herein and are well known in the art.

By the term "E-selectin" is meant a protein that is substantially identical (e.g., at least 80%, 85%, 90%, 95%, 96%, 97%, 98%, 99%, or 100%) to NCBI Accession No. NP_000441.2 or AAQ67702.1, or a nucleic acid (e.g., an mRNA) that is substantially identical (e.g., at least 80%, 85%, 90%, 95%, 96%, 97%, 98%, 99%, or 100%) to NCBI Accession No. NM_001145667.1 or NM_000450.2. Methods for measuring the E-selectin protein and mRNA are described herein and are well known in the art.

By the term "intercellular adhesion molecule-1" or "ICAM-1" is meant a protein that is substantially identical (e.g., at least 80%, 85%, 90%, 95%, 96%, 97%, 98%, 99%, or 100%) to NCBI Accession No. CAA41977.1, NP_000192.2, P05362.2, or CAA30051.1, or a nucleic acid (e.g., an mRNA) that is substantially identical (e.g., at least 80%, 85%, 90%, 95%, 96%, 97%, 98%, 99%, or 100%) to NCBI Accession No. NG_012083.1, NM_000201.2, J03132.1, or BC015969.2. Methods for measuring the ICAM-1 protein and mRNA are described herein and are well known in the art.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a bar graph showing the expression of miR-181b in response to TNF-α (10 ng/ml) treatment in HUVECs. The level of miR-181b was detected by real-time qPCR. The values represent mean±SD. *P<0.01.

FIG. 1B is a bar graph showing that miR-181b is the dominant member of the miR-181 family expressed in HUVECs. The levels of miR-181a, miR-181b, and miR-181c were detected by real-time qPCR. The values represent mean±SD. In FIGS. 1A and 1B, the results represent one out of two independently performed experiments with similar outcomes.

FIG. 1C shows the results of Western blot analysis of VCAM-1, E-selectin, and ICAM-1 protein levels in HUVECs transfected with miRNA negative control (NS-m) or miR-181b mimics (181b-m), miRNA inhibitor negative control (NS-i), or miR-181b inhibitor (181b-i), respectively, after treatment with 10 ng/ml TNF-α for 8 hours (h). Densitometry was performed and fold-change of protein expression after normalization to β-actin expression is shown below each corresponding band. The value for the NS-m or NS-i group was considered to be 1. Representative images of at least three experiments are shown.

FIG. 1D is a set of six bar graphs showing the results of real-time qPCR analysis of VCAM-1 (top row), E-selectin (middle row), and ICAM-1 (bottom row) mRNA levels in HUVECs transfected with miRNA negative control (NS-m) or miR-181b mimics (181b-m), miRNA inhibitor negative control (NS-i), or miR-181b inhibitor (181b-i), respectively, after treatment with 10 ng/ml TNF-α for the indicated times. The results represent one out of three independently performed experiments with similar outcomes. Values represent mean±SD. #P<0.05 and *P<0.01.

FIG. 1E is a set of six bar graphs showing the results of ELISA analysis of elaborated VCAM-1 (top row), E-selectin (middle row), and ICAM-1 (bottom row) protein levels in cell culture medium 16 h after TNF-α (10 ng/ml) treatment. HUVECs were transfected as indicated in FIG. 1A. #P<0.05 and *P<0.01. The values represent mean±SD, n=3.

FIG. 1F is a set of six photoimages and two bar graphs showing that miR-181b regulates the adhesion of THP-1 cells to TNF-α activated HUVECs. Photoimages of THP-1 cells adhering to HUVECs transfected with miRNA negative control (NS-m) (upper and lower far left panels) or miR-181b mimics (181b-m) (upper and lower middle left panels), miRNA inhibitor negative control (NS-i) (upper and lower middle right panels), or miR-181b inhibitor (181b-i) (upper and lower far right panels), respectively, with (bottom panels) or without (upper panels) 10 ng/ml TNF-α treatment for 4 h are shown. Results represent the mean±SD from three independent experiments. *P<0.01, miRNA negative control vs. miR-181b (left bar graph), or miRNA inhibitor negative control vs. miR-181b inhibitor (right bar graph). Bars: 100 μm.

FIG. 2A is Western blot of VCAM-1 protein levels in HUVECs transfected with miRNA negative control (NS-m) or miR-181b mimics (181b-m), respectively, and treated with increasing doses of LPS (serotype O26:B6) for 16 h. Densitometry was performed and fold-changes of protein expression after normalization to β-actin expression are shown in a bar graph in FIG. 2B. Data represent mean±SD from two independent experiments. *P<0.05.

FIG. 2C is three bar graph showing data from an experiment where HUVECs were transfected as in FIG. 2A, and treated with LPS for 6 h. Real-time qPCR analysis of VCAM-1 (left), E-selectin (center), and ICAM-1 (right) mRNA levels was performed. Values represent mean±SD, n=3. *P<0.05.

FIG. 2D is a bar graph showing that miR-181b does not affect the 3'-UTR activity of the VCAM-1 gene. Relative luciferase activity of lysates from HUVECs transfected with luciferase VCAM-1 3'-UTR construct in the presence of miRNA negative control (NS-m) or miR-181b mimics (181b-m) at 10 nM or 50 nM, respectively, is shown. Values represent mean±SD, n=3.

FIG. 2E is a Western blot of VCAM-1 in HUVECs transfected with either miRNA negative control (NS-m), miR-181b mimics (181b-m), or miR-181a mimics (181a-m) at 0.2, 2, 10, or 20 nM concentrations and treated with 10 ng/ml TNF-α for 8 h.

FIGS. 3A-E is a Western blot, four bar graphs, and nine photomicrographs that show that miR-181b represses TNF-α-induced pro-inflammatory gene expression in vivo. FIG. 3A is a Western blot from an experiment where mice were intravenously injected with vehicle, miRNA negative control (NS-m), or miR-181b mimics (181b-m). Twenty-four hours later, mice were treated with or without TNF-α for 4 h, and lungs were harvested for Western blot analysis of VCAM-1 protein levels. Densitometry was performed and fold-change of protein expression after normalization to β-actin expression was quantified. The value for the vehicle group was considered to be 1. *P<0.05.

FIG. 3B is bar graph showing data from experiments carried out as described in FIG. 3A, where real-time qPCR analysis of VCAM-1 mRNA levels in the indicated tissues was performed. *P<0.05.

FIG. 3C is a set of nine photomicrographs showing VCAM-1 staining of lung and aorta sections. Mice treated with vehicle in the absence of TNF-α are shown in the top panels, mice treated with the miRNA negative control (NS-m) and TNF-α are shown in the middle panels, and mice treated with miR-181b mimics (181b-m) are shown in the bottom panels. The middle panels represent an enlargement of the field shown in the left panels. Mice were treated as in FIG. 3A. Bars: 25 µm.

FIG. 3D is a bar graph showing the quantification of VCAM-1 staining in lung endothelium. *P<0.05.

FIG. 3E is a bar graph showing the quantification of VCAM-1 staining in aorta endothelium. *P<0.05. In FIGS. 3A-E, the vehicle group was 3 mice, the NS-m group was 5 mice, and the 181b-m group was 5 mice. The data represent mean±SEM.

FIGS. 4A-C is three bar graphs that show that miR-181b represses TNF-α-induced pro-inflammatory genes expression in vivo. The data from real-time qPCR analysis of E-selectin (bar graph in FIG. 4A) or ICAM-1 (bar graph in FIG. 4B) mRNA levels in tissues harvested from mice injected with vehicle (n=3 mice), miRNA negative control (NS-m) (n=5 mice), or miR-181b (181b-m) (n=5 mice) with or without TNF-α treatment for 4 h are shown. *P<0.05. The right Y-axis represents the values of E-selectin expression in liver. Data represent mean±SD.

FIG. 4C is a bar graph showing data from real-time qPCR analysis of miR-181b in intima, media plus adventitia of aorta from mice (n=2) injected with miR negative control or miR-181b. *P<0.01. Data represent mean±SD.

FIG. 5A is four bar graphs of luciferase activity data of reporters containing either the NF-κB concatemer or VCAM-1 promoter in HUVECs transfected with miRNA negative control (NS-m) or miR-181b mimics (upper left and lower left graphs), miRNA inhibitor negative control (NS-i) or miR-181b inhibitor (181b-i) (upper right and lower right graphs) and 12 h after treatment with 10 ng/ml of TNF-α. #P<0.05; *P<0.01. Values represent the mean±SD, n=3.

FIG. 5B is a bar graph showing the nuclear p65 staining in HUVECs transfected with miRNA negative control (NS-m) or miR-181b mimics (181b-m).

FIG. 5C is two Western blots showing that the indicated proteins were detected in cytoplasmic (right blot) or nuclear (left blot) fractions prepared from HUVECs transfected with miRNA negative control or miR-181b mimics, and treated with 10 ng/ml TNF-α for 1 h. Experiments were performed twice. Densitometry was performed and fold-change of p65 and p50 protein expression after normalization is shown below each corresponding band.

FIG. 7A is a Western blot of importin-α1, importin-α3, and importin-α5 protein levels in cells transfected with miRNA negative control (NS-m) or miR-181b mimics (181b-m), respectively, in the absence or presence of 10 ng/ml TNF-α. Representative images from at least four experiments are shown.

FIG. 7B is a bar graph showing the normalized luciferase activity data of a reporter containing the 3'-UTR of importin-α3 mRNA when co-transfected with increasing amounts of pcDNA3.1 empty vector or pcDNA3.1-miR-181b. Values represent mean±SD, n=3. Results shown are from one of two independent experiments with similar outcomes. *P<0.01.

FIG. 7C is a bar graph showing the normalized luciferase activity data of a reporter containing the 3'-UTR of importin-α1, importin-α3, importin-α4, or importin-α5, respectively, when co-transfected with either pcDNA3.1 empty vector or pcDNA3.1-miR-181b. *P<0.01.

FIG. 7D is a bar graph showing the normalized luciferase activity data of a reporter containing the full-length 3'-UTR of importin-α3, individual rna22 algorithm predicted miR-181b binding sites of the 3'UTR of importin-α3, or mutated 181b binding sites. The reporter was co-transfected with either pcDNA3.1 empty vector or pcDNA3.1-miR-181b. *P<0.05. In FIGS. 7C and 7D, the values represent mean±SD from three independent experiments.

FIG. 7E is two bar graphs showing the data from a miRNP-IP analysis for importin-α3 or Smad1 mRNA in HUVECs transfected with miRNA negative control (NS-m) or miR-181b mimics (181b-m). Values represent mean±SD of two independent experiments. *P<0.01.

FIG. 7F is a bar graph of the luciferase activity data of reporters containing the NF-κB concatemer in cells transfected with miRNA negative control (NS-m) or miR-181b mimics (181b-m) in the absence or presence of importin-α3 gene lacking its 3'-UTR. Values represent mean±SD, n=3. *P<0.05.

FIGS. 8A-B is a diagram showing eight predicted miR-181b binding sites and a bar graph showing that miR-181b targets the importin-α3 3'-UTR. FIG. 8A is a diagram of the eight miR-181b binding sites in importin-α3 3'-UTR that were predicted by rna22. The positions of binding sites are indicated as numbers in parentheses. Lines indicate perfect matches, while colons indicate G:U pairs. Nucleotides marked with dots were mutated. The sequences of miR-181b (SEQ ID NO: 1), 3'UTR site 1 (SEQ ID NO: 120), 3'UTR site 2 (SEQ ID NO: 121), 3'UTR site 3 (SEQ ID NO: 122), 3'UTR site 4 (SEQ ID NO: 123), 3' UTR site 5 (SEQ ID NO: 124), 3' UTR site 6 (SEQ ID NO: 125), 3' UTR site 6 (SEQ ID NO: 126), 3' UTR site 7 (SEQ ID NO: 127), 3'UTR site 8 (SEQ ID NO: 128), mutated 3'UTR site 1 (SEQ ID NO: 129), and mutated 3'UTR site 2 (SEQ ID NO: 130) are shown.

FIG. 8B is a bar graph of real-time qPCR data of importin-α3 mRNA levels in HUVECs transfected with miRNA negative control (NS-m) or miR-181b mimics (181b-m).

FIGS. 9A-D is two bar graphs, a Western blot, and a table showing gene expression profiling data from HUVECs transfected with miR-181b and bioinformatic analysis of these data. FIG. 9A is a bar graph showing the relative gene expression of 29 TNF-α regulated genes in HUVECs transfected with miRNA negative control (NS-m) or miR-181b mimics (181b-m), as identified by microarray gene chip assay. Expression is presented as fold-change relative to HUVECs transfected with a miRNA negative control. The data shown are mean±SD, n=4. *P>0.05.

FIG. 9B is a bar graph showing real-time qPCR analysis of the genes listed in FIG. 9A. All genes examined were significantly reduced by over-expression of miR-181b (P<0.05).

FIG. 9C is a Western blot of CX3CL-1, PAI-1, COX-2, and VCAM-1 in HUVECs transfected with miRNA negative control (NS-m) or miR-181b mimics (181b-m). Experiments were performed twice.

FIG. 9D is a table showing the results of the gene set enrichment analysis.

FIG. 10A is a set of fifteen photomicrographs from an experiment where mice were intravenously injected with vehicle (top panels), miRNA negative control (NS-m) (middle panels), or miR-181b mimics (181b-m) (bottom panels). Twenty-four hours later, the mice were treated with or without LPS i.p. (40 mg/kg, serotype O26:B6) for 4 h, and lungs were harvested for histology, then stained for H & E (far left panels), Gr-1 (center panels), CD45 (center left panels), or VCAM-1 (center right panels and far right panels). Bars: 50 µm.

FIG. 10B is a bar graph of lung damage (lung injury score) 4 h after LPS i.p. injection in mice administered vehicle, negative control (NS-m), or miR-181b mimics (181b-m), as described in FIG. 10A. *P<0.05.

FIG. 10C is a bar graph of quantification data of CD45 positive cells. *P<0.05.

FIG. 10D is a bar graph of quantification data of Gr-1 positive cells. *P<0.05.

FIG. 10E is a bar graph of quantification data of VCAM-1 expression. *P<0.05. In FIGS. 10A-10D, four mice were included in each group, and the values represent mean±SD.

FIG. 10F is a bar graph of data from an experiment were mice were treated as in FIG. 10A. Lungs were then harvested and assessed for myeloperoxidase (MPO) activity, and the value of vehicle group was set to 1. The values represent mean±SD, with six mice per group.

FIGS. 11A-11B are two bar graphs of real-time qPCR data from an experiment where mice were treated with TNF-α (2 µg/mouse) i.p., LPS i.p. (40 mg/kg, serotype O26:B6), or saline for 4 h. Aortic intima (endothelium) were isolated for total RNA extraction, followed by reverse transcription, and real-time qPCR analysis. The data for expression of miR-181b mRNA is shown in FIG. 11B, and the data for the expression of VCAM-1 mRNA is shown in FIG. 11B. There were 3 to 4 mice per group. The values represent mean±SEM. *P<0.05.

FIG. 11C is a set of three photomicrographs from an experiment where mice were intravenously injected with vehicle (top), miRNA negative control (NS-m) (middle), or miR-181b mimics (181b-m) (bottom). Twenty-four hours later, the mice were treated with or without LPS i.p. (40 mg/kg, serotype O26:B6) for 4 h, and lungs were harvested for Gr-1 staining Bars: 20 µm.

FIG. 11D is a bar graph of quantification data of the number of Gr-1 positive cells per mm vessel length. Four mice were included in each group, and the values represent mean±SD. *P<0.05.

DETAILED DESCRIPTION

Figure 1A:
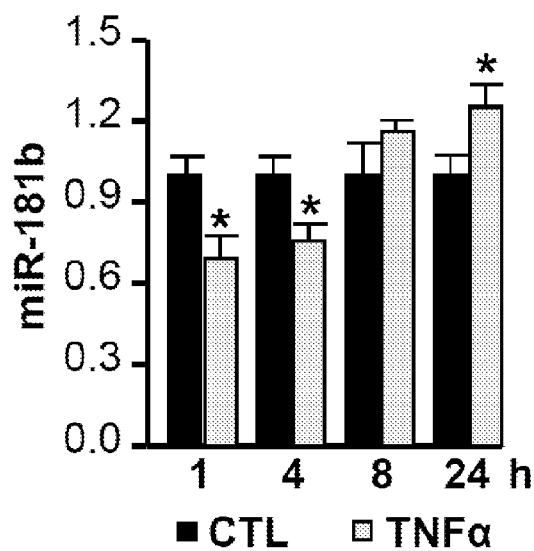
FIGS. 1A-1F are data that show that MiR-181b suppresses TNF-α-induced pro-inflammatory gene expression in human umbilical vein endothelial cells (HUVECs).

Provided herein are methods of treating or delaying the onset of a disease induced or mediated by NF-κB signaling (e.g., a vascular inflammatory disease) including administering to the subject a therapeutically effective amount of a nucleic acid containing all or a part of the sequence of mature miR-181b (SEQ ID NO: 1). Also provided are methods of decreasing NF-κB signaling in a cell (e.g., in a subject, in vitro, or ex vivo) including administering to the endothelial cell a nucleic acid containing all of a part of the sequence of mature miR-181b (SEQ ID NO: 1).

NF-κB

Induction of VCAM-1, E-selectin, and ICAM-1 in endothelial cells (ECs) is primarily mediated by the activation of the NF-κB pathway. Activation of NF-κB transcription factors have been implicated in many physiological and pathological processes (Baker et al., *Cell Metab.* 13:11-22, 2011; Ghosh and Hayden, *Nature Rev. Immunol.* 8:837-848, 2008; Perkins, *Nat. Rev. Mol. Cell. Biol.* 8:49-62, 2007). For example, NF-κB has been implicated for a role in heart failure, ischemia/reperfusion, cardiac hypertrophy, atherosclerosis, multiple sclerosis, muscular dystrophy, bone resorption, Alzheimer's disease, incontinentia pigmenti, ectodermal dysplasia, systematic inflammatory response syndrome, inflammatory bowel diseases, neuropathological diseases, *heliobacter pylori*-associated gastritis, renal diseases, chronic obstructive pulmonary disease, sleep apnea, viral infections (e.g., HIV), skin diseases, gut diseases, sepsis, lupus, aging, diabetes (type I and II), headache, asthma, arthritis, and cancer (Kumar et al., *J. Mol. Med.* 82:434-448, 2004). The present therapies available for the treatment of these diseases often result in negative side effects. Thus, new therapies to treat these diseases (e.g., by inhibiting NF-κB signaling or NF-κB-mediated endothelial cell activation) are desired.

The transcriptional activity of NF-κB can be induced by a variety of stimuli including the pro-inflammatory cytokines TNF-α and IL-1β, growth factors, mitogens, viral or bacterial products (e.g., LPS), T-cell receptor enagement, and stimulation of the CD40 and lymphotoxin-β receptors (Perkins, *Nat. Rev. Mol. Cell. Biol.* 8:49-62, 2007). In the canonical NF-κB signaling pathway stimulus-mediated activation of the inhibitor of kappa B (IκB) kinase (IKK) complex leads to IKK rapidly phosphorylating IκBα at two N-terminal serines, which in turn results in its ubiquitin-induced degradation by the 26S proteasome (Karin and Ben-Neriah, *Ann. Rev. Immunol.* 18:621-663, 2000). This event then leads to the release of NF-κB heterodimers, which then translocate to the nucleus via importin proteins, and drive a wide range of gene expression by binding to various κB promoter elements.

In the vascular endothelium, activation of NF-κB leads to the expression of pro-inflammatory genes, including those encoding cytokines, adhesion molecules, and chemoattractant proteins that together play critical roles in all aspects of the inflammatory and immune responses (Blackwell and Christman, *Am. J. Respir. Cell Mol. Biol.* 17:3-9, 1997; Hajra et al., *Proc. Natl. Acad. Sci. U.S.A.* 97:9052-9057, 2000; Kempe et al., *Nucleic Acids Res.* 33:5308-5319, 2005; Molestina et al., *Infect. Immun.* 68:4282-4288, 2000; Zhou et al., *Cell Signal.* 19:1238-1248, 2007). Thus, targeting NF-κB-mediated endothelial cell activation holds promise for the development of new anti-inflammatory therapies.

Vascular Inflammatory Diseases

Endothelial cells perform multiple functions that are critical to vascular homeostasis, including controlling leukocyte trafficking, regulating vessel wall permeability, and maintenance of blood fluidity. The recruitment of leukocytes and extravasation into the blood vessel wall are essential events to normal inflammatory response and related disease states. This is a multi-step process through which endothelial cells first express specific adhesion molecules, such as E-selectin and VCAM-1 (Berlin et al., *Cell* 80:413-422, 1995; Bevilacqua et al., *Proc. Natl. Acad. Sci. U.S.A.* 84:9238-9242, 1989; Kansas, Blood 88:3259-3287, 1996; Ley et al., *Nat. Rev. Immunol.* 7:678-689, 2007), that facilitate early attachment to the vascular endothelium. Endothelial cells also produce a variety of C—C and C—X—C chemokines, which act to further promote leukocyte recruitment. After leukocyte transmigration occurs, invasion of adjacent tissues allows for propagation of the initial inflammatory response.

Figure 6:
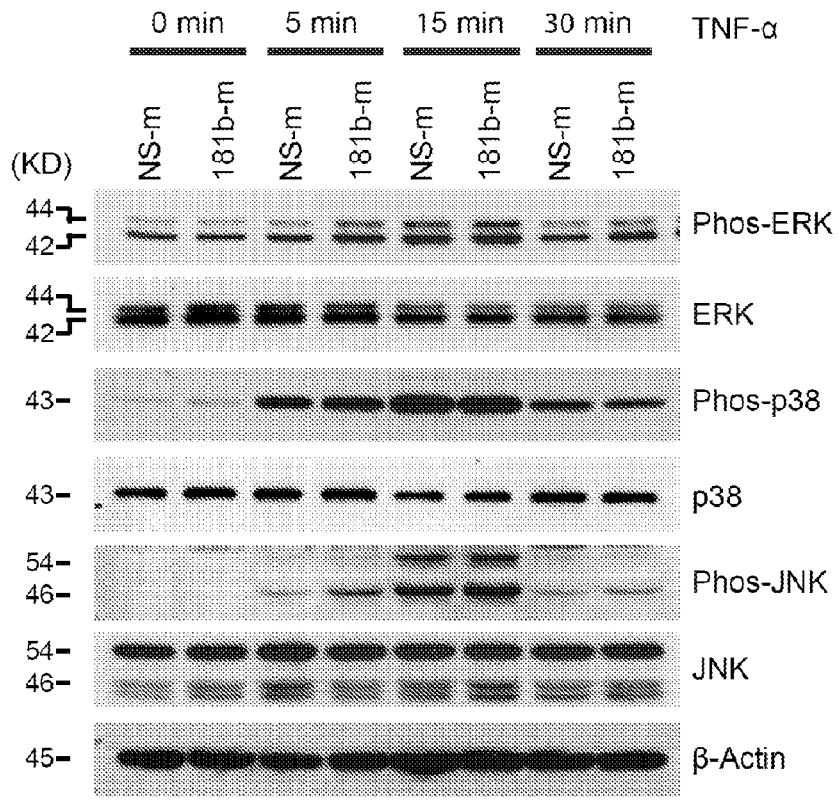
FIG. 6 is a Western blot of phospho-ERK, total ERK, phospho-p38, total p38, phospho-JNK, and total JNK in HUVECs transfected with either 10 nM miRNA negative control or 10 nM miR-181b mimics, and treated with 10 ng/ml TNF-α for the indicated times.

The discovery that miR-181b can potently inhibit adhesion molecules, chemokines, and other NF-κB-responsive mediators indicate that it can serve to dampen the early and late stages of vascular inflammation. MiR-181b-mediated inhibition is observed for several major physiologic pro-inflammatory mediators, such as TNF-α and LPS (see FIGS. 1, 3, 9, and 10). Functionally, miR-181b impaired leukocyte adhesion to a stimulated endothelial cell monolayer in vitro and leukocyte accumulation in the lungs in vivo (FIGS. 3 and 10). The effect of miR-181b was determined to be specific for the NF-κB signaling pathway as the majority of the TNF-α-inducible genes examined were inhibited by miR-181b. Moreover, interrogation of the entire set of over 800 miR-181b-reduced genes identified by microarray analysis revealed six biological signaling pathways associated with NF-κB activation. miR-181b had no effect on phosphorylation of the MAPK downstream mediators, ERK, p38, and JNK (FIG. 6). These findings show that miR-181b functions as a negative inhibitor of NF-κB signaling events in response to pro-inflammatory stimuli in the vascular endothelium.

Accordingly, methods of treating a vascular inflammatory disease are provided herein. A vascular inflammatory disease is a disease that involves at one or more (e.g., one, two, or three) stages (e.g., an early stage (e.g., before the development of one or more symptoms of a vascular inflammatory disease or before diagnosis by a health care professional), an intermediate stage (e.g., following the development of one or more symptoms of a vascular inflammatory disease or following diagnosis by a health care professional), or a late stage (e.g., following the manifestation of one or more severe symptoms of a vascular inflammatory disease that require admission into a health care facility (e.g., a hospital or an intensive care unit))) in the pathobiology of the disease one or more (e.g., one, two, three, or four) of: endothelial cell activation, leukocyte adhesion to the endothelium, leukocyte extravasation of the endothelium, and increased (e.g., a significant increase, such as by at least 5%, 10%, 15%, 20%, 25%, 30%, 35%, 40%, 45%, 50%, 55%, 60%, 70%, 80%, 90%, or 95%) expression (protein or mRNA) in one or more of VCAM-1, E-selectin, or ICAM-1 in the endothelium compared to a control subject (e.g., a healthy or asymptomatic subject, a subject not diagnosed with a vascular inflammatory disease, a subject not presenting with one or more symptoms of a vascular inflammatory disease, the same subject prior to the development of one or more symptoms of a vascular inflammatory disease, the same subject prior to diagnosis with a vascular inflammatory disease, or the same subject at an earlier stage of the vascular inflammatory disease). Non-limiting examples of vascular inflammatory diseases include: lung inflammation (e.g., acute lung injury, such as sepsis-induced acute lung injury), asthma, atherosclerosis, arthritis, stroke, inflammatory bowel syndrome, cardiovascular disease, myocardial infarction, coronary artery disease, heart failure, ulcerative colitis, Crohn's disease, and peripheral artery disease.

As described above, NF-κB has been implicated for a role in the development of vascular inflammatory diseases. For example, NF-κB signaling mediates the up-regulated expression of VCAM-1, E-selectin, and ICAM-1 in endothelial cells, which mediate leukocyte attachment and allow the extravasation of leukocytes to the site of injury. Evidence of such a connection between NF-κB and specific vascular inflammatory diseases is known. For example, activated NF-κB has been identified in situ in human atherosclerotic plaques, but not in vessels that are devoid of atherosclerosis (Collins et al., *J. Clin. Invest.* 107:255-264, 2001), NF-κB plays an almost exclusive role in ischemia/reperfusion (Valen et al., *J. Am. Coll. Cardiol.* 38:307-314, 2001) and in the early phase of myocardial infarction (Shimizu et al., *Cardiovasc. Res.* 38:116-124, 1998), activated NF-κB is a common feature in human rheumatoid arthritis synovium (Marok et al., *Arthritis Rheum.* 39:583-591, 1996; Gilston et al., *Biochem. Soc. Trans.* 25:518S, 1997; Miyazawa et al., *Am. J. Pathol.* 152:793-803, 1998) and in various animal models of rheumatoid arthritis in rats, collagen-induced arthritis in mice, and streptococcal cell wall induced arthritis in rats (Makarov et al., *Arthritis Res.* 3:300-206, 2001), and higher NF-κB activation has been reported in colonic biopsy samples, as well as lamina propria mononuclear cells from patients with Crohn's disease (Ellis et al., *Inflamm. Res.* 47:440-445, 1998).

A health care professional (e.g., a physician, nurse, a physician's assistant, or a laboratory technician) may diagnose a subject as having a vascular inflammatory disease or may monitor the severity, frequency, or duration one or more (e.g., two, three, four, five, or six) symptoms of a vascular inflammatory disease in a subject (e.g., in a subject receiving one or more doses of a nucleic acid containing all or a part of the sequence of SEQ ID NO: 1). Such diagnosis may be made using methods known in the art (e.g., by the assessment of one or more physical symptoms of a vascular inflammatory disease known in the art or diagnostic tests, for e.g., those described in Maksimowic-McKinnon et al., *Curr. Opin. Rheumatol.* 16:18-24, 2004). Additional laboratory tests for the diagnosis of specific vascular inflammatory diseases are known in the art (e.g., C-reactive protein and pro-inflammatory cytokines, such as TNF-α and IL-1). A subject that is diagnosed as having a vascular inflammatory disease or is receiving treatment for a vascular inflammatory disease may be admitted to a health care facility (e.g., hospital, intensive care unit, or an assisted living facility).

Additional Indications

As described above, in addition to its role in vascular inflammatory diseases, NF-κB has been implicated in other disease states. For example, NF-κB signaling has been implicated in obesity, insulin-resistance, diabetes (type I and II), viral infections (e.g., AIDS), cancer, Alzheimer's disease, muscular dystrophy, bone resorption, ischemia/reperfusion, cardiac hypertrophy, incontinentia pigmenti, ectodermal dysplasia, systematic inflammatory response syndrome, *heliobacter pylori*-associated gastritis, renal diseases, sleep apnea, skin diseases, lupus, aging, and headache. Transdominant mutants of IκBα that block NF-κB induction also inhibit de novo HIV-1 infection in T-cells by interfering with viral replication, which indicates that NF-κB promotes the pathogenesis of HIV-1 in infected cells (Quinto et al., *J. Bio. Chem.* 274:17567-17572, 1999; Kwon et al., *J. Biol. Chem.* 273: 7431-7440, 1998). The ability of NF-κB to suppress apoptosis and to induce expression of proto-oncogenes, such as c-myc and cyclin D1, which directly stimulate proliferation, suggest that NF-κB participates in many aspects of oncogenesis (Pahl, *Oncogene* 18:6853-6866, 1999;Gutridge et al., *Mol. Cell Biol.* 19:5785-5799, 1999). NF-κB also regulates the expression of various molecules, such as cell adhesion proteins, matrix metalloproteinases, cyclooxygenase 2, inducible nitric oxide synthase, chemokines, and inflammatory cytokines, all of which promote tumor cell invasion and angiogenesis (Bharti et al., *Biochem. Pharmacol.* 64:883-888, 2002). In addition, accumulating evidence implicates free radicals and NF-κB signaling in the destruction of islet β cells and diabetes disease progression (Ho et al., *Proc. Soc. Exp. Biol. Med.* 222:205-213, 1999). An elevated NF-κB signaling pathway was also observed in the skeletal muscle fibers of patients with polymyositis, dermatomyositis, and Duchenne muscular dystrophy (Monici et al., *Neurology* 60:993-997, 2003). NF-κB immunoreactivity was also found in and around early neurological plaque types in Alzheimer's disease (Kaltschmidt et al., *Proc. Natl. Acad. Sci. U.S.A.* 96:9409-9414, 1999; O'Neill et al., *Trends Neurosci.* 20:252-258, 1997). Increased activation of NF-κB has also been reported in active multiple sclerosis lesions (Bonetti et al., *Am. J. Pathol.* 155:1433-1438, 1999; Gveric et al., *J. Neuropathol. Exp. Neurol.* 57:168-178, 1998). In addition, NF-κB signaling has been implicated for a mechanistic role in bone resorption (Kumar et al., *J. Mol. Med.* 82:434-448, 2004).

As NF-κB signaling has been implicated for a role in the development or progression of these disease states, treatment of these disease states may also be performed, in part, by administering a nucleic acid containing all or a part of the sequence of mature miR-181b (SEQ ID NO: 1), as described for vascular inflammatory diseases below.

MiR-181b

MiRNAs are a class of single-stranded, small non-coding RNAs that typically bind to the 3'-untranslated region (3'-UTR) of target mRNA sequences, an effect leading to the reduction of protein expression predominantly by destabilizing target mRNAs and/or by translation inhibition (Baek et al., *Nature* 455:64-71, 2008; Bartel, *Cell* 136:215-233, 2009; Guo et al., *Nature* 466:835-840, 2010; Valencia-Sanchez et al., *Genes Dev.* 20:515-524, 2006). While over 1,000 mature human miRNA sequences are listed in the miRNA registry, only a small handful have been characterized as functional regulators of leukocyte or endothelial cell inflammatory responses.

MiR-181b belongs to the miR-181 family which consists of four members: miR-181a, miR-181b, miR-181c, and miR-181d. The biological functions of this miRNA family were first identified when miR-181a was recognized as a contributor to hematopoietic lineage commitment and differentiation (Chen et al., *Science* 303:83-86, 2004; Li et al., *Cell* 129:147-161, 2007). Later studies revealed that increased miR-181a activity in primary embryonic lymphatic endothelial cells resulted in substantially reduced levels of Prox1 mRNA and protein and, consequently, regulated vascular development and neo-lymphangiogenesis (Kazenwadel et al., *Blood* 116: 2395-2401, 2010). MiR-181b was defined as a regulator of the B-cell primary antibody repertoire based upon its ability to restrict the activity of activation-induced cytidine deaminase (de Yebenes et al., *J. Exp. Med.* 205:2199-2206, 2008). Members of the miR-181 family may have non-redundant functions, as was suggested by the data described herein and in one study in which miR-181a, but not miR-181c, promoted CD4 and CD8 double-positive T-cell development when ectopically expressed in thymic progenitor cells (Liu et al., *PloS One* 3:e3592, 2008).

Figure 2A:
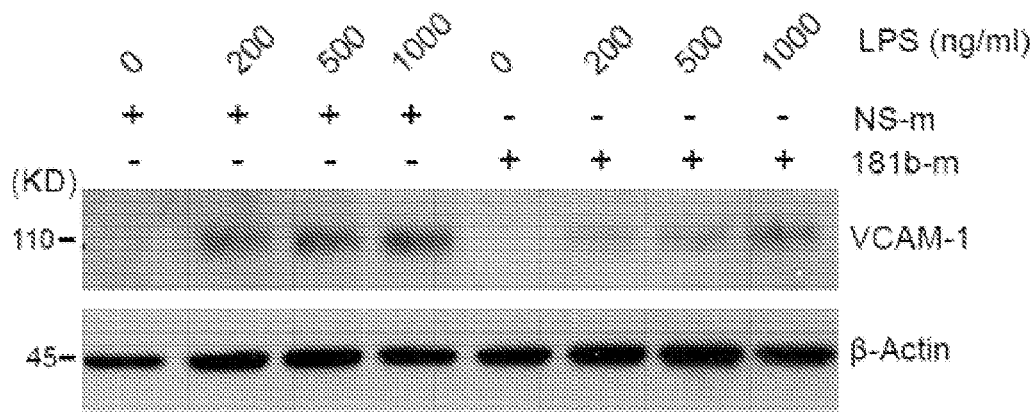
FIGS. 2A-2E is two Western blots and five bar graphs showing that miR-181b inhibits pro-inflammatory induction of VCAM-1 expression.
Figure 2B:
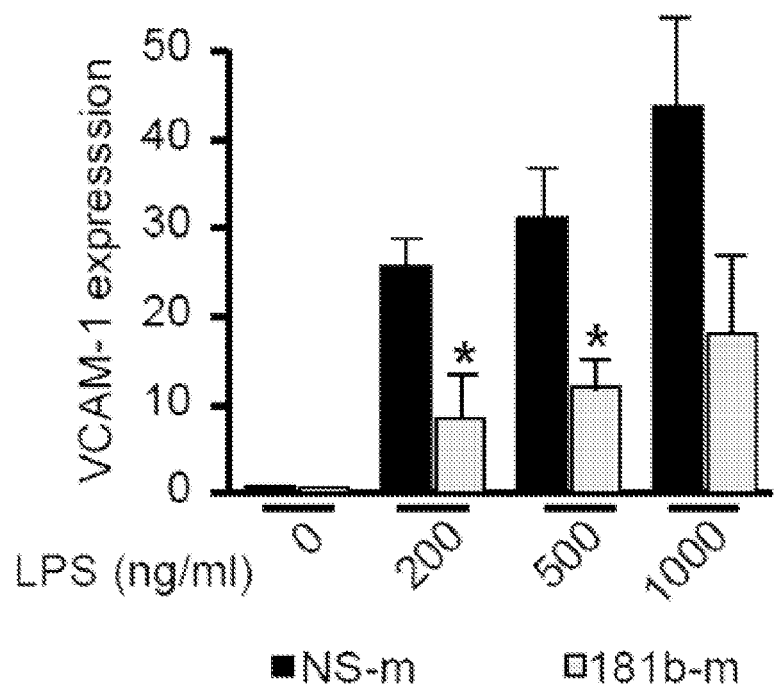
Figure 2C:
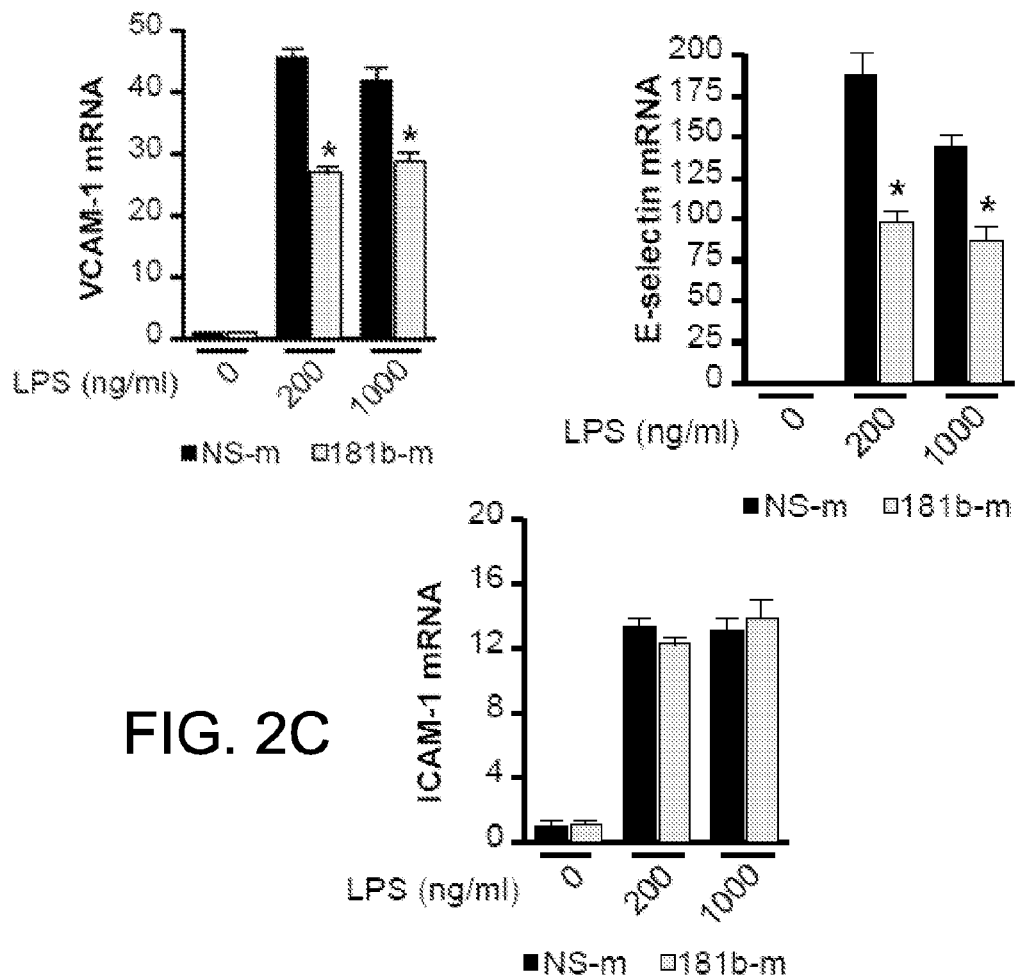
Figure 2D:
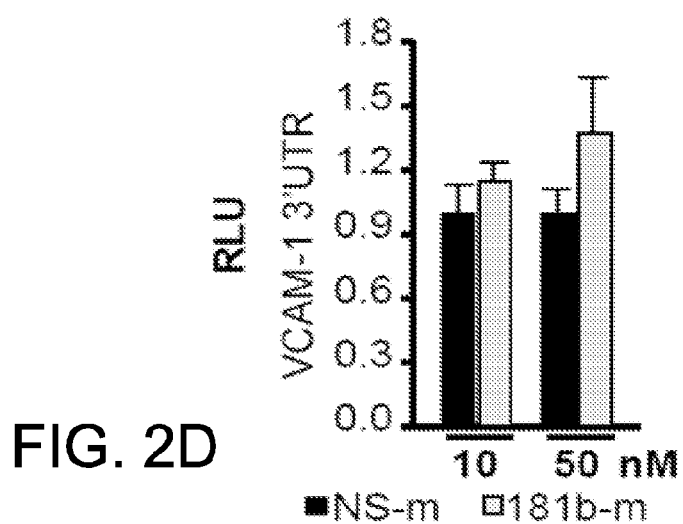
Figure 2E:
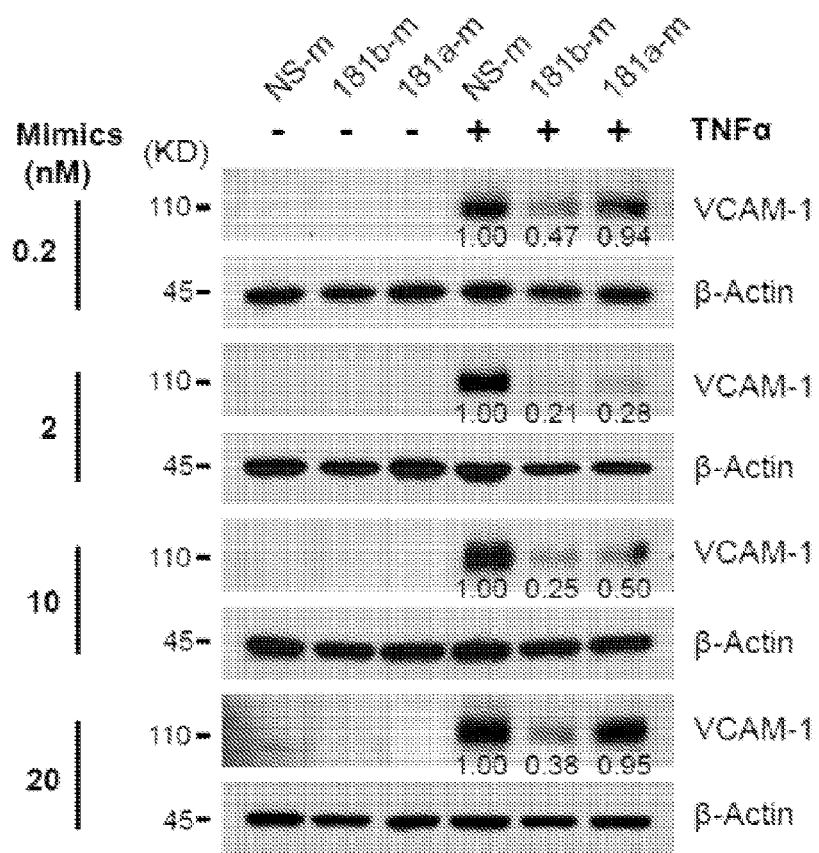

MiR-181b was found to be the dominant miR-181 family member expressed in endothelial cells and was shown to be capable of more potently suppressing endothelial cell activation than the next highest expressed family member, miR-181a (FIG. 2E). MiR-181b was further discovered to target the 3'-UTR of importin-α3: a protein that mediates the translocation of NF-κB from the cytoplasm into the nucleus.

Figure 7A:
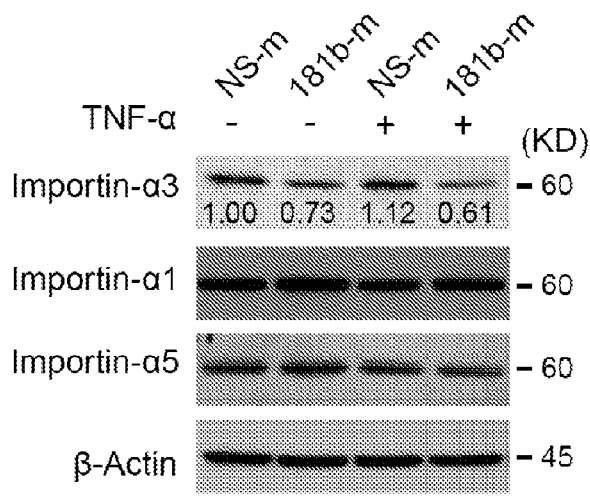
FIGS. 7A-F is a Western blot and a set of six bar graphs showing that miR-181b reduces importin-α3 expression.
Figure 7B:
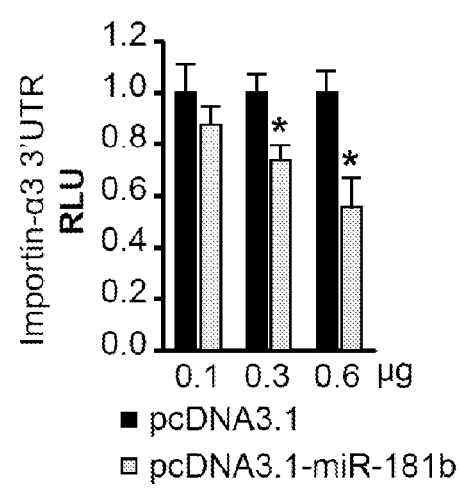
Figure 7C:
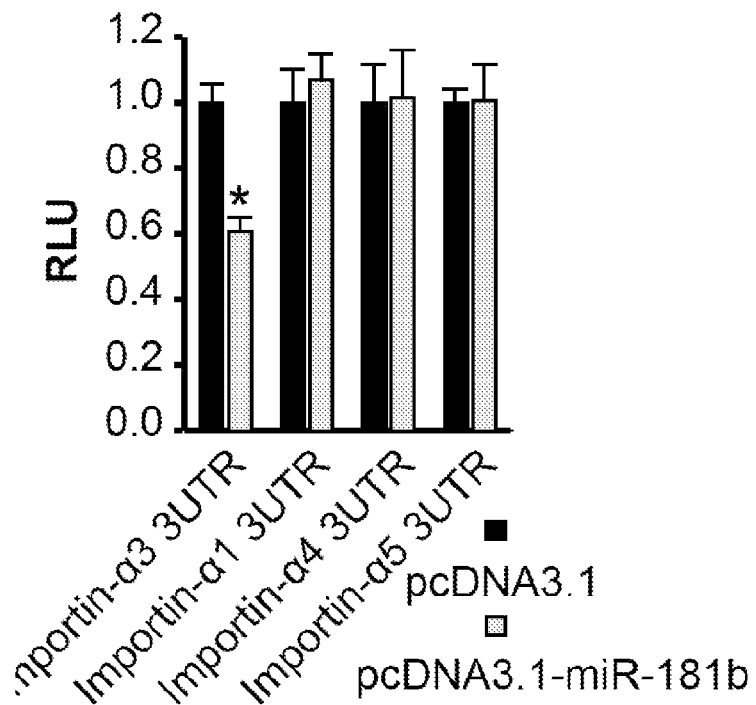
Figure 7D:
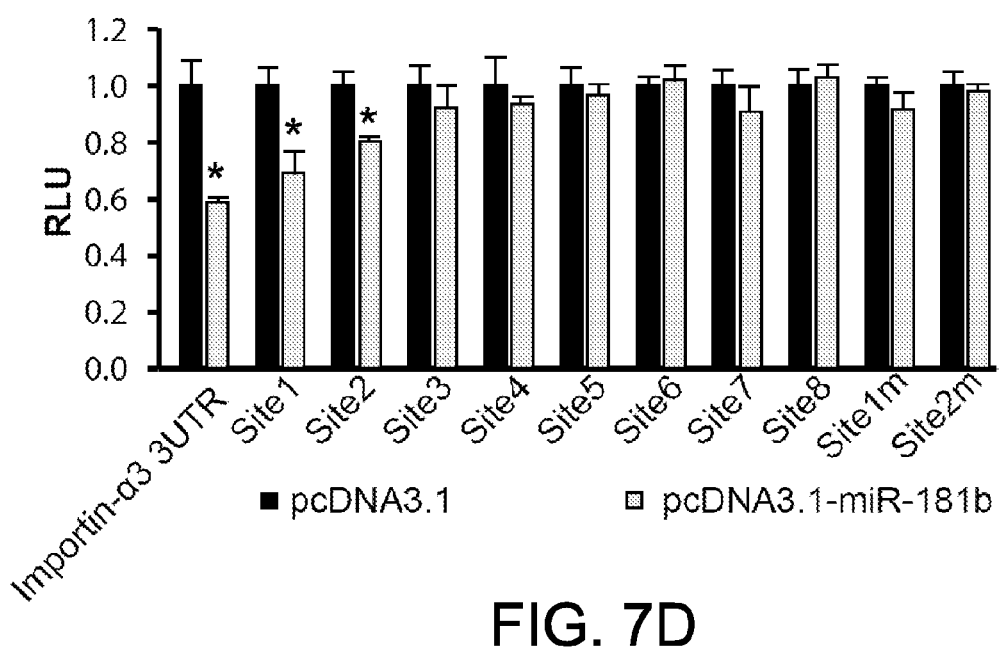
Figure 7E:
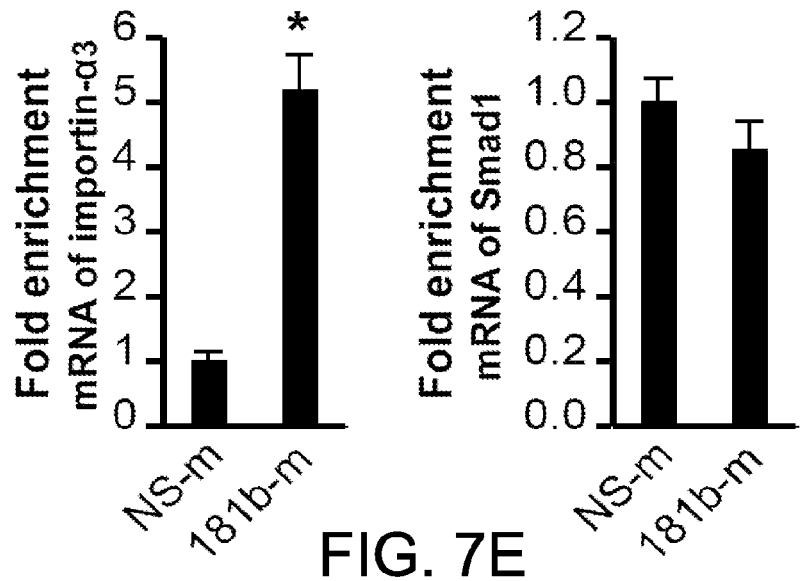
Figure 7F:
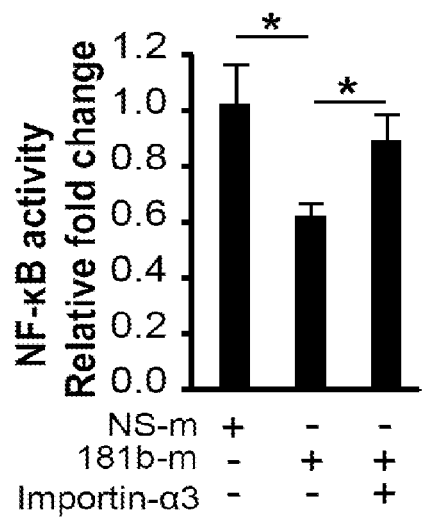

Importins are a family of proteins involved in nuclear translocation. Using a combination of experimental approaches, including bioinformatics, 3'-UTR reporter assays, and miRNP-IP, miR-181b was shown to directly target EC-expressed importin-α3 in response to TNF-α. Furthermore, over-expression of importin-α3 (lacking its 3'-UTR) effectively rescued miR-181b-mediated inhibition of NF-κB-induced activity (FIG. 7F).

Mature human miR-181b has the sequence of: aacauucauugcugucggugggu (SEQ ID NO: 1). Mature miR-181b is generated from the processing of a precursor miRNA molecule, for example, a miR-181b precursor hairpin sequence (hsa-mir-181b-1) encoded on chromosome 1 (Lim et al., *Science* 299:1540, 2003) (CCUGUGCAGAGAUU AUU-UUUUAAAAGGUCACAAUCAACAUUCA-UUGCUGUCGGUGGGUUGAACU GUGUGGACAAGCUCACUGAA-CAAUGAAUGCAACUGUGGCCCCGCUU; SEQ ID NO: 2) or a mir-181b precursor hairpin sequence (hsa-mir-181b-2) encoded on human chromosome 9 (Weber, *FEBS J.* 272:59-73, 2005) (CUGAUGGCUGCACUCAACAUU CAUUGCUGUCGGUGGGUUUGAGU-CUGAAUCAACUCACUGAUCAAUGAAUG CAAACUGCGGACCAAACA; SEQ ID NO: 3). In some of the embodiments of the methods described herein a nucleic acid containing SEQ ID NO: 2 or SEQ ID NO: 3 is administered to a subject.

The methods provided herein include administering to a subject a nucleic acid that contains all or a part of the sequence of mature miR-181b (SEQ ID NO: 1). A variety of examples of such nucleic acids are described below. A nucleic acid containing all or a part of the sequence of mature miR-181b (SEQ ID NO: 1) may include one or more of any of the modifications described herein, without limitation.

Nucleic Acids

Provided herein are methods for treating or delaying the onset of a vascular inflammatory disease and methods for decreasing NF-κB signaling in an endothelial cell that include the administration of a nucleic acid that contains all of a part of the sequence of mature miR-181b (SEQ ID NO: 1). The nucleic acid can be, for example e.g., an antisense oligonucleotide that contains all or a part of the sequence of mature miR-181b (SEQ ID NO: 1); in some embodiments, as described in further detail below, the nucleic acid includes different modifications, e.g., in the sugar backbone, to make it more cell permeable and nuclease resistant on one hand, and physiologically non-toxic at low concentrations on the other. The nucleic acids for use in practicing the methods described herein, that contain all or a part of the sequence of mature miR-181b (SEQ ID NO: 1), can be those which bind to the 3'-UTR of importin-α3 (e.g., bind to a part of site 1 or site 2 of the 3'-UTR of an importin-α3 mRNA as shown in FIG. 8A) and/or prevent translation of the importin-α3 mRNA, such as an interfering RNA, including but not limited to an shRNA or siRNA.

Inhibitory Nucleic Acids

Nucleic acids useful in the present methods and compositions include microRNAs, antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which contain all or a part of the sequence of mature miR-181b (SEQ ID NO: 1) and/or hybridize to at least a portion the 3'UTR of importin-3α (e.g., site 1 or site 2 of the 3'-UTR of an importin-α3 mRNA as shown in FIG. 8A) and modulate its expression. In some embodiments, the nucleic acids include microRNAs, antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, for example, WO 10/040,112.

In some embodiments, the nucleic acids are 10 to 120, 10 to 110, 10 to 100, 10 to 90, 10 to 80, 10 to 70, 10 to 60, 10 to 50, 13 to 50, 13 to 30, or 15 to 25 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds are 12 or 13 to 30 nucleotides in length. One having ordinary skill in the art will appreciate that this embodies nucleic acids having antisense portions of 12, 13, 14, 15, 16, 17, 18, 19, 20, 21, 22, 23, 24, 25, 26, 27, 28, 29 or 30 nucleotides in length, or any range therewithin. In some embodiments, the nucleic acid contains at 5, 6, 7, 8, 9, 10, 11, 12, 13, 14, 15, 16, 17, 18, 19, 20, 21, 22, or 23 continuous nucleotides of SEQ ID NO: 1. In additional embodiments, the nucleic acid contains all or a part (e.g., at least 10, 20, 30, 40, 50, 60, 70, 75, 80, 90, or 100 nucleotides of SEQ ID NO: 2 or SEQ ID NO: 3).

In some embodiments, the nucleic acids may be designed to target the 3'-UTR of importin-α3 as described in the examples (e.g., target site 1 and/or site 2 of the 3'-UTR of an importin-α3 mRNA as shown in FIG. 8A). Alternatively or in addition, highly conserved regions within the importin-α3 mRNA can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., *J. Mol. Biol.*, 215:403-410, 1990; Zhang and Madden, *Genome Res.*, 7:649-656, 1997), e.g., using the default parameters.

In some embodiments, the nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric nucleic acids used in the methods may be formed as composite structures of two or more oligonucleotides, modified oligonucleotides, oligonucleosides, and/or oligonucleotide mimetics as described herein. Such compounds have also been referred to in the art as hybrids or gapmers. Representative U.S. patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, any of the nucleic acids described herein comprise at least one nucleotide modified at the 2' position of the sugar, most preferably a 2'-O-alkyl, 2'-O-alkyl-O-alkyl, or 2'-fluoro-modified nucleotide. In other preferred embodiments, RNA modifications include 2'-fluoro, 2'-amino, and 2' O-methyl modifications on the ribose of pyrimidines, abasic residues, or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligonucleotides survive intact for a longer time than unmodified oligonucleotides. Specific examples of modified oligonucleotides include those comprising modified backbones, for example, phosphorothioates, phosphotriesters, methyl phosphonates, short-chain alkyl, or cycloalkyl intersugar linkages, or short-chain heteroatomic or heterocyclic intersugar linkages. Most preferred are oligonucleotides with phosphorothioate backbones and those with heteroatom backbones, particularly $CH_2$—NH—O—$CH_2$, CH, ~$N(CH_3)$~O~$CH_2$ (known as a methylene(methylimino) or MMI backbone), $CH_2$—O—N($CH_3$)—$CH_2$, $CH_2$—N ($CH_3$)—$N(CH_3)$—$CH_2$ and O—N ($CH_3$)—$CH_2$—$CH_2$ backbones, wherein the native phosphodiester backbone is represented as O—P—O—CH); amide backbones (see De Mesmaeker et al. *Ace. Chem. Res.* 28:366-374, 1995); morpholino backbone structures (see U.S. Pat. No. 5,034,506); and peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., *Science* 254:1497, 1991). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'-alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and Corey, *Biochemistry* 41(14):4503-4510, 2002; *Genesis*, volume 30, issue 3, 2001; Heasman, J., *Dev. Biol.* 243:209-214, 2002; Nasevicius et al., *Nat. Genet.* 26:216-220, 2000; Lacerra et al., *Proc. Natl. Acad. Sci. U.S.A.* 97, 9591-9596, 2000; and U.S. Pat. No. 5,034,506. Cyclohexenyl nucleic acid oligonucleotide mimetics are described in Wang et al., *J. Am. Chem. Soc.* 122:8595-8602, 2000.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH$_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$OCH3, OCH$_3$—O—(CH$_2$)nCH$_3$, O(CH$_2$)nNH$_2$ or O(CH$_2$)nCH$_3$ where n is from 1 to about 10; C1 to C10 lower alkyl, alkoxyalkoxy, substituted lower alkyl, alkaryl, or aralkyl; Cl; Br; CN; CF$_3$; OCF$_3$; O-, S-, or N-alkyl; O-, S-, or N-alkenyl; SOCH$_3$; SO$_2$CH3; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH$_2$CH$_2$OCH$_3$, also known as 2'-O-(2-methoxyethyl)] (Martin et al, Helv. Chim. Acta 78:486, 1995). Other preferred modifications include 2'-methoxy (2'-O—CH$_3$), 2'-propoxy (2'-OCH$_2$CH$_2$CH$_3$), and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Any of the nucleic acids described herein can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, pp 75-77, 1980; Gebeyehu, G., et al. Nucl. Acids Res. 15:4513, 1987). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, pp. 276-278, 1993) and are presently preferred base substitutions.

It is not necessary for all positions in a given oligonucleotide to be uniformly modified, and in fact more than one (e.g., two, three, four, or five) of the aforementioned modifications may be incorporated in a single oligonucleotide or even at within a single nucleoside within an oligonucleotide. Within a given nucleic acid used in the methods described herein, one or more (e.g., at least 2, 3, 4, 5, 6, 7, 8, 9, 10, 11, 12, 13, 14, or 15) of the nucleotides may be modified using any of the modifications described herein (e.g., sugar, base, or internucleoside linkage).

In some embodiments, both a sugar and an internucleoside linkage, i.e., the backbone, of the nucleotide units are replaced with novel groups. The base units are maintained for hybridization with an appropriate nucleic acid target compound (e.g., the 3'-UTR of importin-α3). One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative U.S. patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science 254:1497-1500, 1991.

Some nucleic acids can also include one or more (e.g., at least 2, 3, 4, 5, 6, 7, 8, 9, 10, 11, 12, 13, 14, or 15) nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil; 2-thiothymine; 2-thiocytosine; 5-halouracil and cytosine; 5-propynyl uracil and cytosine; 6-azo uracil, cytosine, and thymine; 5-uracil (pseudo-uracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylquanine; 7-methyladenine; 8-azaguanine; 8-azaadenine; 7-deazaguanine; 7-deazaadenine; 3-deazaguanine; and 3-deazaadenine.

Further, nucleobases comprise those disclosed in U.S. Pat. No. 3,687,808, those disclosed in 'The Concise Encyclopedia of Polymer Science And Engineering,' pages 858-859, Kroschwitz, J. I., Ed. John Wiley & Sons, 1990, those disclosed by Englisch et al., Angewandle Chemie, International Edition, volume 30, page 613, 1991, and those disclosed by Sanghvi, Y. S., Chapter 15, Antisense Research and Applications, pages 289-302, Crooke, S. T. and Lebleu, B. ea., CRC Press, 1993. Certain of these nucleobases are particularly useful for increasing the binding affinity of the oligomeric compounds used in the methods described herein. These include 5-substituted pyrimidines, 6-azapyrimidines, and N-2, N-6 and 0-6 substituted purines, comprising 2-aminopropyladenine, 5-propynyluracil, and 5-propynylcytosine. 5-methylcytosine substitutions have been shown to increase nucleic acid duplex stability by 0.6-1.2° C. (Sanghvi, Y. S., Crooke, S. T. and Lebleu, B., Eds, Antisense Research and Applications, CRC Press, Boca Raton, pp. 276-278, 1993) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205;

5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692; and 5,681,941, each of which is herein incorporated by reference.

In some embodiments, any of the nucleic acids described herein are chemically linked to one or more (e.g., two, three, four, five, or six) moieties or conjugates (e.g., a polymer, a peptide, or a polysaccharide) that enhance the activity, cellular distribution, or cellular uptake of the oligonucleotide. Such moieties comprise but are not limited to, lipid moieties such as a cholesterol moiety (Letsinger et al., *Proc. Natl. Acad. Sci. U.S.A.* 86:6553-6556, 1989), cholic acid (Manoharan et al., *Bioorg. Med. Chem. Lett.* 4:1053-1060, 1994), a thioether, e.g., hexyl-S-tritylthiol (Manoharan et al., *Ann. N.Y. Acad. Sci.* 660:306-309, 1992; Manoharan et al., *Bioorg. Med. Chem. Lett.* 3:2765-2770, 1993), a thiocholesterol (Oberhauser et al., *Nucl. Acids Res.* 20:533-538, 1992), an aliphatic chain, e.g., dodecandiol or undecyl residues (Kabanov et al., *FEBS Lett.* 259:327-330, 1990; Svinarchuk et al., *Biochimie* 75:49-54, 1993), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 36:3651-3654, 1995; Shea et al., *Nucl. Acids Res.* 18:3777-3783, 1990), a polyamine, a polyethylene glycol chain, or a polyalkylene glycol chain (Mancharan et al., *Nucleosides & Nucleotides* 14:969-973, 1995), or adamantane acetic acid (Manoharan et al., *Tetrahedron Lett.* 36:3651-3654, 1995), a palmityl moiety (Mishra et al., *Biochim. Biophys. Acta* 1264:229-237, 1995), or an octadecylamine or hexylamino-carbonyl-t oxycholesterol moiety (Crooke et al., *J. Pharmacol. Exp. Ther.* 277:923-937, 1996). See also U.S. Pat. Nos. 4,828,979; 4,948,882; 5,218,105; 5,525,465; 5,541, 313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid (e.g., the 3'-UTR of importin-α3). Groups that enhance the pharmacokinetic properties, in the context of this invention, include groups that improve uptake, distribution, metabolism, or excretion of the compounds of the present invention. Representative conjugate groups are disclosed in WO 93/007883, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine, a polyalkylene glycol or a polyethylene glycol chain, adamantane acetic acid, a palmityl moiety, or an octadecylamine or hexylamino-carbonyl-oxy cholesterol moiety. See, e.g., U.S. Pat. Nos. 4,828,979; 4,948, 882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941.

The nucleic acids useful in the present methods contain all or a part of the sequence of mature miR-181b (SEQ ID NO: 1), e.g., hybridize sufficiently well and with sufficient specificity (e.g., complementary to a sequence present in the 3'-UTR of importin-α3, such as site 1 and/or site 2 in the 3'-UTR of an importin-α3 mRNA as shown in FIG. 8A), to give the desired effect. "Complementary" refers to the capacity for pairing, through hydrogen bonding, between two sequences comprising naturally or non-naturally occurring bases or analogs thereof. For example, if a base at one position of a nucleic acid is capable of hydrogen bonding with a base at the corresponding position of the target (e.g., a base in the 3'-UTR of importin-α3), then the bases are considered to be complementary to each other at that position. 100% complementarity is not required.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. The nucleic acids and a sequence present in an importin-α3 mRNA (e.g., a sequence present in the 3'-UTR of importin-α3) are complementary to each other when a sufficient number of corresponding positions in each molecule are occupied by nucleotides that can hydrogen bond with each other. Thus, "specifically hybridizable" and "complementary" are terms which are used to indicate a sufficient degree of complementarity or precise pairing such that stable and specific binding occurs between the nucleic acid and the target sequence (e.g., a sequence present in the importin-α3 mRNA, such as a sequence present in the 3'-UTR of importin-α3). For example, if a base at one position of a nucleic acid is capable of hydrogen bonding with a base at the corresponding position of an importin-α3 mRNA, then the bases are considered to be complementary to each other at that position.

Although in some embodiments, 100% complementarity is desirable, it is understood in the art that a complementary nucleic acid sequence need not be 100% complementary to that of its target nucleic acid to be specifically hybridisable. A complementary nucleic acid sequence for purposes of the present methods is specifically hybridizable when binding of the sequence to a importin-α3 mRNA interferes with the normal function of the importin-α3 mRNA to cause a loss of activity, and there is a sufficient degree of complementarity to avoid non-specific binding of the sequence to non-target mRNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci. U.S.A.* 72:3961, 1975); Ausubel et al. (Current Protocols in Molecular Biology, Wiley Interscience, New York, 2001); Berger and Kimmel (Guide to Molecular Cloning Techniques, Academic Press, New York, 1987); and Sambrook et al., Molecular Cloning: A Laboratory Manual, Cold Spring Harbor Laboratory Press, New York.

In general, the nucleic acids useful in the methods described herein have at least 80% sequence complementarity to a target region within the target nucleic acid, e.g., 90%, 95%, 96%, 97%, 98%, 99%, or 100% sequence complementarity to the target region in an importin-α3 mRNA (e.g., a target region within the 3'-UTR of the importin-α3 mRNA, such as site 1 and/or site 2 in the 3'-UTR of an importin-α3 mRNA as shown in FIG. 8A). For example, an antisense compound in which 18 of 23 nucleobases of the antisense oligonucleotide are complementary, and would therefore specifically hybridize, to a target region would represent 90 percent complementarity. Percent complementarity of a nucleic acid with a region of a target nucleic acid can be determined routinely using basic local alignment search tools (BLAST programs) (Altschul et al., *J. Mol. Biol.* 215, 403-410, 1990; Zhang and Madden, *Genome Res.* 7:649-656, 1997). Antisense and other compounds that can be used in the methods that hybridize to an importin-α3 mRNA target sequence are identified through routine experimentation. In general the nucleic acids must retain specificity for their target, i.e., must not directly bind to, or directly significantly affect expression levels of, transcripts other than the intended target.

For further disclosure regarding exemplary nucleic acids that may be used in any one of the methods described herein, please see US 2010/0317718 (antisense oligonucleotides); US 2010/0249052 (double-stranded ribonucleic acid (dsRNA)); US 2009/0181914 and US 2010/0234451 (LNAs); US 2007/0191294 (siRNA analogues); US 2008/0249039 (modified siRNA); and WO 10/129,746 and WO 10/040,112 (inhibitory nucleic acids).

Antisense Nucleic Acids

In some embodiments, the nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a contiguous sequence in an importin-α3 mRNA (e.g., site 1 and/or site 2 of the 3'-UTR of an importin-α3 mRNA as shown in FIG. 8A). Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, any of the nucleic acids described herein contain one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the base pairing reaction (Jepsen et al., *Oligonucleotides* 14:130-146, 2004). LNAs also have increased affinity to base pair with RNA as compared to DNA. These properties render LNAs especially useful as probes for fluorescence in situ hybridization (FISH) and comparative genomic hybridization, and as antisense oligonucleotides to target mRNAs or other RNAs.

The LNA molecules can include molecules comprising 10-120, 10-110, 10-100, 10-90, 10-80, 10-70, 10-60, 10-50, 10-40, 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, 96%, 97%, 98%, 99%, or 100%) identical, e.g., having 3, 2, 1, or 0 mismatched nucleotide(s), to a target sequence (e.g., a sequence present in an importin-α3 mRNA, such as a sequence present in the 3'-UTR of an importin-α3 mRNA). The LNA molecules can be chemically synthesized using methods known in the art. The LNA molecules can be designed using any method known in the art; a number of algorithms are known, and are commercially available (e.g., on the internet, for example at the Exiqon website). See, e.g., You et al., *Nuc. Acids. Res.* 34:e60, 2006; McTigue et al., *Biochemistry* 43:5388-405, 2004; and Levin et al., *Nuc. Acids. Res.* 34:e142, 2006. For example, "gene walk" methods, similar to those used to design antisense oligonucleotides, can be used to optimize the inhibitory activity of the LNA (or any other nucleic acid described herein); for example, a series of oligonucleotides of 10-30 nucleotides spanning the length of a target importin-α3 sequence can be prepared, followed by testing for activity. Optionally, gaps, e.g., of 5-10 nucleotides or more, can be left between the LNAs to reduce the number of oligonucleotides synthesized and tested. The GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs. For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Patent Application Publication Nos. 2010/0267018; 2010/0261175; and 2010/0035968; Koshkin et al. *Tetrahedron* 54:3607-3630, 1998; Obika et al., *Tetrahedron Lett.* 39:5401-5404, 1998; Jepsen et al., *Oligonucleotides* 14:130-146, 2004; Kauppinen et al., *Drug Disc. Today* 2(3):287-290, 2005; and Ponting et al., *Cell* 136(4):629-641, 2009, and references cited therein.

siRNA/shRNA

In some embodiments, the nucleic acid can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule (e.g., complementary to a sequence present in an importin-α3 mRNA, such as site 1 and/or site 2 in the 3'-UTR of an importin-α3 mRNA as shown in FIG. 8A) or a portion thereof and the sense strand comprises nucleotide sequence corresponding to the target nucleic acid sequence (e.g., a sequence present in an importin-α3 mRNA, such as site 1 and/or site 2 in the 3'-UTR of an importin-α3 mRNA as shown in FIG. 8A) or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin, or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering RNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., *Science* 296:550-553, 2002; Lee et al, *Nature Biotechnol.* 20:500-505, 2002; Miyagishi and Taira, *Nature Biotechnol.* 20:497-500, 2002; Paddison et al., *Genes & Dev.* 16:948-958, 2002; Paul, *Nature Biotechnol.* 20:505-508, 2002; Sui, *Proc. Natl. Acad. Soc. U.S.A.* 99(6):5515-5520, 2002; Yu et al., *Proc. Natl. Acad. Sci. U.S.A.* 99:6047-6052, 2002.

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the provided methods have the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target (e.g., an importin-α3 mRNA).

Ribozymes

Trans-cleaving enzymatic nucleic acid molecules can also be used; they have shown promise as therapeutic agents for human disease (Usman & McSwiggen, *Ann. Rep. Med. Chem.* 30:285-294, 1995; Christoffersen and Marr, *J. Med. Chem.* 38:2023-2037, 1995). Enzymatic nucleic acid molecules can be designed to cleave an importin-α3 mRNA within the background of cellular RNA. Such a cleavage event renders the importin-α3 mRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein (an importin-α3 protein). After an enzymatic nucleic acid has bound and cleaved its RNA target, it is released from that RNA to search for another target and can repeatedly bind and cleave new targets.

Several approaches such as in vitro selection (evolution) strategies (Orgel, *Proc. R. Soc. London, B* 205:435, 1979) have been used to evolve new nucleic acid catalysts capable of catalyzing a variety of reactions, such as cleavage and ligation of phosphodiester linkages and amide linkages (Joyce, *Gene,* 82:83-87, 1989; Beaudry et al., *Science* 257:635-641, 1992; Joyce, *Scientific American* 267:90-97, 1992; Breaker et al., *TIBTECH* 12:268. 1994; Bartel et al., *Science* 261:1411-1418, 1993; Szostak, *TIBS* 17:89-93, 1993; Kumar et al., *FASEB J.,* 9:1183, 1995; Breaker, *Curr. Op. Biotech.* 1:442, 1996).

Making and Using the Nucleic Acids

The nucleic acids used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including, for e.g., in vitro bacterial, fungal, mammalian, yeast, insect, or plant cell expression systems. Nucleic acid sequences that can be used in any of the methods described herein can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example, as described in Sambrook et al., Molecular Cloning: A Laboratory Manual., 1989; Coffin et al., Retroviruses, 1997; and "RNA Viruses: A Practical Approach" (Alan J. Cann, Ed., Oxford University Press, 2000). As will be apparent to one of ordinary skill in the art, a variety of suitable vectors are available for transferring nucleic acids (e.g., a nucleic acid containing all or a part of SEQ ID NO: 1) into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids (e.g., a sequence containing all or a part of SEQ ID NO: 1) can be constructed based on viral backbones including, but not limited to, a retrovirus, lentivirus, adenovirus, adeno-associated virus, pox virus, or alphavirus. The recombinant vectors capable of expressing a nucleic acid (e.g., a nucleic acid containing all or part of SEQ ID NO: 1) can be delivered as described herein, and persist in target cells (e.g., stable transformants).

Nucleic acid sequences containing all or a part of SEQ ID NO: 1 can be synthesized in vitro by well-known chemical synthesis techniques, as described in, e.g., Adams, *J. Am. Chem. Soc.* 105:661, 1983; Belousov, *Nucleic Acids Res.* 25:3440-3444, 1997; Frenkel, *Free Radic. Biol. Med.* 19:373-380, 1995; Blommers, *Biochemistry* 33:7886-7896, 1994; Narang, *Meth. Enzymol.* 68:90, 1979; Brown, *Meth. Enzymol.* 68:109, 1979; Beaucage, *Tetra. Lett.* 22:1859, 1981; and U.S. Pat. No. 4,458,066.

Nucleic acid sequences containing all or a part of SEQ ID NO: 1 can be stabilized against nucleolytic degradation such as by the incorporation of a modification, e.g., a nucleotide modification. For example, nucleic acid sequences (e.g., nucleic acids including all or a part of SEQ ID NO: 1) can include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., *Drug Disc. Today* 2(3):287-290, 2005; Koshkin et al., *J. Am. Chem. Soc.* 120 (50):13252-13253, 1998). For additional modifications see US 2010/0004320, US 2009/0298916, and US 2009/0143326.

Techniques for the manipulation of nucleic acids used to practice this invention, such as, e.g., subcloning, labeling probes (e.g., random-primer labeling using Klenow polymerase, nick translation, and amplification), sequencing, hybridization, and the like are well described in the scientific and patent literature, see, e.g., Sambrook et al., Molecular Cloning; A Laboratory Manual 3d ed., 2001; Current Protocols in Molecular Biology, Ausubel et al., Eds. (John Wiley & Sons, Inc., New York, 2010); Kriegler, Gene Transfer and Expression: A Laboratory Manual, 1990; Laboratory Techniques in Biochemistry and Molecular Biology: Hybridization with Nucleic Acid Probes, Part I. Theory and Nucleic Acid Preparation, Tijssen, Ed., Elsevier, N.Y., 1993.

Pharmaceutical Compositions

The methods described herein can include the administration of pharmaceutical compositions and formulations comprising the nucleic acid sequences described herein (e.g., nucleic acids containing all or a part of the sequence of SEQ ID NO: 1).

In some embodiments, the compositions are formulated with a pharmaceutically acceptable carrier. The pharmaceutical compositions and formulations can be administered parenterally, intramuscularly, subcutaneously, arterially, intravenously, topically, orally, or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The nucleic acids can be administered alone or as a component of a pharmaceutical formulation (composition). The compounds may be formulated for administration, in any convenient way for use in human or veterinary medicine. Wetting agents, emulsifiers, and lubricants, such as sodium lauryl sulfate and magnesium stearate, as well as coloring agents, release agents, coating agents, sweetening, flavoring, perfuming agents, preservatives, and antioxidants can also be present in the compositions. Formulations of the compositions that may be used in the methods described herein include those suitable for intradermal, inhalation, intramuscular, subcutaneous, arterial, intravenous, oral/nasal, topical, parenteral, rectal, and/or intravaginal administration. The formulations may conveniently be presented in unit dosage form and may be prepared by any methods well known in the art of pharmacy. The amount of active ingredient (e.g., a nucleic acid sequence described herein) which can be combined with a carrier material to produce a single dosage form will vary depending upon the host being treated, the particular mode of administration, e.g., intravenous or inhalation. The amount of active ingredient which can be combined with a carrier material to produce a single dosage form will generally be that amount of the compound which produces a therapeutic effect Pharmaceutical formulations of this invention can be prepared according to any method known to the art for the manufacture of pharmaceuticals. Such drugs can contain sweetening agents, flavoring agents, coloring agents, and preserving agents. A formulation can be admixed with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences containing all or a part of SEQ ID NO: 1) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and a dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame, or saccharin. Formulations can be adjusted for osmolarity.

In some embodiments, oil-based pharmaceuticals are used for administration of nucleic acid sequences (e.g., nucleic acid sequences containing all or a part of SEQ ID NO: 1). Oil-based suspensions can be formulated by suspending an active agent in a vegetable oil, such as arachis oil, olive oil, sesame oil, or coconut oil, or in a mineral oil such as liquid paraffin; or a mixture of these. See e.g., U.S. Pat. No. 5,716,928, describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin, or cetyl alcohol. Sweetening agents can be added to provide a palatable oral preparation, such as glycerol, sorbitol, or sucrose. These formulations can be preserved by the addition of an antioxidant such as ascorbic acid. As an example of an injectable oil vehicle, see Minto, *J. Pharmacol. Exp. Ther.* 281:93-102, 1997.

Pharmaceutical formulations can also be in the form of oil-in-water emulsions. The oily phase can be a vegetable oil or a mineral oil, described herein, or a mixture of these. Suitable emulsifying agents include naturally-occurring gums, such as gum acacia and gum tragacanth, naturally-occurring phosphatides, such as soybean lecithin, esters, or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, the injectable oil-in-water emulsions that may be used in the methods described herein comprise a paraffin oil, a sorbitan monooleate, an ethoxylated sorbitan monooleate, and/or an ethoxylated sorbitan trioleate.

The pharmaceutical compounds can also be administered by in intranasal, intraocular, and intravaginal routes including suppositories, insufflation, powders, and aerosol formulations (for examples of inhalants, see e.g., Rohatagi, *J. Clin. Pharmacol.* 35:1187-1193, 1995; Tjwa, *Ann. Allergy Asthma Immunol.* 75:107-111, 1995). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols. In some embodiments, the pharmaceutical compounds can also be delivered as microspheres for slow release in the body. For example, microspheres can be administered via intradermal injection of drug which slowly release subcutaneously; see Rao, *J. Biomater. Sci. Polym. Ed.* 7:623-645, 1995; as biodegradable and injectable gel formulations, see, e.g., Gao, *Pharm. Res.* 12:857-863, 1995; or as microspheres for oral administration, see, e.g., Eyles, *J. Pharm. Pharmacol.* 49:669-674, 1997.

In some embodiments, the pharmaceutical compounds can be parenterally administered, such as by intravenous (IV) administration or administration into a body cavity or lumen of an organ (e.g., into the lung). These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well-known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising a nucleic acid can be made by lyophilizing a solution comprising a pharmaceutical described herein (e.g., containing a nucleic acid containing all or a part of SEQ ID NO: 1) and a bulking agent, e.g., mannitol, trehalose, raffinose, and sucrose, or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5, but less than 6.5. See, e.g., US 2004/0028670. The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400 and 6,007,839; Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively-charged liposomes that are believed to interact with negatively-charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically-stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically-stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

Methods of Treating a Vascular Inflammatory Disease

Provided herein are methods of treating or delaying the onset of a vascular inflammatory disease in a subject including administering to the subject a nucleic acid containing all or a part of the sequence of mature miR-181b (SEQ ID NO: 1) (e.g., a sequence containing SEQ ID NO: 2 or SEQ ID NO: 3).

Subject that may be treated by the methods of the present invention may have been previously diagnosed as having a vascular inflammatory disease, may present with one or more (e.g., two, three, four, or five) symptoms of a vascular inflammatory disease, may have an increased risk of developing a vascular inflammatory disease, may be admitted in a medical facility (e.g., an intensive care unit), may be in an early stage of a vascular inflammatory disease, may be in a late stage of a vascular inflammatory disease, or may have or be suspected of having a bacterial infection. The subject may be a male, a female, a child, or an infant.

The subject may begin to receive treatment within at least 48 hours, 36 hours, 24 hours, 20 hours, 16 hours, 12 hours, 10 hours, or 6 hours of presentation to a health care professional or a medical facility. In some examples, the subject may already be admitted to a health care facility and is diagnosed as having a bacterial infection or is suspected of having a bacterial infection. The subject may receive treatment prior to the presentation of any symptoms, prior to a diagnosis of having a vascular inflammatory disease, upon indication that subject has an increased risk of developing a vascular inflammatory disease, at an intermediate stage of the disease (e.g., upon presentation of one or more symptoms of a vascular inflammatory disease), at a late stage of the disease (e.g., upon presentation of one or more severe symptoms of a vascular inflammatory disease that may require admission into a medical care facility), following diagnosis of a bacterial infection, or upon presenting with one or more symptoms which suggest the subject may have a bacterial infection. The treatment may be performed by a health care professional (e.g., a physician, a nurse, and a physician's assistant) or by the subject.

A health care professional may assess the effect of the treatment by observing or measuring one or more (e.g., two, three, four, or five) symptoms of a vascular inflammatory disease in a subject. Non-limiting symptoms of vascular inflammatory diseases are described herein and may be measured by physical examination. Additional molecular methods for determining the severity of a vascular inflammatory disease are known in the art and may also be used to assess the efficacy of treatment in a subject (e.g., serum levels of C-reactive protein and inflammatory cytokines, such as TNF-α or IL-1). The health care professional may adjust the frequency, dosage, or duration of treatment based on the assessment and measuring of one or more (e.g., two, three, four, or five) symptoms of a vascular inflammatory disease in a subject during treatment.

A nucleic acid (e.g., a nucleic acid containing all or a part of the sequence of SEQ ID NO: 1) can be administered for prophylactic and/or therapeutic treatments. In some embodiments, for therapeutic applications, compositions are administered to a subject having a vascular inflammatory disorder, or a subject who is at risk of developing a vascular inflammatory disorder, in an amount sufficient to reduce (the number, severity, and/or duration), or partially arrest, one or more symptoms (e.g., two, three, four, five, or six) of a vascular inflammatory disorder; this can be called a therapeutically effective amount. For example, in some embodiments, pharmaceutical compositions (e.g., compositions containing a nucleic acid containing all or a part of SEQ ID NO: 1) are administered in an amount sufficient to decrease (e.g., a significant decrease, such as by at least 5%, 10%, 15%, 20%, 25%, 30%, 35%, 40%, 45%, 50%, 55%, 60%, 65%, 70%, 75%, 80%, 85%, 90%, or 95%) leukocyte adhesion to the subject's endothelium, decrease (e.g., a significant decrease, such as by at least 5%, 10%, 15%, 20%, 25%, 30%, 35%, 40%, 45%, 50%, 55%, 60%, 65%, 70%, 75%, 80%, 85%, 90%, or 95%) leukocyte extravasion of the subject's endothelium, decrease (e.g., a significant decrease, such as by at least 5%, 10%, 15%, 20%, 25%, 30%, 35%, 40%, 45%, 50%, 55%, 60%, 65%, 70%, 75%, 80%, 85%, 90%, or 95%) the expression (protein or mRNA) of VCAM-1, E-selectin, and/or ICAM-1 in the subject's endothelium, (e.g., a significant decrease, such as by at least 5%, 10%, 15%, 20%, 25%, 30%, 35%, 40%, 45%, 50%, 55%, 60%, 65%, 70%, 75%, 80%, 85%, 90%, or 95%) reduce expression (protein or mRNA) of importin-α3 in the subject's endothelium, and/or decrease (e.g., a significant decrease, such as by at least 5%, 10%, 15%, 20%, 25%, 30%, 35%, 40%, 45%, 50%, 55%, 60%, 65%, 70%, 75%, 80%, 85%, 90%, or 95%) import of the p65 and/or p50 subunit of NF-κB into the nucleus of a endothelial cell in the subject compared to a control subject (e.g., a subject not administered the nucleic acid or the same subject prior to treatment with the nucleic acid).

The amount of the nucleic acid adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age, and the like. In calculating the dosage regimen for a patient, the mode of administration also is taken into consideration.

The dosage regimen also takes into consideration pharmacokinetics parameters well known in the art, i.e., the active agent's rate of absorption, bioavailability, metabolism, clearance, and the like (see, e.g., Hidalgo-Aragones, *J. Steroid Biochem. Mol. Biol.* 58:611-617, 1996; Groning, *Pharmazie* 51:337-341, 1996; Fotherby, *Contraception* 54:59-69, 1996; Johnson, *J. Pharm. Sci.* 84:1144-1146, 1995; Rohatagi, *Pharmazie* 50:610-613, 1995; Brophy, *Eur. J. Clin. Pharmacol.* 24:103-108, 1983; Remington: The Science and Practice of Pharmacy, 21st ed., 2005). The state of the art allows the heath care professional to determine the dosage regimen for each individual patient, active agent, and disease or condition treated. Guidelines provided for similar compositions used as pharmaceuticals can be used as guidance to determine the dosage regiment, i.e., dose schedule and dosage levels, administered practicing the methods described herein are correct and appropriate.

Single or multiple administrations of formulations can be given depending on for example: the dosage and frequency as required and tolerated by the patient, the degree and amount of therapeutic effect generated after each administration (e.g., effect on one or more symptoms of a vascular inflammatory disease), and the like. The formulations should provide a sufficient quantity of active agent to effectively treat, ameliorate, or delay the onset of a vascular inflammatory disease or one or more (e.g., two, three, four, five, or six) of its symptoms.

One or more (e.g., two, three, four, or five) nucleic acids described herein and, optionally, one or more (e.g., two, three, four, or five) additional anti-inflammatory agents (described below) can be administered parenterally, intramuscularly, subcutaneously, arterially, intravenously, topically, orally, or by local administration, such as by aerosol or transdermally, to the subject.

The subject may be administered the nucleic acid once a day, twice a day, three times a day, four times a day, once a week, twice a week, three times a week, four times a week, once a month, twice a month, three times a month, four times a month, five times a month, six times a month, seven times a month, eight times a month, bimonthly, once a year, twice a year, three times a year, or four times a year. A subject may be administered the nucleic acid continuously (e.g., for at least 5 minutes, 10 minutes, 30 minutes, 1 hour, 2 hours, 3 hours, 4 hours, 8 hours, 12 hours, 24 hours, 36 hours, 48 hours, or 1 week) via intravenous administration.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ (e.g., into the lung). For example, a dose of about 0.1 to 80, 0.1 to 70, 0.1 to 60, 0.1 to 50, 1 to 40, 1 to 30, 1 to 20, 0.1 to 15, 0.1 to 10, or 0.1 to 5 mg per kg of body weight per day may be administered to the subject. Substantially higher dosages can be used in topical or oral administration or administering by powders, spray, or inhalation. Actual methods for preparing parenterally or non-parenterally administrable formulations will be known or apparent to those skilled in the art and are described in more detail in such publications as Remington: The Science and Practice of Pharmacy, 21st ed., 2005.

Various studies, including the animal model data provided herein, have reported successful mammalian dosing using nucleic acid sequences. For example, Esau C., et al., *Cell Metabolism*, 3(2):87-98, 2006, reported dosing of normal mice with intraperitoneal doses of an miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., *Nature* 438, 685-689, 2005, injected a nucleic acid to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen et al., *Nature* 452, 896-899, 2008, report that efficient silencing of miR-122 was achieved in primates by three doses of 10 mg per kg LNA-anti-miR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., one or more (e.g., two, three, four, or five) additional anti-inflammatory agents (e.g., corticosteroids, immunosuppressive agents, TNF-α antagonists, such as etanercept, infliximab, or adalimumab, and IL-1 antagonists, such as anakinra). For example, the provided nucleic acids can be co-administered with additional agents for treating or reducing risk of developing a vascular inflammatory disease described herein. Several agents useful for the treatment of a vascular inflammatory disease are known in the art.

The one or more additional anti-inflammatory agents may be administered to the subject in a dose of between 0.1 to 100, 0.1 to 80, 0.1 to 70, 0.1 to 60, 0.1 to 50, 1 to 40, 1 to 30, 1 to 20, 0.1 to 15, 0.1 to 10, or 0.1 to 5 mg per kg of body weight per day, depending on the specific agent and the route of administration. The one or more additional anti-inflammatory agents may be formulated together with the one or more nucleic acids described herein in a single dosage form (e.g., an aerosol for inhalation, a solid form for oral administration, or as a solution for intravenous administration). In some embodiments, the one or more nucleic acids described herein (e.g., a nucleic acid containing all or a part of SEQ ID NO: 1) may be administered in a separate dosage form from the one or more additional anti-inflammatory agents. In some embodiments, the subject is first administered at least one dose of an additional anti-inflammatory agent prior to the administration of at least one dose of the nucleic acids described herein. In some embodiments, the subject is first administered at least one dose of the nucleic acids described herein prior to the administration of at least one dose of an additional anti-inflammatory agent. In some embodiments, the bioactive periods of the nucleic acid and the additional anti-inflammatory agent overlap in the subject.

Methods of Decreasing NF-kB Signaling in a Cell

Also provided are methods for decreasing NF-κB signaling in a cell (e.g., an endothelial cell) by administering at least one nucleic acid that contains all or a part of the sequence of mature miR-181b (SEQ ID NO: 1). The cell (e.g., an endothelial cell) may be present in a subject or may be a cell (e.g., an endothelial cell) that is present in vitro (tissue culture) or a cell that is removed from a subject and grown in tissue culture (e.g., an ex vivo endothelial cell).

Cell in a Subject

In some embodiments, the cell (e.g., endothelial cell) is in a subject. For example, a health care professional may determine that a subject has or may have an increased level of NF-κB signaling that contributes to a pathophysiological condition in the subject (e.g., one or more of the diseases, e.g., a vascular inflammatory disease, described herein). In such instances, a health care professional may prescribe treatment of the subject according to the provided methods. The subject may be presenting with one or more symptoms of such a condition (e.g., a vascular inflammatory disease), may have been previously diagnosed as having such a condition (e.g., a vascular inflammatory disease), may be asymptomatic but at increased risk of later developing such a condition (e.g., a vascular inflammatory disease), may be in an early stage of the disease (e.g., a vascular inflammatory disease), may in a late stage of the disease (e.g., a vascular inflammatory disease), may be admitted in a medical facility (e.g., a hospital, an intensive care unit, or an assisted care facility), may be diagnosed as having a bacterial infection, or may be suspected of having a bacterial infection. The subject may also present with one or more (e.g., two, three, four, or five) of the following features: increased (e.g., a significant increase, such an increase of at least 5%, 10%, 15%, 20%, 25%, 30%, 35%, 40%, 45%, 50%, 60%, 65%, 70%, 75%, 80%, 85%, 90%, 95%, or 100%) leukocyte adhesion to the subject's endothelium, increased (e.g., a significant increase, such an increase of at least 5%, 10%, 15%, 20%, 25%, 30%, 35%, 40%, 45%, 50%, 60%, 65%, 70%, 75%, 80%, 85%, 90%, 95%, or 100%) leukocyte extravasation of the subject's endothelium, increased (e.g., a significant increase, such an increase of at least 5%, 10%, 15%, 20%, 25%, 30%, 35%, 40%, 45%, 50%, 60%, 65%, 70%, 75%, 80%, 85%, 90%, 95%, or 100%) expression (protein or mRNA) of one or more of VCAM-1, E-selectin, and ICAM-1 in the endothelium, increased (e.g., a significant increase, such an increase of at least 5%, 10%, 15%, 20%, 25%, 30%, 35%, 40%, 45%, 50%, 60%, 65%, 70%, 75%, 80%, 85%, 90%, 95%, or 100%) expression (protein or mRNA) of one or more genes regulated by NF-κB activity, increased (e.g., a significant increase, such an increase of at least 5%, 10%, 15%, 20%, 25%, 30%, 35%, 40%, 45%, 50%, 60%, 65%, 70%, 75%, 80%, 85%, 90%, 95%, or 100%) levels of pro-inflammatory cytokines (e.g., IL-1 and TNF-α), and increased (e.g., a significant increase, such an increase of at least 5%, 10%, 15%, 20%, 25%, 30%, 35%, 40%, 45%, 50%, 60%, 65%, 70%, 75%, 80%, 85%, 90%, 95%, or 100%) levels of C-reactive protein. The subject may be a male, a female, a child, or an infant.

The subject may begin to receive treatment within at least 48 hours, 36 hours, 24 hours, 20 hours, 16 hours, 12 hours, 10 hours, or 6 hours of presentation to a health care professional or a medical facility. The subject may receive treatment prior to the presentation of any symptoms, prior to a diagnosis of having a disease (e.g., a vascular inflammatory disease), upon indication that subject has an increased risk of developing a disease (e.g., a vascular inflammatory disease), at an intermediate stage of the disease (e.g., following diagnosis or upon presentation of one or more symptoms of a vascular inflammatory disease), at a late stage of the disease (e.g., upon presentation of one or more severe symptoms of a vascular inflammatory disease that may require admission into a medical care facility), following diagnosis of a bacterial infection, or upon suspicion of having a bacterial infection. The treatment may be performed by a health care professional (e.g., a physician, a nurse, and a physician's assistant) or by the subject.

A health care professional may assess the effect of the treatment by observing or measuring one or more (e.g., two, three, four, or five) symptoms of a disease (e.g., a vascular inflammatory disease) in a subject. Non-limiting symptoms of vascular inflammatory diseases are described herein and may be measured by physical examination. Additional molecular methods for determining the severity of a disease (e.g., a vascular inflammatory disease) are known in the art and may also be used to assess the efficacy of treatment in a subject (e.g., serum levels of C-reactive protein and pro-inflammatory cytokines, such as IL-1 and TNF-α). In addition, the efficacy of treatment may be assessed by determining whether there is: a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in leukocyte adhesion in the subject's endothelium, a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in leukocyte extravasation of the subject's endothelium, a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in NF-κB-induced gene expression, a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in the expression levels (protein or mRNA) of importin-α3, a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in the expression levels (protein or mRNA) of one or more of ICAM-1, VCAM-1, and E-selectin, or a decrease (a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in the expression (protein or mRNA) of one or more of the genes listed in FIG. 9A, as compared to control subject not receiving the nucleic acid (e.g., a subject not diagnosed or not presenting with one or more symptoms of a vascular inflammatory disease or the same subject prior to administration of the nucleic acid). The health care professional may adjust the frequency, dosage, or duration of treatment based on the assessment and measuring of one or more (e.g., two, three, four, or five) symptoms of a disease (e.g., a vascular inflammatory disease) in a subject during treatment.

Any of the nucleic acids described herein may be administered in these methods. In addition, any of the dosing and administration schedules described herein may be used in these methods. As described herein, in addition to administering one or more of the nucleic acids described herein, one or more anti-inflammatory agents may also be administered to the subject. Any of the formulations, compositions, administration schedules, and dosing described herein may be used in these methods without limitation.

Cell In Vitro and Ex Vivo

As indicated above, the cell (e.g., an endothelial cell) administered a nucleic acid containing all or a part of the sequence of mature miR-181b (SEQ ID NO: 1) may be present in vivo or may have previously been removed from a subject and treated with the nucleic acid in tissue culture (ex vivo). A cell (e.g., an endothelial cell) removed from the subject and administered the nucleic acid in tissue culture may be implanted into a subject following said administration. For example, the removed cell (e.g., endothelial cell) may be cultured in the presence of the nucleic acid for at least 6 hours, 12 hours, 18 hours, 24 hours, 48 hours, 3 days, 4 days, 5 days, 6 days, or 1 week before implanting the cell back into the subject. The cell removed from the subject may also be transfected with another nucleic acid to induce expression of a therapeutic protein (e.g., a protein that decreases inflammation in a subject).

One skilled in the art would readily be able to determine the amount of the nucleic acid required to affect a decrease in NF-κB signaling in the cell (e.g., endothelial cell). Exemplary methods are described in the specification and are known in the art. For example, a decrease in NF-κB signaling may be observed by a: decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in NF-κB-induced gene expression, a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in nuclear translocation of NF-κB, and a decrease (e.g., a significant decrease, such a decrease of at least 5%, 10%, 15%, 20%, 25%, 30%, 35%, 40%, 45%, 50%, 60%, 65%, 70%, 75%, 80%, 85%, 90%, or 95%) in NF-κB binding to its promoter elements compared to control cells (e.g., control cells treated with an agent that stimulates NF-κB signaling activity, such as TNF-α).

Any of the nucleic acids or compositions described herein may be used in these methods.

EXAMPLES

The invention is further described in the following examples, which do not limit the scope of the invention described in the claims.

Example 1

MiR-181b is a Critical Regulator of NF-κB-Mediated Endothelial Cell Activation and Vascular Inflammation In Vivo MiR-181b Expression in Endothelial Cells is Regulated by TNF-α.

In an attempt to identify how pro-inflammatory stimuli regulate endothelial function, microarray miR profiling studies were undertaken using RNA from HUVECs exposed to vehicle alone or TNF-α for 24 h. Increased expression of miR-181b was observed in association with TNF-α treatment in HUVECs. Using real-time PCR analysis, the induction of miR-181b in HUVECs in response to TNF-α exposure was verified: an increase in expression by about 1.3-fold at 24 h (FIG. 1A). Surprisingly, earlier time points (at 1 and 4 h) revealed that TNF-α inhibited miR-181b expression by 31% and 24%, respectively (FIG. 1A).

Figure 1B:
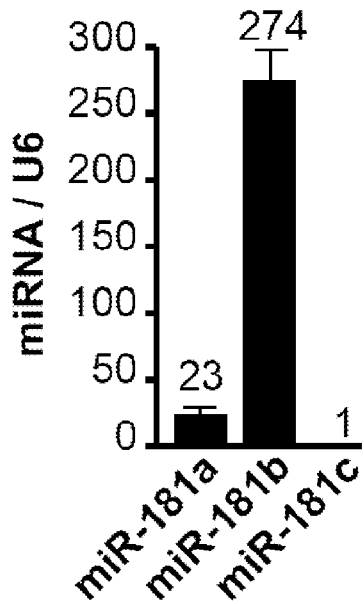

MiR-181b belongs to the miR-181 family, which is comprised of four mature miRNAs: miR-181a, miR-181b, miR-181c, and miR-181d. These mature sequences are encoded by six primary miRNA sequences located on three different chromosomes. The expression of miR-181b was determined to be about 12-fold higher than that of miR-181a, and 274-fold higher than that of miR-181c (FIG. 1B). Since the level of primary (pri)-miR-181d was very low, the level of this mature miR-181d was not examined. Collectively, these data suggest that miR-181b is the dominantly expressed miR-181 family member in HUVECs and that it has a bi-modal expression pattern in response to stimulation by the inflammatory cytokine TNF-α.

MiR-181b Inhibits TNF-α-Induced Expression of Adhesion Molecules and Inhibits Leukocyte Adhesion to Activated EC Monolayers.

Figure 1C:
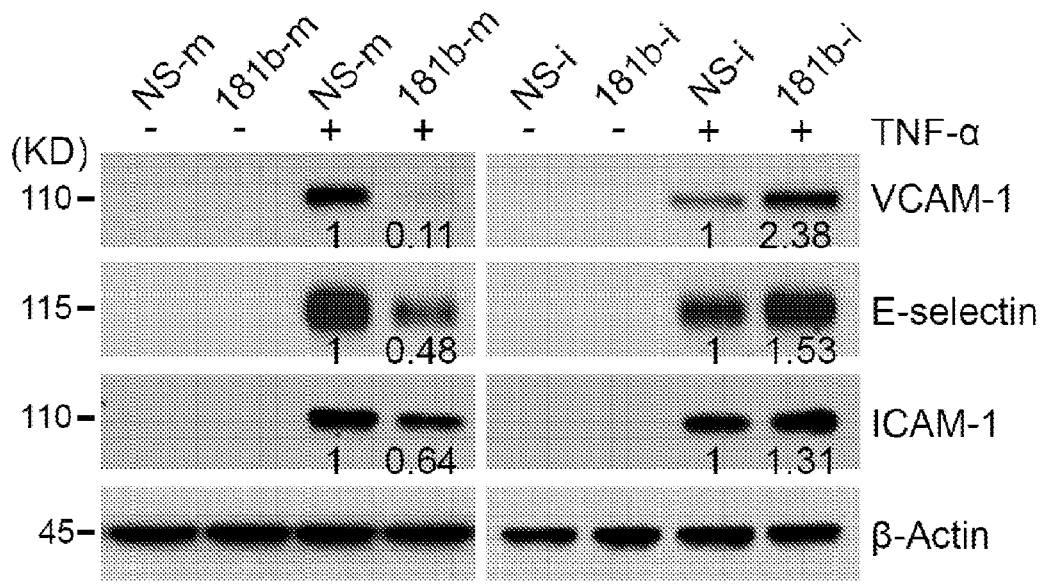
Figure 1D:
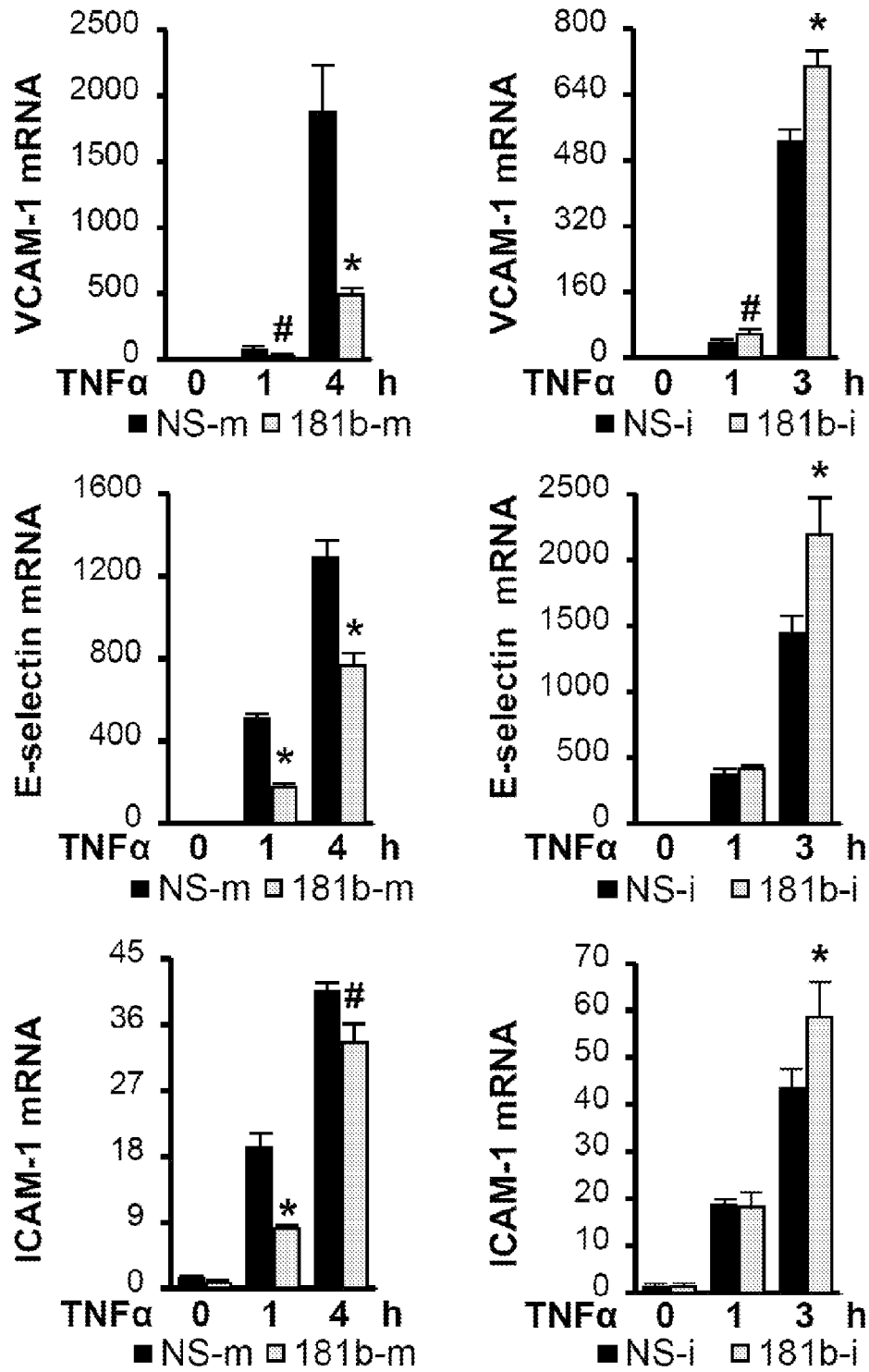
Figure 1E:
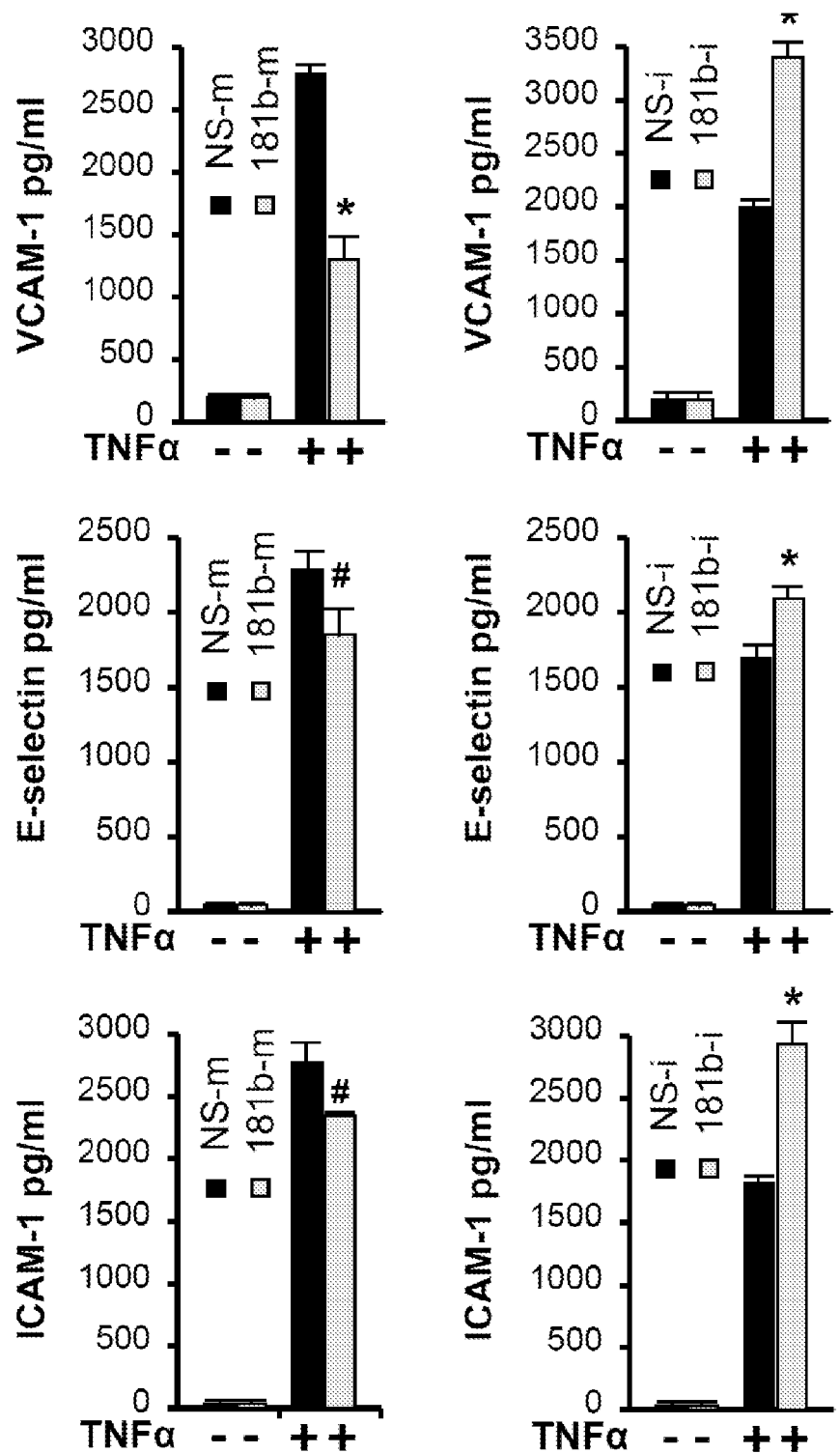

To assess the potential role of miR-181b in endothelial activation, the effect of miR-181b on TNF-α-induced gene expression was examined in HUVECs using gain- and loss-of-function experiments. Over-expression of miR-181b inhibited TNF-α-induced VCAM-1, E-selectin, and ICAM-1 protein expression by 89%, 52%, and 36%, respectively, while, miR-181b inhibitors (complementary antagonist) increased their expression by 138%, 53%, and 31%, respectively (FIG. 1C). Consistent with these results, the mRNA levels of VCAM-1, E-selectin, and ICAM-1 were lower in cells over-expressing miR-181b than in cells over-expressing the miRNA negative control; moreover, these mRNA levels were higher in the presence of the miR-181b inhibitor (FIG. 1D). After 1-h TNF-α treatment, cells over-expressing miR-181b exhibited reduced mRNA levels of VCAM-1, E-selectin, and ICAM-1 (by 69%, 65%, and 57%, respectively); after 4 h of TNF-α treatment, the levels were 74%, 41%, and 17%, respectively. In contrast, in cells transfected with miR-181b inhibitors, TNF-α-induced VCAM-1 mRNA was increased by 62% after 1-h TNF-α treatment, and after 3 h of TNF-α treatment, VCAM-1, E-selectin, and ICAM-1 mRNA levels were increased by 35%, 52%, and 34%, respectively (FIG. 1D). The effects of miR-181b on levels of soluble VCAM-1, E-selectin, and ICAM-1 in the culture medium, as measured by ELISA, were also consistent with its effects on the mRNA and protein expression of these adhesion molecules (FIG.

1E). Likewise, miR-181b also reduced VCAM-1 expression at both protein and mRNA level in HUVECs in response to LPS treatment (FIG. 2A-C) and the expression of E-selectin mRNA and ICAM-1 mRNA (FIG. 2C).

Considering the finding that VCAM-1 expression was most sensitive to miR-181b, experiments were performed to determine whether the VCAM-1 gene might be a direct target of the miR. However, over-expression of miR-181b did not reduce the luciferase activity of a VCAM-1 3'-UTR construct, suggesting that the VCAM-1 3'-UTR is not directly targeted by miR-181b (FIG. 2D). Since VCAM-1, E-selectin, and ICAM-1 are typical pro-inflammatory molecules induced by TNF-α, these data suggested that miR-181b may be involved in the regulation of endothelial cell activation. To investigate whether miR-181a, the next highest expressed miR-181 family member in HUVECs, was able to elicit the same effect on TNF-α-induced gene expression as miR-181b did, HUVECs were transfected with miRNA negative control, miR-181a, or miR-181b at different concentrations in the presence or absence of TNF-α, and harvested for Western blot analysis of VCAM-1 expression. As shown in FIG. 2E, miR-181a inhibited TNF-α-induced VCAM-1 expression to a lesser extent than miR-181b at all concentrations examined.

Figure 1F:
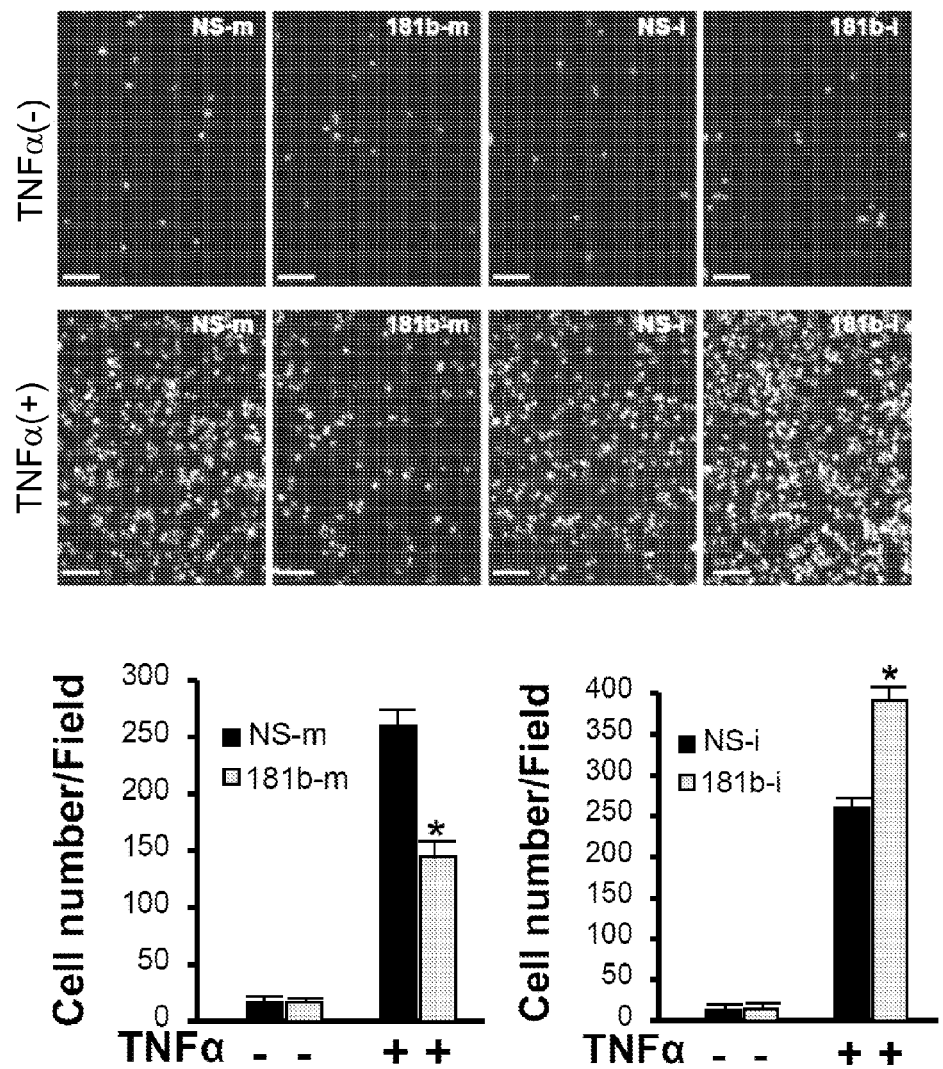

In response to endothelial cell activation, adhesion molecules, such as VCAM-1, E-selectin, and ICAM-1, act to initiate, promote, and sustain leukocyte attachment to the vascular endothelium. To determine the functional consequence of miR-181b effects on adhesion molecule expression, in vitro cell adhesion assays were performed to assess leukocyte-endothelial cell interactions. As expected, TNF-α treatment markedly increased the adhesion capabilities of THP-1 cells to HUVECs transfected with non-specific (NS) control miRNA mimics. However, adhesion was markedly reduced (by 44%) with miR-181b over-expression, whereas inhibition of miR-181b increased the adherence by 50% (FIG. 1F). Taken together, these findings show that miR-181b is able to negatively affect the expression of key adhesion molecules induced by pro-inflammatory stimuli and that miR-181b dynamically regulates leukocyte adhesion to stimulated EC monolayers.

MiR-181b Suppresses TNF-α-Induced Expression of Adhesion Molecules In Vivo.

Figure 3A:
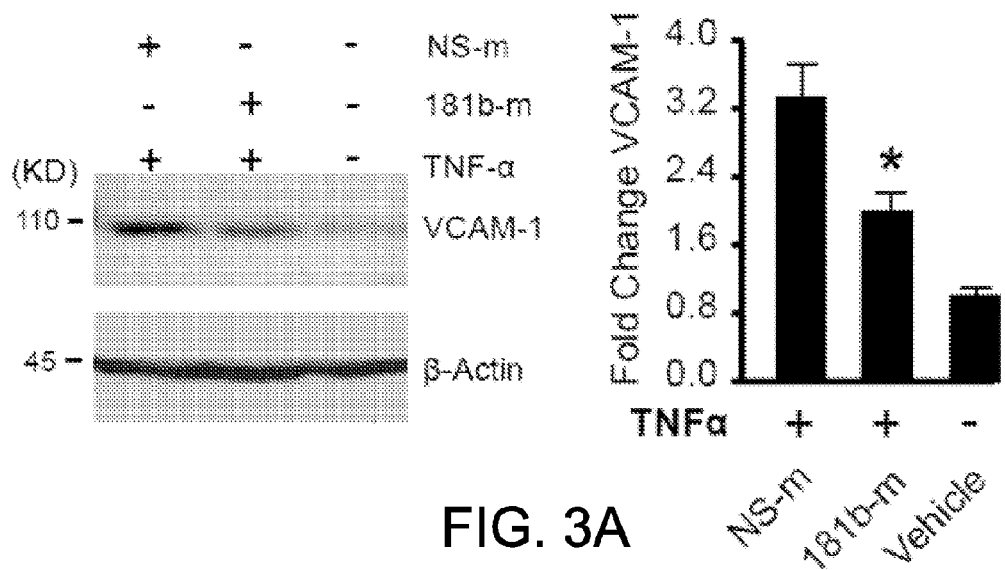
Figure 3B:
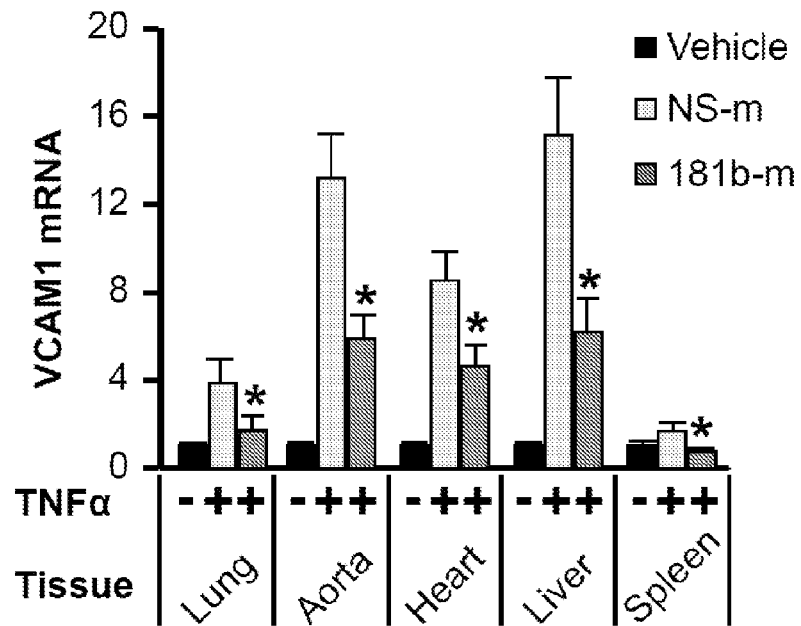
Figure 4B:
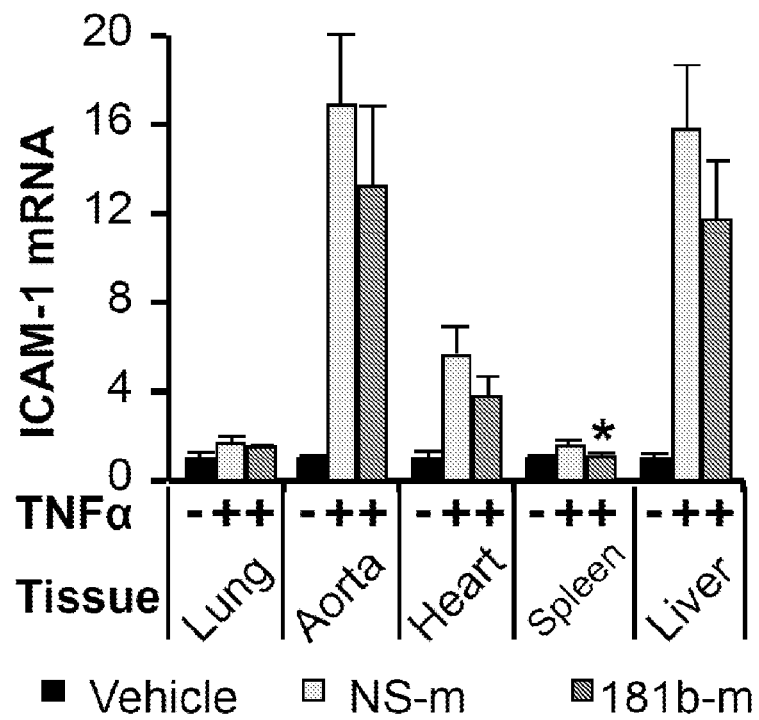

Experiments were performed to determine whether systemic administration of miR-181b could inhibit TNF-α-induced gene expression in vivo. Atelocollagen, a highly purified bovine type I collagen without immunogenicity, has been successfully used to deliver plasmid DNA, siRNA, and miR-NAs into cells in vitro and in vivo (Ochiya et al., *Nature Med.* 5:707-710, 1999; Sano et al., *Adv. Drug Deliv. Rev.* 55:1651-1677, 2003; Takeshita et al., *Methods Mol. Biol.* 487:83-92, 2009; Takeshita et al., *Proc. Natl. Acad. Sci. U.S.A.* 102:12177-12182, 2005; Takeshita et al., *Mol. Ther.* 18:181-187, 2010; Tazawa et al., *Proc. Natl. Acad. Sci. U.S.A.* 104:15472-15477, 2007). To assess the effects of miR-181b mimics on TNF-α-induced expression of VCAM-1 in vivo, miR-181b or a non-specific control mimic, was admixed with atelocollagen and tail vein-injected 24 h prior to TNF-α treatment. VCAM-1 protein expression was first examined in lung tissues. At 4 h after TNF-α i.p. injection, VCAM-1 was found to be induced by ~3.4-fold in lung tissues in the presence of non-specific control mimics. In contrast, administration of miR-181b potently reduced the induction of VCAM-1 protein expression (to ~2-fold) (FIG. 3A) and VCAM-1 mRNA expression in lung, aorta, heart, liver, and spleen (FIG. 3B). The expression of E-selectin mRNA was also significantly reduced in lung, liver, and spleen (FIG. 4A), whereas ICAM-1 mRNA was reduced only in spleen (FIG. 4B).

Figure 3C:
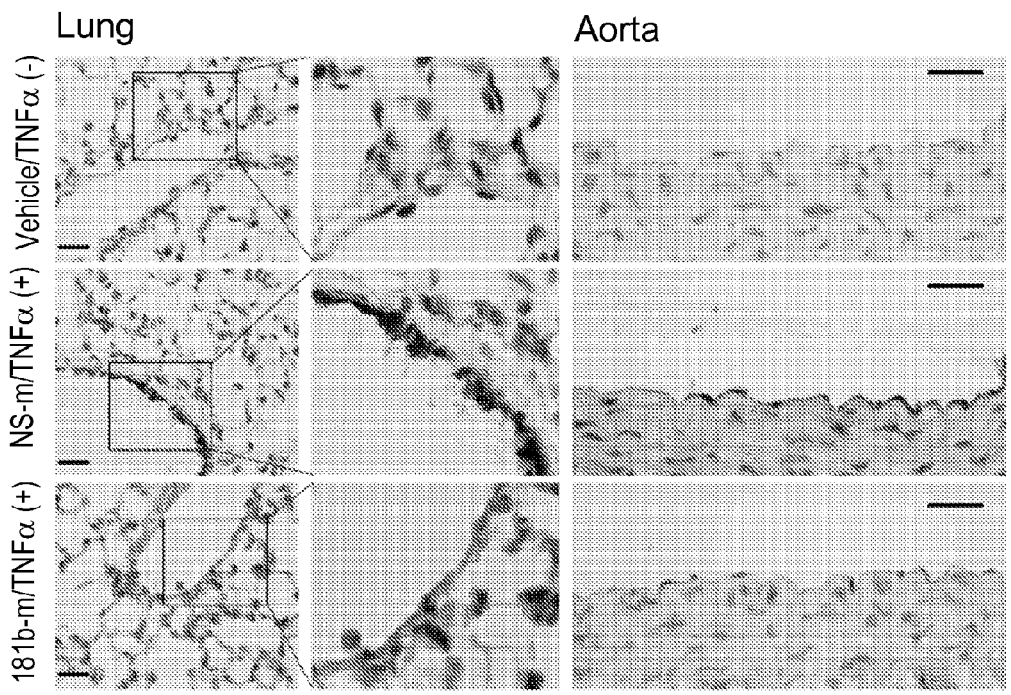
Figure 4C:
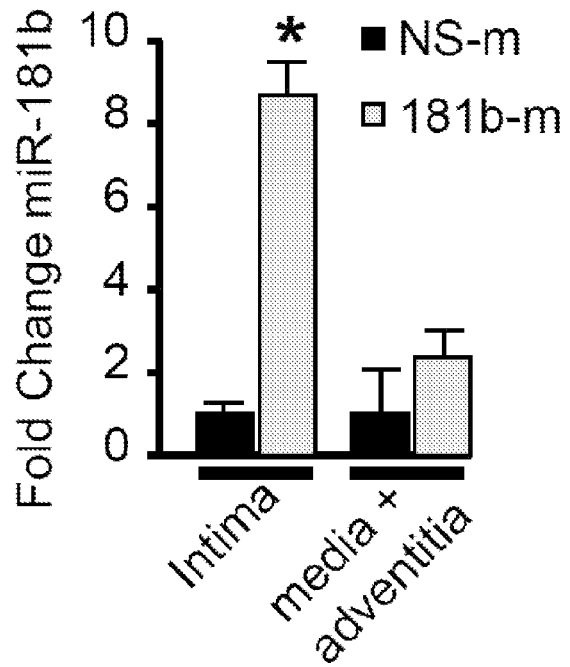

To further verify the observed effects on VCAM-1 expression, sections of lung and descending aorta were examined by immunohistochemical techniques. The endothelium of lung and aorta from mice injected with miRNA negative control displayed robust VCAM-1 expression in response to TNF-α (FIG. 3C-E). In contrast, systemic administration of miR-181b mimics reduced the induction of VCAM-1 expression in the endothelium in lung and aorta (by ~86% and ~80%, respectively) (FIG. 3C-E). Notably, the expression of miR-181b in the intima of aortae excised from mice injected with miR-181b was ~8-fold higher than in mice injected with miRNA negative control, as measured by real-time qPCR (FIG. 4C). There were no significant differences of miR-181b expression levels in the media and adventitia excised from mice injected with miR-181b or miRNA negative control (FIG. 4C). In summary, these data demonstrated that systemically administered miR-181b mimics were efficiently enriched in endothelial cells, and inhibited expression of TNF-α-induced adhesion molecules in vivo.

MiR-181b Inhibits the NF-κB Signaling Pathway in Activated Endothelial Cells.

Figure 5A:
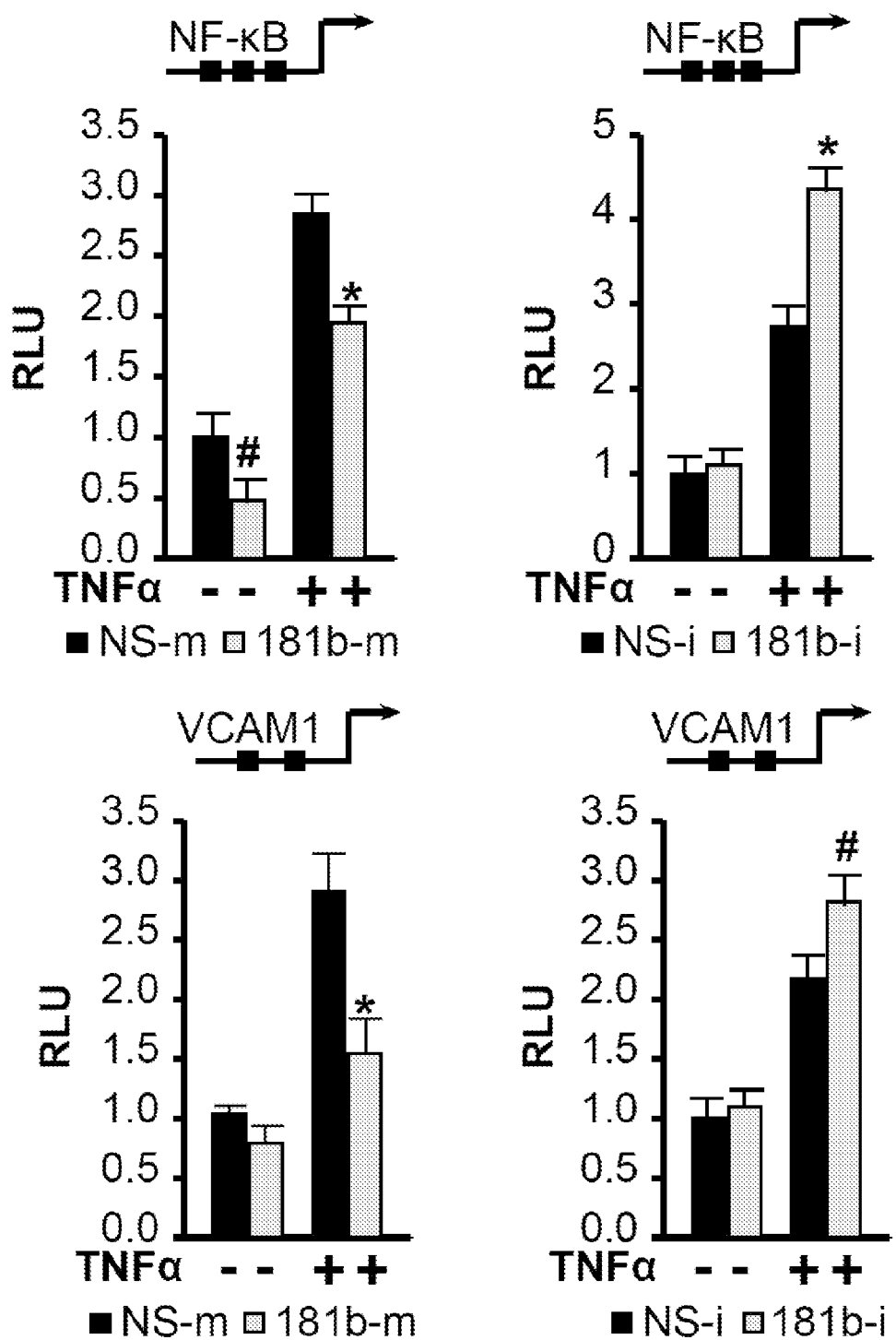
FIGS. 5A-C is five bar graphs and two Western blots showing that miR-181b inhibits activation of NF-κB signaling pathway.
Figure 5B:
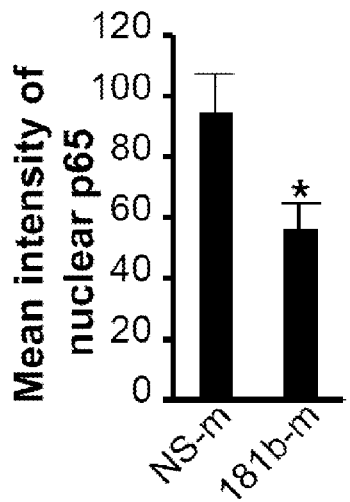
Figure 5C:
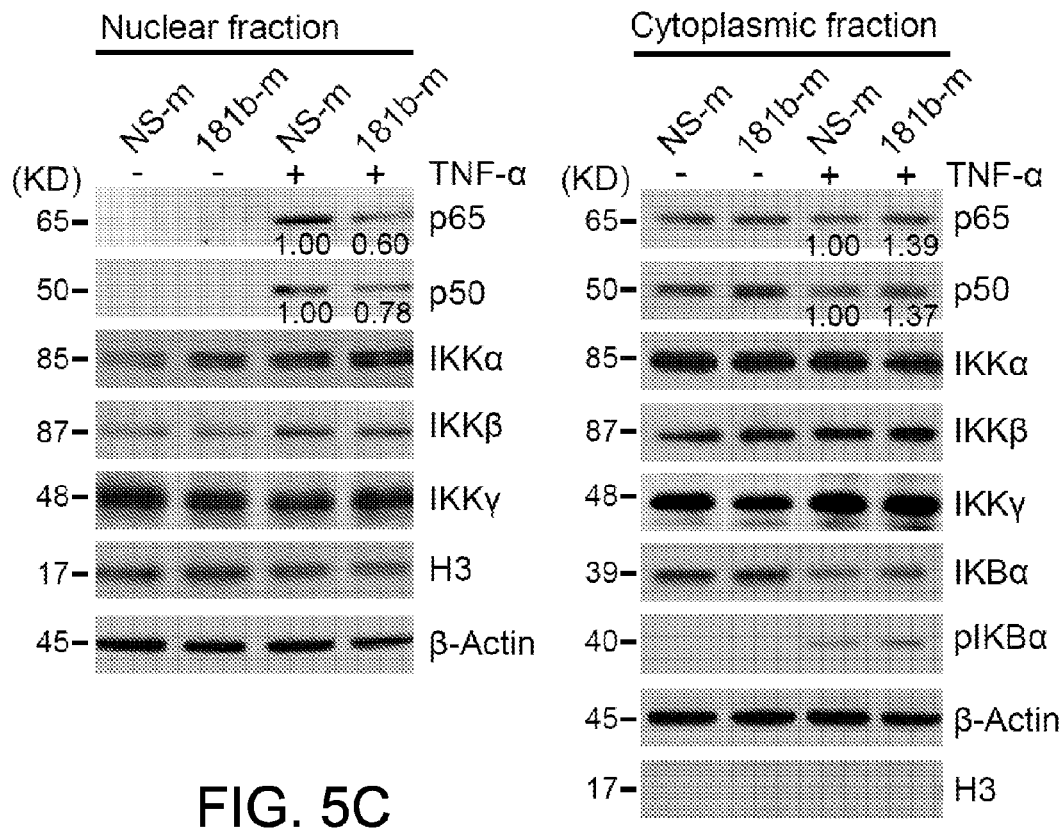

In response to pro-inflammatory stimuli, both the NF-κB and mitogen-activated protein (MAP) kinase pathway are involved in the inflammatory responses in endothelial cells (Hoefen et al., *Vascul. Pharmacol.* 38:271-273, 2002; Kempe et al., *Nucleic Acids Res.* 33:5308-5319, 2005). To examine whether miR-181b affects NF-κB activation, experiments were performed to test whether miR-181b has any effect on the NF-κB concatemer and VCAM-1 promoter-reporter. As shown in FIG. 3A, treatment of HUVECs with TNF-α induced the activity of both the NF-κB concatemer and the VCAM-1 promoter-reporter, and co-transfection of miR-181b significantly attenuated this induction. In contrast, inhibition of miR-181b potentiated TNF-α-induced activity (FIG. 5A). The effect of miR-181b on NF-κB nuclear accumulation was then determined by immunostaining for p65. A nearly 40% reduction in p65 nuclear staining was observed in HUVECs transfected with miR-181b, as compared to cells transfected with a miRNA negative control (FIG. 5B). After its release from the IκB complex, translocation of NF-κB from the cytoplasm to the nucleus is an essential step for the activation of NF-κB target genes (Oeckinghaus et al., *Cold Spring Harbor Perspect. Biol.* 1:a000034, 2009; Vallabhapurapu et al., *Annu. Rev. Immunol.* 27:693-733, 2009), an effect that can be revealed by detection of the p50 and p65 protein levels in cytoplasmic and nuclear fractions. As shown in FIG. 5C, HUVECs over-expressing miR-181b exhibited reduced p65 and p50 expression in the nuclear fraction, whereas the cytoplasmic fraction had increased p65 and p50 expression. Importantly, no significant differences between miR-181b and the miRNA negative control on the expression of upstream components of the NF-κB pathway was observed, including phosphorylated IκBα: an effect suggesting it is unlikely that miR-181b affects cell surface receptors or activation of the IKK complex. Since several MAP kinases have been implicated in TNF-α-induced expression of adhesion molecules, experiments were performed to test whether miR-181b had any effect on the activation of three MAP kinases (extracellular signal-regulated kinase (ERK), p38, and Jun-amino-terminal kinase (JNK)) in response to TNF-α. As shown in FIG. 6, the phosphorylation of ERK, p38, and JNK was robustly induced and peaked at 15 min after TNF-α treatment. However, miR-181b over-expression had no effect on their phosphorylation at 5, 15, and 30 min after TNF-α treatment. These data suggest that the inhibitory role of miR- 181b on TNF-α-induced gene expression is primarily due to its effects on the NF-κB signaling pathway by repressing NF-κB nuclear translocation.

MiR-181b Directly Targets Expression of Importin-α3, a Protein Critical for NF-κB Nuclear Translocation.

Previous studies have shown that NF-κBs are transported into the nucleus via a subset of importin-α molecules (Fagerlund et al., *J. Biol. Chem.* 280:15942-15951, 2005; Fagerlund et al., *Cell Signal.* 20:1442-1451, 2008). There are six importin-α paralogs in humans (importin-α1, -α3, -α4, -α5, -α6, and -α7) that are characterized by distinct affinities to their substrates (Kohler et al., *Mol. Cell. Biol.* 19:7782-7791, 1999). In miR-181b over-expressing cells, importin-α3 expression, but not that of importin-α1 or importin-α5, was reduced by 46% in the presence of TNF-α (FIG. 7A). Over-expression of miR-181b inhibited the activity of a luciferase reporter construct containing importin-α3 3'-UTR in a dose dependent manner (FIG. 7B). In contrast, the activity of luciferase constructs containing the 3'-UTR of importin-α1, -α4, or -α5 was not inhibited by over-expressed miR-181b (FIG. 7C).

Figure 8B:
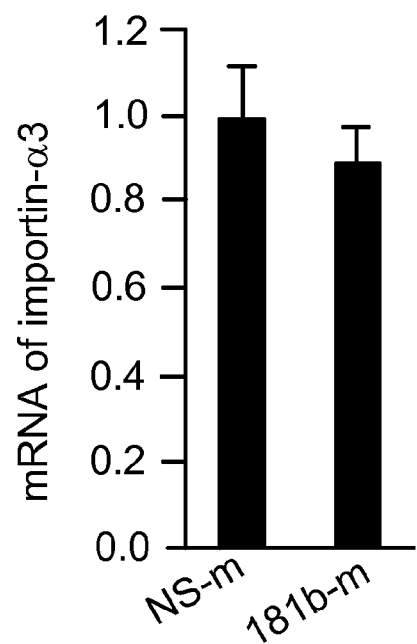

The rna22 miRNA target detection and predication algorithm allows for seed mismatches between mature miRNA and targeting mRNA sequence (Miranda et al., 2006), and has been successfully used to identify direct targets that were not predicted by other algorithms (Lal et al., *Mol. Cell* 35:610-625, 2009). To identify additional miR-181b binding sites that may exist in the 3'-UTR of importin-α3, the rna22 prediction algorithm was applied. The results identified eight potential miR-181b binding sites in the region of interest (FIG. 8A). Over-expression of miR-181b decreased luciferase activity by 31% and 20%, respectively, for luciferase-reporter constructs containing binding site 1 and site 2, but not for any of the other potential binding sites (FIG. 7D). Site-directed mutations of binding site 1 and site 2 rescued the miR-181b-mediated inhibitory effects on both of these constructs (FIG. 7D). Interestingly, the mRNA level of importin-α3 was not altered by miR-181b over-expression (FIG. 8B): an effect indicating that the reduction of importin-α3 at protein level is likely due to translation inhibition and not mRNA decay.

To further verify that miR-181b directly targets importin-α3, Argonaute2 (AGO2) microribonucleoprotein immunoprecipitation (miRNP-IP) studies were performed to assess whether importin-α3 mRNA is enriched in the RNA-induced silencing complex following miR-181b over-expression. An approximately 4-fold enrichment of importin-α3 mRNA was observed after AGO2 IP in the presence of miR-181b, as compared to that with the miRNA negative control (FIG. 7E). In contrast, AGO2 IP did not enrich the mRNA for Smad1, a gene that was not predicted to be a miR-181b target (FIG. 7E). Moreover, expression of importin-α3 lacking its 3'-UTR was able to rescue the inhibitory effect of miR-181b on NF-κB activation (FIG. 7F). Collectively, these data suggest that miR-181b inhibits the NF-κB signaling pathway by directly targeting importin-α3 expression.

MiR-181b Over-Expression Inhibited an Enriched Set of NF-κB Regulated Genes in Endothelial Cells.

Figure 9A:
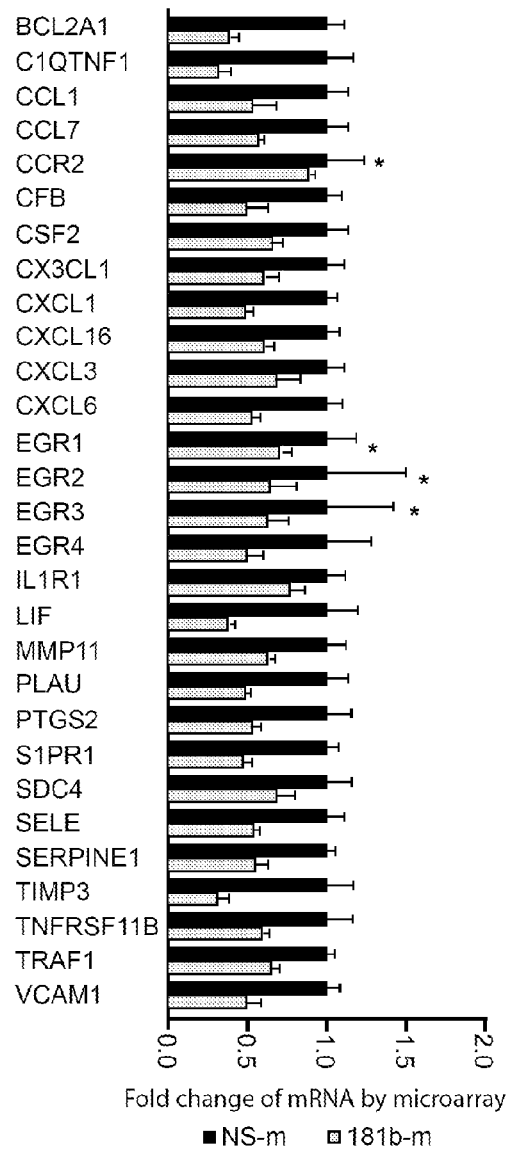
Figure 9B:
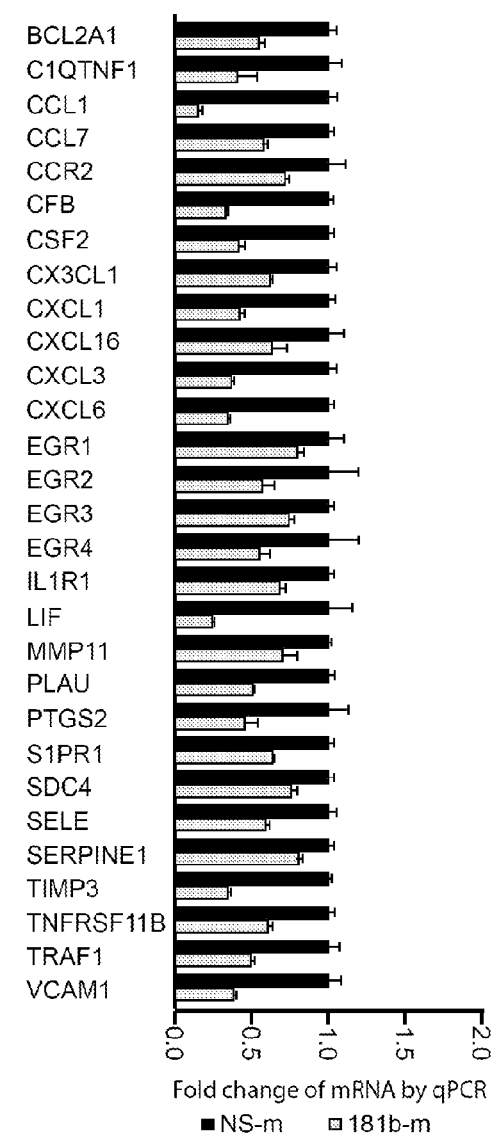
Figure 9C:
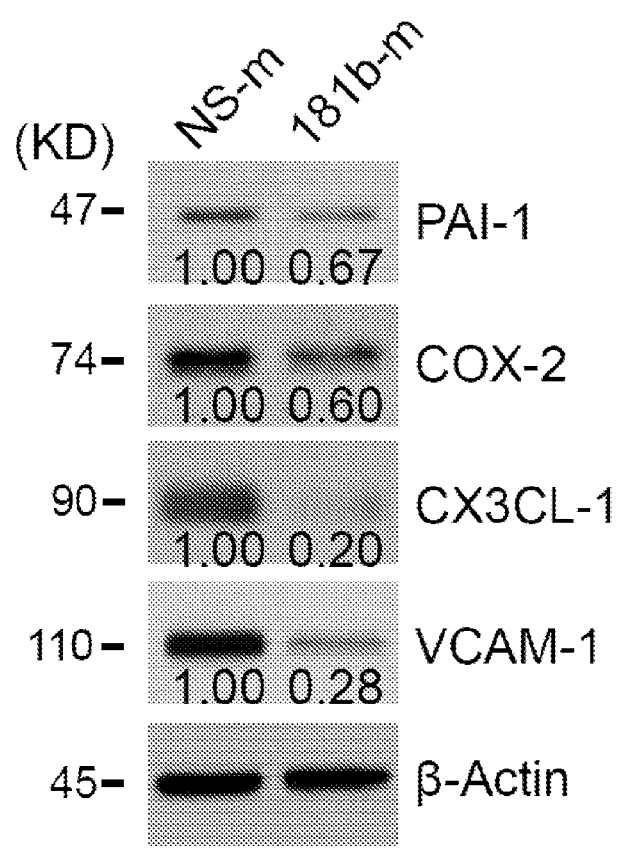

To systemically identify targets and biological processes regulated by miR-181b, the gene expression profiles of HUVECs transfected with miRNA negative control or miR-181b were comparatively analyzed using Agilent whole human genome microarrays. Transfected HUVECs were treated with TNF-α for 4 h and total RNA was isolated and processed for gene chip analysis. Out of the ~44,000 transcripts screened, 841 genes were down-regulated and 928 genes were up-regulated by at least 1.5-fold in miR-181b over-expression cells, as compared with control cells. Over 200 of those genes are known to be NF-κB-regulated. Moreover, 29 of these genes are associated with inflammation, and were all inhibited by over-expression of miR-181b. These reduced gene expression changes were verified by qPCR analysis (FIGS. 9A and 9B). PAI-1, COX-2, CX3CL-1, and VCAM-1 were chosen for further analysis by Western blot to verify concordant directional change in protein levels (FIG. 9C).

Among the 29 NF-κB regulated genes inhibited by miR-181b, some represent potential direct targets of miR-181b; for example, TIMP3 has been predicted as a direct target by TargetScan5.1 (Lewis et al., *Cell* 120:15-20, 2005) and by PicTar (Krek et al., *Nature Genet.* 37:495-500, 2005) algorithms, and EGR3 has been predicted by PicTar (Krek et al., 2005). Thus, the possibility that the observed reduction of EGR3 and TIMP3 may be a consequence of miR-181b's inhibitory effect on NF-κB activation and/or a direct effect of miR-181b on the 3'UTRs of these genes cannot be ruled out. To identify highly-regulated biological processes in miR-181b over-expressing cells, gene set enrichment analysis (GSEA), a computational method that determines if a defined set of genes shows significant differences between two biological states (Subramanian et al., *Proc. Natl. Acad. Sci. U.S.A.* 102:15545-15550, 2005), was performed. Six enriched biological processes were significantly represented by the reduced genes in miR-181b over-expressing cells: response to cytokine stimulus; positive regulation of cell migration; regulation of inflammatory response; inflammatory response; chemotaxis; and IκB kinase/NF-κB cascade (FIG. 9D). An abundance of targets that interconnected with the NF-κB signaling pathway were also observed using the Ingenuity web-based pathway analysis program. Taken together, these data suggest that miR-181b selectively suppressed an enriched set of NF-κB regulated genes and components of inflammatory signaling pathways in response to TNF-α in endothelial cells.

MiR-181b Inhibits LPS-Induced Endothelial Cell Activation, Leukocyte Accumulation, and Lung Airway Inflammation.

Figure 10A:
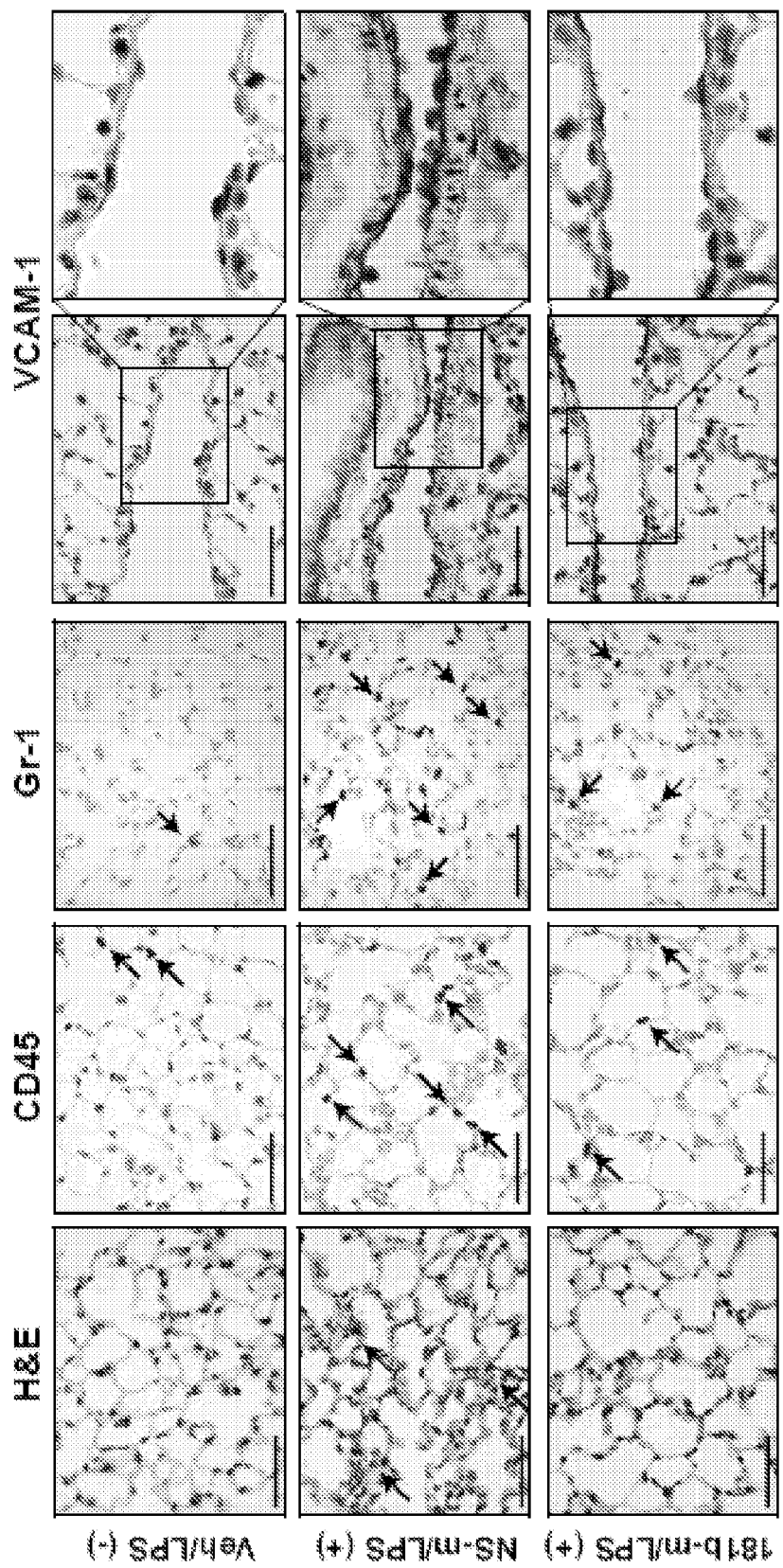
FIGS. 10A-F is a set of fifteen photomicrographs and five bar graphs that show that miR-181b reduces endothelial cell activation and leukocyte accumulation in LPS-induced lung inflammation.
Figure 10B:
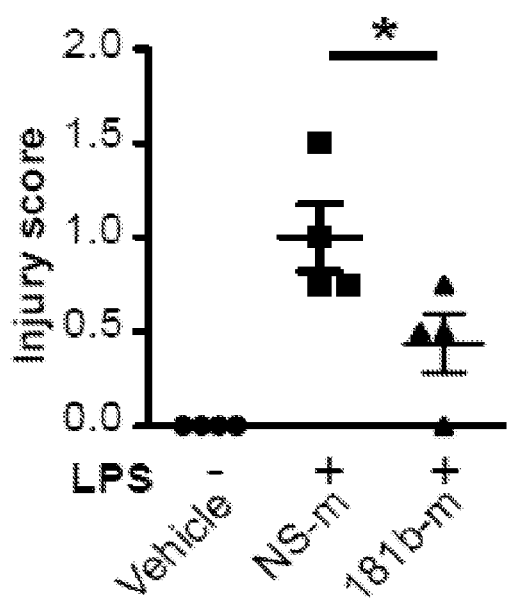
Figure 10C:
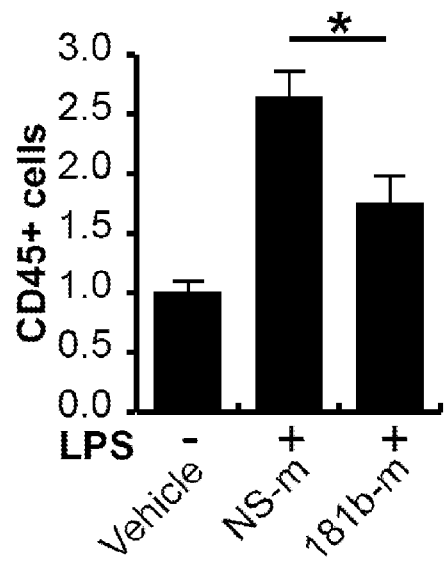
Figure 10D:
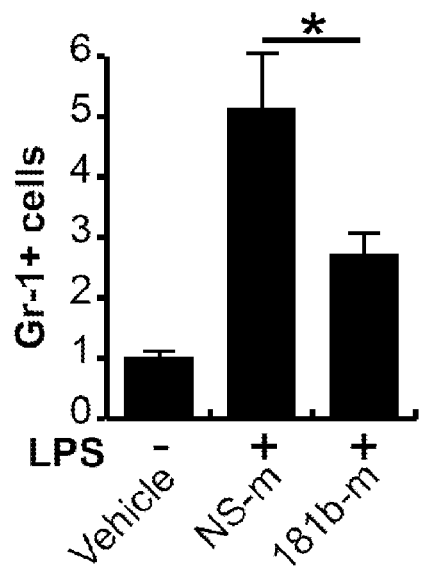
Figure 10E:
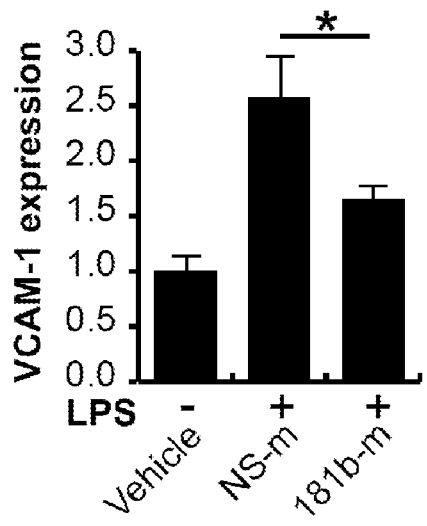
Figure 11A:
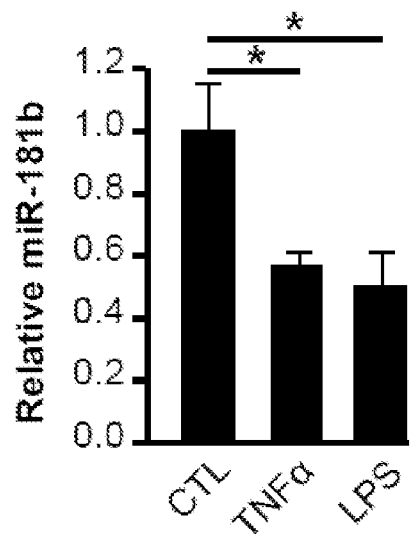
FIGS. 11A-D is a set of three photomicrographs and three bar graphs that show that miR-181b reduces leukocyte adhesion to the vascular endothelium in LPS-induced lung inflammation.
Figure 11B:
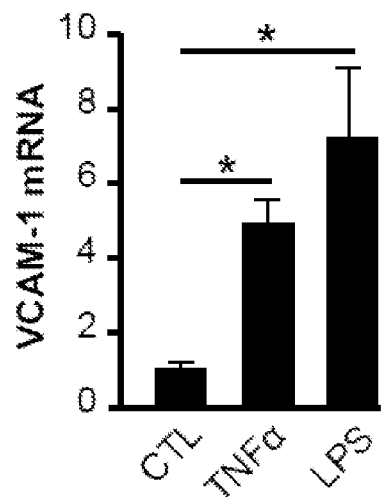
Figure 11C:
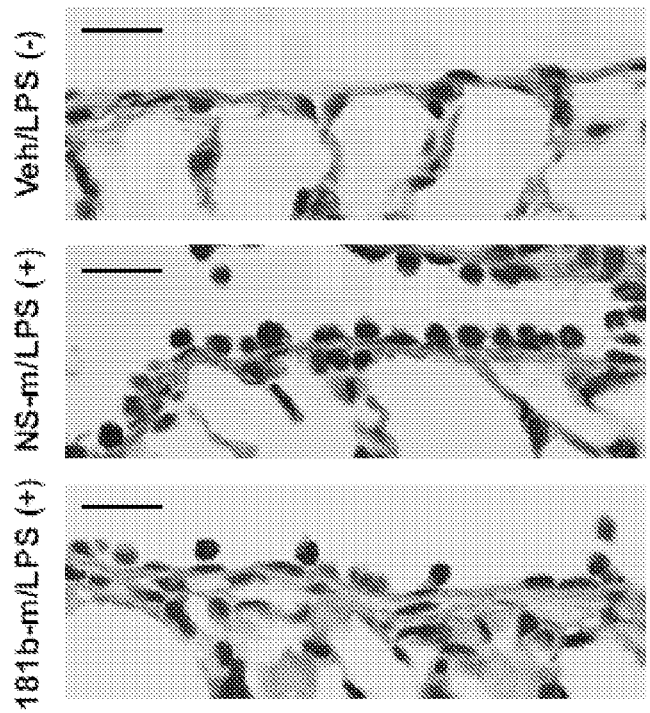
Figure 11D:
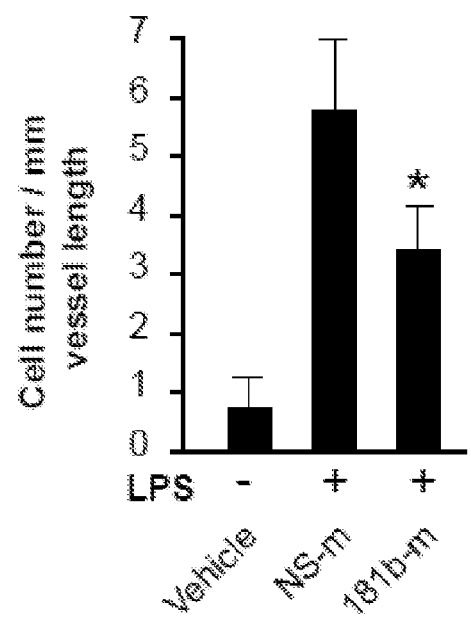

Sepsis is a severe medical condition with increasing incidence over the past few decades. Patients with sepsis are also at risk for other life-threatening complications, such as multisystem organ failure. The endotoxin LPS is a component of the outer membrane of Gram-negative bacteria, which plays a significant role in the pathogenesis of about 25%-30% sepsis (Annane et al., *Lancet* 365:63-78, 2005). LPS induces the release of critical pro-inflammatory cytokines including TNF-α, and elicits a systemic inflammatory response syndrome. During sepsis, activation of the vascular endothelium plays a critical role in the recruitment of neutrophils and monocytes/macrophages, and subsequent exacerbation of the inflammatory response (Aird, *Blood* 101:3765-3777, 2003; Woodman et al., *Am. J. Physiol. Heart Circ. Physiol.* 279: H1338-1345, 2000). To test if miR-181b contributes to this process, experiments were performed to determine whether in vivo over-expression of miR181b could reduce leukocyte recruitment and endothelial cell activation in a systemic LPS-induced mouse model of vascular inflammation. In vivo intravenous administration of miR-181b mimics reduced the induction of VCAM-1 expression in response to LPS by 60% (FIG. 10A, 10E). Analysis of lung sections taken from those mice injected with miR-181b revealed a significant reduction of CD45 (common leukocyte antigen)- and Gr-1 (predominantly neutrophil)-positive leukocytes (by 54% and 58%, respectively) in response to LPS treatment (FIGS. 10A, 10C, and 10D). Importantly, the number of Gr-1-positive leukocytes adherent to the pulmonary vascular endothelium was reduced 47% by miR-181b overexpression (FIGS. 11C and 11D). Reduced interstitial edema in the lungs of mice in which miR-181b was over-expressed was also observed (FIG. 10A). Lung injury scores were calculated, and the lungs from mice injected with miR-181b showed less damage (FIG. 10B).

Figure 10F:
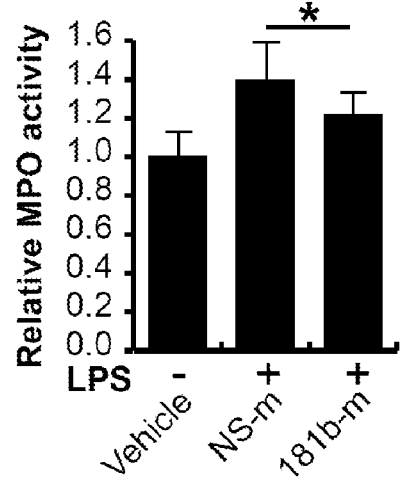

Myleoperoxidase activity, reflecting the presence of peroxidase enzyme expressed most abundantly in neutrophils, was also reduced by miR-181b over-expression (FIG. 10F). Taken together, these results demonstrate a critical role for miR-181b in endotoxin-induced endothelial activation and leukocyte accumulation, and suggest that over-expression of miR-181b could represent a new class of therapeutic avenues for limiting endotoxin-induced vascular inflammation.

To test if miR-181b contributes to this process, experiments were performed to determine whether the level of endothelium miR-181b could be affected in response to LPS, and whether in vivo over-expression of miR181b could reduce leukocyte recruitment and EC activation in a systemic LPS-induced mouse model of vascular inflammation. Four hours after LPS, the level of miR-181b was reduced 50% in freshly isolated aortic intima, while TNF-α treatment caused 47% reduction (FIG. 11A). The mRNA of VCAM-1 was induced about 5.0-fold and 7.2-fold by TNF-α and LPS in freshly isolated aortic intima respectively (FIG. 11B).

Sustained endothelial cell activation adversely contributes to the pathogenesis of both acute and chronic inflammatory disease states. As demonstrated herein, miR-181b is dynamically regulated in response to pro-inflammatory stimuli and functions to suppress the expression of an enriched set of NF-κB target genes associated with inflammatory disease states, such as adhesion molecules (e.g., VCAM-1 and E-selectin), chemokines, and chemokine receptors (e.g., CCL1, CCL7, CX3CL1, CXCL1, and CCR2), and other key inflammatory mediators (e.g., COX-2, PAI-1, EGR, and TRAF1). Furthermore, the data show that miR-181b directly targets importin-α3, an effect that inhibits nuclear accumulation of p50 and p65. Finally, administration of miR-181b mimics also reduced expression of adhesion molecules, leukocyte accumulation, and vascular inflammation in vivo. As such, these studies identify miR-181b as a regulator of endothelial cell activation in vitro and in vivo.

miR-181b is identified herein as a cytokine-responsive miRNA that regulates the expression of key NF-κB-regulated genes involved in the endothelial response to inflammation in vitro and in vivo. These findings also revealed a novel and unexpected mechanistic role for this miRNA in targeting downstream NF-κB signaling by directly targeting importin-α3. These studies support the use of miR-181b as an agent that can control critical aspects of endothelial cell homeostasis under physiologic or pathologic conditions.

Materials and Methods
Reagents and Antibodies

Cy3 dye-labeled Pre-miR negative control #1(AM17120), Pre-miR miRNA precursor molecules-negative control #1 (AM17110), Pre-miR miRNA precursor molecules-miR-181b (PM12442), Anti-miR miRNA inhibitors-negative control #1(AM17010), and miR-181b inhibitor (AM12442) were from Ambion. For in vivo studies, oligomers with the same sequence were synthesized on a larger scale. Anti-p65 (sc-8008), anti-p50 (sc-8414), anti-IKKα (sc-7182), anti-IKKγ (sc-8330), goat anti-mouse VCAM-1 (sc-1504), mouse anti-human VCAM-1 (sc-13160), goat anti-mouse IgG-HRP (sc-2005), goat anti-rabbit IgG-HRP (sc-2004), goat anti-chicken IgY-HRP (sc-2901), donkey anti-goat IgG-HRP (sc-2020) were from Santa Cruz Biotechnology. Cy5-conjugated goat anti-mouse IgG was from Jackson ImmunoResearch. Anti-phospho-p38 MAPK (Thr180/Tyr182) (4511), anti-phospho-SAPK/JNK (Thr183/Tyr185) (4668), anti-phospho-p44/42 MAPK (Thr202/Tyr204) (4370), anti-p38 MAPK (9212), anti-SAPK/JNK (9258), anti-IκBα (4814), anti-β-actin (4970), anti-Histone H3 (9715), anti-IKKβ (2370), anti-p44/42 (9107), anti-phospho-IκBα (2859), anti-Cox-2 (4842) were from Cell Signaling. Anti-importin-α1 (D168-3), anti-importin-α3 (D169-3), anti-importin-α5/7 (D170-3) were from MBL, Medical & Biological Laboratories. Monoclonal anti-human E-selectin (CD62E) (S9555) was from Sigma. Anti-human E-selectin monoclonal antibody (BBA16), anti-rat IgG-HRP (HAF005), anti-human ICAM-1/CD54 Clone BBIG-I1 (BBA3), anti-human PAI-1 (MAB1786) were from R&D Systems. Anti-CX3CL-1 (14-7986) was from eBioscience. Anti-Ly-6G and Ly-6C/Gr-1 (550291), and anti-CD45 (550539) were from BD Pharmingen.

Cell Culture and Transfection

THP-1 cells were from ATCC, and cultured in ATCC-formulated RPMI-1640 medium (30-2001) supplemented with 10% fetal bovine serum and 0.05 mM 2-mercaptoethanol. HUVECs were obtained from Lonza (cc-2159) and cultured in endothelial cell growth medium EGM-2 (cc-3162). Cells passaged less than five times were used for all experiments. Lipofectamine 2000 transfection reagent from Invitrogen was used for transfection, following the manufacturer's instructions. Cells were allowed to grow for 36 h before treatment with 10 ng/ml recombinant human TNF-α from R & D Systems (210-TA/CF) for various times, according to the experiment: Western blot, 8 h; real-time qPCR, 1, 3, 4, or 16 h; or ELISA, 16 h.

Constructs

The human miR-181b gene, including 96 bp upstream and 241 bp downstream flanking regions of its stem loop sequence, was amplified by PCR from human genomic DNA (Promega) using Platinum PCR SuperMix High Fidelity Taq-based enzyme mix (Invitrogen). The resultant fragment was subcloned into the pcDNA3.1(+) vector to generate the pcDNA3.1(+)-miR-181b plasmid. Primers 5'-CCCAAGCTTTGATTGTAC CCTATGGCT-3' (forward; SEQ ID NO: 4) and 5'-CGGGGTACCTGTACGTTTGATGG ACAA-3' (reverse; SEQ ID NO: 5) were used to amplify human miR-181b coding sequence.

The 3'-UTR of genes for importin-α1, importin-α3, importin-α4, importin-α5, and VCAM-1 were amplified from human genomic DNA and cloned into the pMIR-REPORT Luciferase vector, between Sad and MluI restriction sites (importins) or MluI and HindIII restriction sites (VCAM-1). Putative miR-181b binding sites in the importin-α3 gene 3'-UTR were predicted by the rna22 algorithm. Individual wild-type or mutant binding site sequence was generated by annealing the forward and reverse oligonucleotides containing SpeI and HindIII sticky ends, followed by T4 Polynucleotide Kinase (New England Biolabs) phosphorylation. The double-stranded oligonucleotides were ligated into the pMIR-REPORT Luciferase vector, between SpeI and HindIII restriction sites, using T4 DNA ligase (New England Biolabs). A construct containing the open reading frame cDNA of importin-α3 was purchased from OriGene. The primers used are listed in Table 1 below.

TABLE 1

| | Primers used for Studies | |
|---|---|---|
| | Name | Sequence (5' -> 3') |
| For Real Time qPCR | mouse VCAM-1 F: | GTTCCAGCGAGGGTCTACC (SEQ ID NO: 6) |
| | mouse VCAM-1 R: | AACTCTTGGCAAACATTAGGTGT (SEQ ID NO: 7) |
| | mouse E-selectin F: | ATGCCTCGCGCTTTCTCTC (SEQ ID NO: 8) |
| | mouse E-selectin R: | GTAGTCCCGCTGACAGTATGC (SEQ ID NO: 9) |
| | mouse ICAM-1 F: | GTGATGCTCAGGTATCCATCCA (SEQ ID NO: 10) |
| | mouse ICAM-1 R: | CACAGTTCTCAAAGCACAGCG (SEQ ID NO: 11) |
| | mouse actin F: | GAAATCGTGCGTGACATCAAAG (SEQ ID NO: 12) |
| | mouse actin R: | TGTAGTTTCATGGATGCCACAG (SEQ ID NO: 13) |
| | human PAI-1 F: | CATCCCCCATCCTACGTGG (SEQ ID NO: 14) |
| | human PAI-1 R: | CCCCATAGGGTGAGAAAACCA (SEQ ID NO: 15) |
| | human VCAM-1 F: | GCTGCTCAGATTGGAGACTCA (SEQ ID NO: 16) |
| | human VCAM-1 R: | CGCTCAGAGGGCTGTCTATC (SEQ ID NO: 17) |
| | human E-selectin F: | AATCCAGCCAATGGGTTCG (SEQ ID NO: 18) |
| | human E-selectin R: | GCTCCCATTAGTTCAAATCCTTCT (SEQ ID NO: 19) |
| | human ICAM-1 F: | TCTGTGTCCCCCTCAAAAGTC (SEQ ID NO: 20) |
| | human ICAM-1 R: | GGGGTCTCTATGCCCAACAA (SEQ ID NO: 21) |
| | human GAPDH F: | ATGGGGAAGGTGAAGGTCG (SEQ ID NO: 22) |
| | human GAPDH R: | GGGGTCATTGATGGCAACAATA (SEQ ID NO: 23) |
| | mouse importin-α3 F | CCAGTGATCGAAATCCACCAA (SEQ ID NO: 24) |
| | mouse importin-α3 R: | CGTTTGTTCAGACGTTCCAGAT (SEQ ID NO: 25) |
| | human importin-α3 F: | TCCAGTGATCGAAATCCACCA (SEQ ID NO: 26) |
| | human importin-α3 R: | CATTGGACTGAACTACTGCTTGA (SEQ ID NO: 27) |
| | human Smad1 F: | GATGCCAGGTAGGTTGGAATG (SEQ ID NO: 28) |
| | human Smad1 R: | CGTGACACTGTGATAACACTGT (SEQ ID NO: 29) |
| Oligonucleotides | Site1 forward: | CTAGTCTTGCTATGAAGCAGTGTGTGAAA (SEQ ID NO: 30) |
| | Site1 reverse: | AGCTTTTCACACACTGCTTCATAGCAAGA (SEQ ID NO: 31) |
| | Site2 forward: | CTAGTATGGACAATGTTGAATGAATGTCA (SEQ ID NO: 32) |
| | Site2 reverse: | AGCTTGACATTCATTCAACATTGTCCATA (SEQ ID NO: 33) |
| | Site3 forward: | CTAGTCTGTGTACGAGAGCGTGGTTGTGA (SEQ ID NO: 34) |
| | Site3 reverse: | AGCTTCACAACCACGCTCTCGTACACAGA (SEQ ID NO: 35) |
| | Site4 forward: | CTAGTTGGTTTACTCTGCAGCCTGTGTTA (SEQ ID NO: 36) |
| | Site4 reverse: | AGCTTAACACAGGCTGCAGAGTAAACCAA (SEQ ID NO: 37) |
| | Site5 forward: | CTAGTTGCATTTGCACCAGATGAATGTTA (SEQ ID NO: 38) |
| | Site5 reverse: | AGCTTAACATTCATCTGGTGCAAATGCAA (SEQ ID NO: 39) |
| | Site6 forward: | CTAGTTTTCCCTCAAAATAGACTGTGTTA (SEQ ID NO: 40) |
| | Site6 reverse: | AGCTTAACACAGTCTATTTTGAGGGAAAA (SEQ ID NO: 41) |
| | Site7 forward: | CTAGTATACCGTGCTGTGTTTAAATGTTA (SEQ ID NO: 42) |
| | Site7 reverse: | AGCTTAACATTTAAACACAGCACGGTATA (SEQ ID NO: 43) |

TABLE 1-continued

Primers used for Studies

| | Name | Sequence (5' -> 3') |
|---|---|---|
| | Site8 forward: | CTAGTCTTCCCCTTTGAGCACAAGTGTTA (SEQ ID NO: 44) |
| | Site8 reverse: | AGCTTAACACTTGTGCTCAAAGGGGAAGA (SEQ ID NO: 45) |
| | Site1mut forward: | CTAGTCTTGCTATGATAAAGCTTCTGAAA (SEQ ID NO: 46) |
| | Site1mut reverse: | AGCTTTTCAGAAGCTTTATCATAGCAAGA (SEQ ID NO: 47) |
| | Site2mut forward: | CTAGTAGGCTGAATCTTGCCAACATCACA (SEQ ID NO: 48) |
| | Site2mut reverse: | AGCTTGTGATGTTGGCAAGATTCAGCCTA (SEQ ID NO: 49) |
| For cloning 3'-UTR | Importin-α1 forward: | ACGAGCTCATCATGTAGCTGAGACATAAATTTG (SEQ ID NO: 50) |
| | Importin-α1 reverse: | ATAACGCGTAGAAAAGGGTGGACTTGAATGT (SEQ ID NO: 51) |
| | Importin-α3 forward: | ACGAGCTCAAAGATGTTGTGGAAGTTAGG (SEQ ID NO: 52) |
| | Importin-α3 reverse: | ATAACGCGTCACAGCACGGTATTCTACCAC (SEQ ID NO: 53) |
| | Importin-α4 forward: | ACGAGCTCATTCAGTTGAGTGCAGCATC (SEQ ID NO: 54) |
| | Importin-α4 reverse: | ATAACGCGTCCTCTACACAGATCCCTGTC (SEQ ID NO: 55) |
| | Importin-α5 forward: | ACGAGCTCAGCAATACTCTGCTTTCACG (SEQ ID NO: 56) |
| | Importin-α5 reverse: | ATAACGCGTGATTAGAATCGAGCTGCACC (SEQ ID NO: 57) |
| | VCAM-1 forward: | TCGACGCGTGCAAATCCTTGATACTGC (SEQ ID NO: 58) |
| | VCAM-1 reverse: | CCCAAGCTTATTGGGAAAGTTGCACAG (SEQ ID NO: 59) |

Luciferase Reporter Assays

HUVECs were plated (50,000/well) in triplicate on a 12-well plate. After growing to 70-80% confluency, cells were transfected with 200 ng of the indicated reporter constructs and 100 ng β-galactosidase (gal) expression plasmids. MiR-181b mimics or inhibitors were co-transfected at 10 or 50 nM final concentration where indicated; after 36 h incubation, cells were treated with 10 ng/ml TNF-α for 8 h. In some experiments, pcDNA3.1-miR-181b or empty vector were co-transfected with 200 ng reporter constructs and 100 ng β-gal expression plasmids. For rescue studies, NF-κB concatemer luciferase reporter was co-transfected with pcDNA3.1-miR-181b or empty vector in the presence or absence of open reading frame cDNA of importin-α3 into 293T cells. Transfected cells were collected in 200 μL Reporter Lysis Buffer (Promega). The activity of luciferase and β-gal were measured. Each reading of luciferase activity was normalized to the β-gal activity read for the same lysate.

Enzyme-Linked Immunosorbent Assays (ELISAs)

HUVECs were transfected with control miRNAs, miR-181b at the final concentration of 10 nM, control miRNA inhibitors, or miR-181b inhibitors at the final concentration of 50 nM, respectively. After 36 h, cells were exposed to 10 ng/ml TNF-α for 16 h. Then, the supernatants were collected for ELISA analysis by means of SearchLight Multiplex Immunoassay Kit (Aushon BioSystems, Inc).

Cell Adhesion Assays

HUVECs grown in 12-well plates were transfected with miRNA mimics or inhibitors. Twenty-four hours later, transfected cells were replated onto 96-well fluorescence plates (BD, cat#353948) for overnight growth. The following day 10 ng/ml TNF-α was added for 5 h. THP-1 cells (ATCC) were washed with serum-free RPMI-1640 medium and suspended at $5 \times 10^6$ cells/mL in medium with 5 μM of Calcein AM (Invitrogen, cat# C3100MP). Cells were kept in an incubator containing 5% $CO_2$ at 37° C. for 30 min. The labeling reaction was stopped by the addition of the cell growth medium, and cells were washed with growth medium twice then re-suspended in growth medium at $5 \times 10^5$ cells/ml. After 5 h TNF-α treatment, HUVECs were washed once with THP-1 cell growth medium. Then 200 μL Calcein AM-loaded THP-1 cells were added to each well. After 1-h incubation, non-adherent cells were removed carefully. Adherent cells were gently washed with pre-warmed RPMI-1640 medium four times. Fluorescence was measured by using a fluorescence plate reader at 485 nm excitation. The number of THP-1 cells per view was quantified from randomly acquired images.

Real-Time Quantitative PCR

HUVECs were suspended in Trizol reagent(Invitrogen), and total RNA was isolated according to the manufacturer's instructions. Reverse transcriptions were performed by using miScript Reverse Transcription Kit from Qiagen (218061). Either QuantiTect SYBR Green RT-PCR Kit (204243) or miScript SYBR Green PCR Kit (218073) from Qiagen was used for quantitative real-time qPCR analysis with the Mx3000P Real-time PCR system (Stratagene), following the manufacturer's instructions. Gene- and species-specific primers were used to detect human or mouse VCAM-1, E-selectin, PAI-1, and ICAM-1. To amplify mature miRNA sequences, hsa-miR-181a (PN4373117), hsa-miR-181b (PN4373116), hsa-miR-181c (PN4373115), hsa-miR-181d (PN4373180), RNU6B (PN4373381), TaqMan MicroRNA Reverse Transcription Kit (PN4366596), TaqMan® Universal PCR Master Mix, No AmpErase UNG (PN4324018), or miScript primer assays for Hs_RN5S1_1 (MS00007574) and Hs_miR-181b_1 (MS00006699) from Qiagen were used.

Intimal RNA Isolation from Aorta Tissue

Isolation of intimal RNA from aorta was modified from a previous study (Nam et al., *Am. J. Physiol. Heart Circ. Physiol.* 297:H1535-1543, 2009). Briefly, aorta between the heart and diaphragm was exposed, and the peri-adventitial tissues were removed carefully. The cleaned aorta was cut out and transferred to a 35-mm dish containing ice-cold Hank's Buffered Salt Solution (HBSS). The tip of an insulin syringe needle was carefully inserted into one end of the aorta to facilitate a quick flush of 150 µL QIAzol lysis buffer through it and collection of the intima eluate into a 1.5-ml tube. The aorta leftover (media+adventitia) was washed once with HBSS and snap-frozen in liquid nitrogen, for storage until total RNA extraction by TRIzol.

Immunostaining

HUVECs grown on coverslips were fixed with 4% paraformaldehyde and permeabilized with 0.5% Triton X-100 (Sigma). After blocking with normal goat serum, cells were incubated with antibody against p65 followed by Cy5-conjugated goat anti-mouse IgG and DAPI (Invitrogen). Images were acquired with an Olympus Fluoview FV1000 confocal microscope equipped with a Multi-Ar laser, HeNe G laser, HeNe R laser, and a LD405/440 laser diode. The UPLSAPO 20×NA: 0.75 objective lens was used. The following parameters were set: Zoom×2, 1024×1024[pixel] image size, C.A. 150 µm. The intensity of p65 nuclear staining was quantified by using Bitplane Imaris 6.4.2 software.

MiRNP Immunoprecipitation

MiRNP-IP was performed as previously described (Fasanaro et al., *J. Biol. Chem.* 284:35134-35143, 2009; Huang et al., *Mol. Cell.* 35:856-867, 2009). Myc-tagged Ago-2 (from Cold Spring Harbor, N.Y.) was co-transfected with either miR-181b or miRNA negative control in HUVECs. Cells were washed in ice cold PBS, released by scraping, and lysed in buffer (10 mM Tris-HCl pH 7.5, 10 mM NaCl, 2 mM EDTA, 0.5% Triton X-100, 100 units/mL of RNasin Plus (Promega) supplemented with 1× protease inhibitor (Roche)). The lysed cell solution was adjusted to a final NaCl concentration of 150 mM prior to centrifugation. One-twentieth of the supernatant volume was collected in TRIzol for use as an extract control. The remaining portion of the supernatant was pre-cleared with Protein A/G UltraLink Resin (Pierce), to which 2 µg anti-c-myc antibody was added and the mixture allowed to incubate overnight at 4° C.; the following day Protein A/G UltraLink Resin was added. After 4 h of mechanical rotation at 4° C., the agarose beads were pelleted and washed four times in wash buffer (50 mM Tris-HCl pH 7.5, 150 mM NaCl, 0.05% Triton X-100). Finally, 1 mL of TRIzol was added into the beads and RNA was isolated. Total RNA was reverse transcribed into cDNA for real-time qPCR analysis.

Protein Extraction and Western Blot Analysis

Transfected HUVECs were treated with 10 ng/ml TNF-α for 1 h, then cytoplasmic and nuclear extracts were isolated by NE-PER nuclear and cytoplasmic extraction reagents (Thermo Fisher Scientific). Cultured cells were harvested and lysed in RIPA buffer (50 mM Tris-HCL pH 7.4, 150 mM NaCl, 1% NP-40, 0.5% sodium deoxycholate, 0.1% SDS) supplemented with complete protease inhibitor cocktail tablets (Roche). To extract protein, snap-frozen tissues were homogenized in RIPA buffer supplemented with protease inhibitor. Cell or tissue debris was removed by centrifugation at 12,000 rpm for 10 min. Lysates were separated by 8% or 10% SDS-PAGE gels, transferred to PVDF membranes (Bio-Rad), and incubated with the relevant antibodies as where indicated. Proteins were visualized by ECL Plus Western blotting detection reagents (RPN2132; GE Healthcare). Densitometry scanning of the blots with ImageJ software was used to calculate the abundance of protein.

Microarray Gene Chip Analysis and Bioinformatics

HUVECs were transfected with 10 nM miRNA negative control or miR-181b mimics for 36 h, and treated with 10 ng/ml TNF-α for 4 h. Cells were collected into TRIzol and sent for Two-Color, 4×44 K format, Human Whole Genome Microarray Service (Miltenyi Biotec Inc.). Differentially expressed genes were identified by using the fold-change lower threshold of 1.5. Gene set enrichment analysis (Subramanian et al., *Proc. Natl. Acad. Sci.* 102:15545-1550, 2005) was used to test whether a known biological pathway/process or molecular function was suppressed by over-expression of miR-181b. Gene sets used for enrichment analyses were downloaded directly from the Broad Institute website or the Gene Ontology website. Gene sets discovered with a false discovery rate (FDR) less than 25% were considered as significantly enriched. The primers used for real-time qPCR validation are listed in Table 2 below.

TABLE 2

Primers used for qPCR Validation

| Name | Sequence (5' -> 3') |
|---|---|
| BCL2A1-F | TACAGGCTGGCTCAGGACTAT (SEQ ID NO: 60) |
| BCL2A1-R | TTTTGTAGCACTCTGGACGTTT (SEQ ID NO: 61) |
| C1QTNF1-F | CAAGGGAAATATGGCAAAACAGG (SEQ ID NO: 62) |
| C1QTNF1-R | ATCACCGTCTGGTAGTAGTGG (SEQ ID NO: 63) |
| CCL1-F | TCATTTGCGGAGCAAGAGATT (SEQ ID NO: 64) |
| CCL1-R | CTGAACCCATCCAACTGTGTC (SEQ ID NO: 65) |
| CCL7-F | CCAATGCATCCACATGCTGC (SEQ ID NO: 66) |
| CCL7-R | GCTTCCCAGGGACACCGAC (SEQ ID NO: 67) |
| CCR2-F | GACCAGGAAAGAATGTGAAAGTGA (SEQ ID NO: 68) |
| CCR2-R | GCTCTGCCAATTGACTTTCCTT (SEQ ID NO: 69) |
| CFB-F | GCGGCCCCTTGATAGTTCAC (SEQ ID NO: 70) |
| CFB-R | CAGGGCAGCACTTGAAAGAG (SEQ ID NO: 71) |
| CSF2-F | GGGAGCATGTGAATGCCATC (SEQ ID NO: 72) |
| CSF2-R | GCAGTGTCTCTACTCAGGTTCAG (SEQ ID NO: 73) |
| CX3CL1-F | ACCACGGTGTGACGAAATG (SEQ ID NO: 74) |
| CX3CL1-R | CTCCAAGATGATTGCGCGTTT (SEQ ID NO: 75) |
| CXCL1-F | AGGGAATTCACCCCAAGAAC (SEQ ID NO: 76) |
| CXCL1-R | ACTATGGGGGATGCAGGATT (SEQ ID NO: 77) |
| CXCL16-F | CAGCGTCACTGGAAGTTGTTA (SEQ ID NO: 78) |
| CXCL16-R | CACCGATGGTAAGCTCTCAGG (SEQ ID NO: 79) |
| CXCL3-F | CCAAACCGAAGTCATAGCCAC (SEQ ID NO: 80) |
| CXCL3-R | TGCTCCCCTTGTTCAGTATCT (SEQ ID NO: 81) |
| CXCL6-F | AGAGCTGCGTTGCACTTGTT (SEQ ID NO: 82) |
| CXCL6-R | GCAGTTTACCAATCGTTTTGGGG (SEQ ID NO: 83) |
| EGR1-F | ACCTGACCGCAGAGTCTTTTC (SEQ ID NO: 84) |
| EGR1-R | GCCAGTATAGGTGATGGGGG (SEQ ID NO: 85) |
| EGR2-F | ATCCCAGTAACTCTCAGTGGTT (SEQ ID NO: 86) |
| EGR2-R | CTCCACCGGGTAGATGTTGT (SEQ ID NO: 87) |
| EGR3-F | GCGACCTCTACTCAGAGCC (SEQ ID NO: 88) |
| EGR3-R | ATGGGGAAGAGATTGCTGTCC (SEQ ID NO: 89) |
| EGR4-F | AGCGAGTTTTCCGAACCCG (SEQ ID NO: 90) |
| EGR4-R | GAGTCGGCTAAGTCCCCACT (SEQ ID NO: 91) |
| IL1R1-F | ACATTGTGCTTTGGTACAGGG (SEQ ID NO: 92) |
| IL1R1-R | CCCCAACAGTCTTTGGATACAG (SEQ ID NO: 93) |

TABLE 2-continued

Primers used for qPCR Validation

| Name | Sequence (5' -> 3') |
|---|---|
| LIF-F | GTACCGCATAGTCGTGTACCT (SEQ ID NO: 94) |
| LIF-R | CACAGCACGTTGCTAAGGAG (SEQ ID NO: 95) |
| MMP11-F | GAGGCCCTAAAGGTATGGAGC (SEQ ID NO: 96) |
| MMP11-R | CCCTTCTCGGTGAGTCTTGG (SEQ ID NO: 97) |
| PLAU-F | GTGAGCGACTCCAAAGGCA (SEQ ID NO: 98) |
| PLAU-R | GCAGTTGCACCAGTGAATGTT (SEQ ID NO: 99) |
| PTGS2-F | GTGCAACACTTGAGTGGCTAT (SEQ ID NO: 100) |
| PTGS2-R | AGCAATTTGCCTGGTGAATGAT (SEQ ID NO: 101) |
| S1PR1-F | CTTGCTGACCATTTGGAAAACC (SEQ ID NO: 102) |
| S1PR1-R | CTGTGTAGGCTACTCCTGCC (SEQ ID NO: 103) |
| SDC4-F | GCTCTTCGTAGGCGGAGTC (SEQ ID NO: 104) |
| SDC4-F | CCTCATCGTCTGGTAGGGCT (SEQ ID NO: 105) |
| SELE-F | AATCCAGCCAATGGGTTCG (SEQ ID NO: 106) |
| SELE-R | GCTCCCATTAGTTCAAATCCTTCT (SEQ ID NO: 107) |
| SERPINE1-F | CATCCCCCATCCTACGTGG (SEQ ID NO: 108) |
| SERPINE1-R | CCCCATAGGGTGAGAAAACCA (SEQ ID NO: 109) |
| TIMP3-F | CATGTGCAGTACATCCACACG (SEQ ID NO: 110) |
| TIMP3-R | ACATCTTGCCATCATAGACGC (SEQ ID NO: 111) |
| TNFRSF11B-F | AAGGGCGCTACCTTGAGATAG (SEQ ID NO: 112) |
| TNFRSF11B-R | GCAAACTGTATTTCGCTCTGGG (SEQ ID NO: 113) |
| TRAF1-F | CCGGCCCCTGATGAGAATG (SEQ ID NO: 114) |
| TRAF1-R | TTCCTGGGCTTATAGACTGGAG (SEQ ID NO: 115) |
| VCAM1-F | GCTGCTCAGATTGGAGACTCA (SEQ ID NO: 116) |
| VCAM1-R | CGCTCAGAGGGCTGTCTATC (SEQ ID NO: 117) |
| GAPDH-F | ATGGGAAGGTGAAGGTCG (SEQ ID NO: 118) |
| GAPDH-R | GGGGTCATTGATGGCAACAATA (SEQ ID NO: 119) |

In Vivo MiR-181b Over-Expression and Animal Experiments

Male C57BL/6 mice 8-10 weeks old were purchased from Charles River. An equal volume of Atelocollagen (Koken, Tokyo, Japan) and miRNAs (Ambion) were mixed to form complexes, according to the manufacturer's guideline. Each mouse (n=3-6 per group) was administered 200 μL mixtures containing 50 μg negative control or miR-181b mimics by tail vein injection. Recombinant mouse TNF-α (2 μg/mouse) from R & D Systems (410-MT/CF) was intraperitoneally (i.p.) injected on the following day. Four hours later, mice were sacrificed to harvest tissues and organs for analysis. Lungs were used for Western blot analysis, total RNA extraction, and immunohistochemistry. Aorta arches were snap-frozen for total RNA extraction, while the descending aorta was fixed with 4% paraformaldehyde and embedded in paraffin for immunohistochemistry. Hearts, spleens, and livers were used for total RNA isolation. Six-μm sections were prepared from paraffin-embedded lung and aorta; sections were then deparaffinized with xylene and rehydrated in water through a graded ethanol series, followed by antigen retrieval performed for 5 min in a pressure cooker using Tris-EDTA solution, pH 8.0. The sections were treated with TBST buffer and 3% $H_2O_2$, blocked with blocking reagent, incubated sequentially with goat anti-mouse VCAM-1, secondary antibody, and DAB chromagen, and counterstained with hematoxylin. Images were acquired by a digital system.

For murine endotoxemia model, mice were administered with vehicle, miRNA negative control, or miR-181b mimics by tail vein injection. On the following day, mice were i.p. injected with 40 mg/kg LPS (*Escherichia coli* serotype 026: B6 endotoxin; Sigma-Aldrich) or vehicle (saline). Lung tissues were processed for immunohistochemistry 4 h after LPS treatment and stained for Gr-1 (BD Pharmingen), CD45 (BD Pharmingen), or VCAM-1. Myeloperoxidase (MPO) activity was measured in lung homogenates using the Amplex Red Peroxidase Assay Kit (Invitrogen) according to the manufacturer's instructions. Animals were housed in pathogen-free barrier facilities and regularly monitored by the veterinary staff.

Statistics

Differences between two groups were examined using the Student's t-test (two-tailed) and were considered significant at $P<0.05$.

Example 2

Animal Model of Asthma

Asthma is a heterogeneous, complex disorder that involves airflow obstruction, airway hyperresponsiveness (AHR), and inflammation. Accumulating studies highlight a critical role for enhanced NF-κB pathway activation in asthmatic tissues. NF-κB activation leads to increased expression of adhesion molecules and chemokines on several cell types, including the lung endothelium. Thus, suppressing the inflammatory response in the pulmonary endothelium may provide a therapy in asthma patients.

An experimental model of asthma in mice will be used to study the effect of nucleic acids containing all or a part of the sequence of miR-181b (SEQ ID NO: 1) on asthma. The nucleic acids described herein, containing all or a part of the sequence of SEQ ID NO: 1, may suppress experimental asthma. In these studies, ovalbumin (OVA)-sensitized and challenged mice will be injected with one of the nucleic acids described herein (pre- or post-OVA challenge), and the miR-181b nucleic acid-mediated effects on endothelial cell activation and airway inflammation, airway hyperresponsiveness to methacholine challenge, expression of NF-κB-regulated genes, accumulation of eosinophils and leukocyte subsets in bronchoalveolar lavage fluid (BALF) and lung tissue, $CD4^+$ Th2 lymphocyte responses, and hypersecretion of mucus will be determined. A nucleic acid containing all or a part of the sequence of SEQ ID NO: 1 will be administered either by intravenous injection (tail vein) or by aerosol (nebulization). The nucleic acid containing all or a part of the sequence of SEQ ID NO: 1 may be admixed with cationic molecules such as collagen (e.g., atelocollagen, or type I telocollagen), lipofectin-based reagents, lipidoids, elastin-like peptides, small peptides (e.g., a RGD peptide, PEGylated with RGD, or a collagen), or polymeric microparticles, or non-cationic molecules, such as PGLA, or aptamers specific to endothelial cells to enhance systemic intravenous or aerosol delivery. Alternatively, the nucleic acid containing all or a part of the sequence of SEQ ID NO: 1 may be conjugated to molecules such as glucan particles for oral delivery. Effects on the action of NF-κB signaling in vivo will also be examined using the OVA-challenged, NF-κB-luciferase-GFP transgenic mice and bioluminescence imaging.

Example 3

Animal Models of Atherosclerosis

Arteriosclerosis and its complications are the leading cause of morbidity and mortality in Western societies. The lesions of atherosclerosis represent a series of highly specific cellular and molecular responses that can be viewed, in aggregate, as an inflammatory disease process. Experimental, pathologic, and clinic observations support a critical role for the activated endothelium in atherogenesis. Activated endothelial cells have been identified in every phase of atherosclerotic lesion development—from earliest lesion termed the "fatty streak" to the mature and obstructive plaque. NF-κB activation leads to induction of adhesion molecule expression in endothelial cells, an effect that leads to leukocyte accumulation within the vascular wall and atherosclerotic lesion formation.

An experimental model will be used to examine the effect of a nucleic acid containing all or a part of the sequence of SEQ ID NO: 1 on atherosclerosis initiation and progression in vivo. In the proposed studies, mice will be intravenously injected with a nucleic acid containing all or a part of the sequence of SEQ ID NO: 1 and controls, at least weekly in: atherosclerotic-prone LDL-R-deficient or ApoE-deficient 8-10 week old mice fed a high fat diet for 8 weeks (initiation studies), or after atherosclerotic-prone LDL-R-deficient or ApoE-deficient mice have already been fed a high fat diet for at least 8 weeks (progression studies). The severity of atherosclerotic lesion formation and the cellular composition of the lesions in the aortic sinus and descending aorta will be determined using standard immunohistochemical techniques.

Example 4

Animal Models of Obesity

Obesity contributes to a significant health epidemic and is a major risk factor for coronary artery disease and diabetes, and other chronic inflammatory disease states, such as degenerative neurological disease, lung airway disease, diabetic retinopathy, and cancer. Indeed, almost two-thirds of American adults are overweight. Obesity is associated with chronic inflammatory signaling pathways, such as NF-κB. Clinical and experimental studies indicate that activation of the NF-κB signaling pathway can increase insulin resistance and type 2 diabetes. Thus, targeting the NF-κB signaling pathway may offer a strategy for treating obesity and decreasing cellular inflammation.

The effect of a nucleic acid containing all or a part of the sequence of SEQ ID NO: 1 on obesity and insulin resistance will be studied using animal models. In these experiments, a nucleic acid containing all or a part of the sequence of SEQ ID NO: 1 will be injected intravenously at least weekly in one or more of four models of obesity for a total of four weeks: Zucker fatty rats, ob/ob mice, db/db mice, and C57BL/6 mice fed a high-fat diet. Blood glucose and insulin concentrations will be measured during glucose tolerance testing. Insulin sensitivity will be measured using insulin tolerance tests. Lipid profiles (cholesterol, LDL, triglyceride, and HDL) and free fatty acid levels will also be measured. Finally, body composition will be analyzed including visceral and subcutaneous fat profiles. The activity of NF-κB (e.g., expression of NF-κB target genes) will be examined in fat, liver, and skeletal muscles. Finally, body weights, energy expenditure, and caloric consumption will be analyzed. A nucleic acid containing all or a part of the sequence of SEQ ID NO: 1 may improve insulin sensitivity, reduce glucose levels, reduce free fatty acid levels, and improve body weight and composition.

Example 5

Animal Models of Rheumatoid Arthritis (RA)

Rheumatoid arthritis is a systemic chronic inflammatory disease that primarily attacks the synovial joints, an effect leading to destruction of articular cartilage and joints with considerable disabling, painful morbidity. Indeed, about 1% of the world's population is affected by RA. Clinical and experimental studies indicate that activation of NF-κB signaling pathway is one of the principal targets in RA. NF-κB promotes the accumulation of leukocytes, abnormal growth of fibroblast-like synovial cells, and is involved in the differentiation and activation of bone-resorbing activity of osteoclasts. Current drug therapies, such as TNF-α antagonists, such as etanercept, infliximab, or adalimumab, or IL-1 antagonists, such as anakinra, block activation of NF-κB signaling and RA disease progression. However, side effects may be associated with these drugs. Furthermore, downstream targeting of TNF-α or IL-1 may provide a more potent and specific method of reducing NF-κB activation. Thus, targeting the NF-κB signaling pathway may offer novel strategies for limiting RA disease progression.

The effect of a nucleic acid containing all or a part of the sequence of SEQ ID NO: 1 on rheumatoid arthritis is being studied in an animal model. In these experiments, a nucleic acid containing all or a part of the sequence of SEQ ID NO: 1 is injected intravenously at least weekly in three models of RA: rat adjuvant arthritis, rat type II collagen arthritis, or mouse type II collagen arthritis. For the adjuvant model, treatment is administered either at day 0 (prophylactic model) or day 8 (therapeutic model). The study is terminated on day 15. The tibiotarsal joint and foot paws are examined for inflammation and arthritic parameters. For the rat type II collagen arthritis model, rats are given type II collagen (2 mg/mL in incomplete Freund's adjuvant) on day 0 and day 7. Onset of arthritis occurs on days 10-13. Rats are harvested for histopathological evaluation at the completion of treatment. For the mouse type II collagen model, DBA/1 lacJ mice are immunized against bovine type II collagen at day 0 and day 21 with and without concurrent boosting with endotoxin or recombinant IL-1. The disease occurs in paws/joints and measurements of disease are determined clinically and with histological scoring. NF-κB activity (e.g., the expression of NF-κB target genes) is examined in tissues. This model has been used to evaluate effects of IL-1 and soluble TNF-α receptor antagonists. Both prophylactic and treatment studies are performed using a nucleic acid containing all or a part of the sequence of SEQ ID NO: 1. A nucleic acid containing all or a part of the sequence of SEQ ID NO: 1 may inhibit NF-κB activity in tissues and may reduce RA disease.

Example 6

Animal Models of Crohn's Disease and Ulcerative Colitis

Crohn's disease and ulcerative colitis are common inflammatory bowel diseases that can affect portions of the gastrointestinal tract and can cause significant symptoms and morbidity. It is estimated that ~1 million people in the U.S. are affected by inflammatory bowel disease (IBD). Treatment options are quite limited to maintaining remission, preventing relapse, and controlling symptoms. Clinical and experimental studies indicate higher levels of expression of NF-κB signaling pathway in biopsy samples from patients with IBD. Immunomodulating agents, such as corticosteroids, which reduce NF-κB activation, are helpful in patients, but have numerous side effects. Thus, targeting NF-κB signaling pathway may offer novel strategies for limiting IBD disease progression.

The effect of a nucleic acid containing all or a part of the sequence of SEQ ID NO: 1 on IBD is studied using an animal model. In these experiments, a nucleic acid containing all or a part of the sequence of SEQ ID NO: 1 is injected intravenously at least weekly in three models of IBD in mice: chemically-induced IBD, genetically-modified IL-10-deficient or TNF delta ARE mice, or spontaneous IBD strains of mice (SAMP1/Yit). For the chemically-induced model, dextran sodium sulfate (DSS) is used, which is well-characterized for inducing epithelial disruption resulting in bacterial and neutrophil infiltration, and represents a model of the acute phase of injury. IL-10-deficient mice have a transmural colitis and are useful to assess the role of specific cytokine signaling pathways. TNF delta ARE mice represent a model of Crohn's-like disease with ileal involvement. This is an important model as TNF-α contributes to the pathogenesis of Crohn's disease and up to 70% of patients with refractory Crohn's disease respond to TNF-α blocking treatment. The SAMP1/Yit model of ileitis also provides a stable model of IBD and has implicated vascular adhesion molecules, such as VCAM-1, as being important for leukocyte trafficking and accumulation in IBD development. Indeed, blocking antibodies to VCAM-1 and ICAM-1 leads to a 70% improvement in severity of inflammation. For each of these models, a nucleic acid containing all or a part of the sequence of SEQ ID NO: 1 is intravenously injected at least weekly in: prophylactic studies (early in the course of disease, e.g., 4-6 weeks), or treatment studies (after established IBD is observed (varies between 8-20 weeks depending on the model)). The severity of IBD and the cellular composition of the gastrointestinal tract is determined using standard immunohistochemical techniques. A nucleic acid containing all or a part of the sequence of SEQ ID NO: 1 may inhibit the progression of IBD.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating atherosclerosis in a subject, the method comprising:
   identifying a subject in need of treatment for atherosclerosis, and
   administering to the subject a therapeutically effective amount of a nucleic acid comprising SEQ ID NO: 1.

2. A method of treating atherosclerosis in a subject, the method comprising:
   identifying a subject in need of treatment for atherosclerosis, and
   administering to the subject a therapeutically effective amount of a nucleic acid comprising SEQ ID NO: 2.

3. The method of claim 1, wherein said nucleic acid is conjugated to one or more of a polymer, a peptide, and a polysaccharide.

4. The method of claim 1, wherein said nucleic acid is conjugated to a lipid moiety.

5. The method of claim 2, wherein the nucleic acid is conjugated to a lipid moiety.

6. The method of claim 1, wherein the nucleic acid is delivered in liposomes.

7. The method of claim 2, wherein the nucleic acid is delivered in liposomes.

8. A method of treating atherosclerosis in a subject, the method comprising:
   identifying a subject in need of treatment for atherosclerosis, and
   administering to the subject a therapeutically effective amount of a nucleic acid comprising SEQ ID NO: 3.

9. The method of claim 8, wherein the nucleic acid is conjugated to a lipid moiety.

10. The method of claim 8, wherein the nucleic acid is delivered in liposomes.

* * * * *